US00RE49362E

(19) United States
(12) Reissued Patent
Barnes et al.

(10) Patent Number: US RE49,362 E
(45) Date of Reissued Patent: Jan. 10, 2023

(54) DYE COMPOUNDS AND THE USE OF THEIR LABELLED CONJUGATES

(71) Applicant: Illumina Cambridge Limited, Cambridge (GB)

(72) Inventors: Colin Barnes, Cambridge (GB); Nikolai Nikolaevich Romanov, Cambridge (GB)

(73) Assignee: Illumina Cambridge Limited, Cambridge (GB)

(21) Appl. No.: 16/917,713

(22) Filed: Jun. 30, 2020

Related U.S. Patent Documents

Reissue of:
(64) Patent No.: 8,178,360
Issued: May 15, 2012
Appl. No.: 12/227,474
PCT Filed: May 16, 2007
PCT No.: PCT/GB2007/001770
§ 371 (c)(1),
(2) Date: Mar. 16, 2009
PCT Pub. No.: WO2007/135368
PCT Pub. Date: Nov. 29, 2007

U.S. Applications:
(60) Provisional application No. 60/801,270, filed on May 18, 2006.

(51) Int. Cl.
*G01N 33/58* (2006.01)
*A61K 49/00* (2006.01)
*C09B 11/24* (2006.01)

(52) U.S. Cl.
CPC ..... *G01N 33/582* (2013.01); *A61K 49/0041* (2013.01); *A61K 49/0052* (2013.01); *C09B 11/24* (2013.01); *Y10S 436/80* (2013.01)

(58) Field of Classification Search
CPC ..... G01N 33/582; A61K 49/0041; A61K 49/0052; C09B 11/24; Y10S 436/80
See application file for complete search history.

(56) References Cited

U.S. PATENT DOCUMENTS

| | | | |
|---|---|---|---|
| 4,647,675 | A | 3/1987 | Mayer et al. |
| 4,900,686 | A | 2/1990 | Arnost et al. |
| 5,750,409 | A | 5/1998 | Herrmann et al. |
| 5,792,389 | A | 8/1998 | Hammond et al. |
| 5,936,087 | A | 8/1999 | Benson et al. |
| 6,130,101 | A | 10/2000 | Mao et al. |
| 6,184,379 | B1 | 2/2001 | Josel et al. |
| 6,323,337 | B1 | 11/2001 | Singer et al. |
| 6,399,392 | B1 | 6/2002 | Haugland et al. |
| 6,448,407 | B1 | 9/2002 | Lee et al. |
| 6,583,168 | B1 | 6/2003 | Menchen et al. |
| 6,649,769 | B2 | 11/2003 | Lee et al. |
| 6,713,622 | B1 | 3/2004 | Graham |
| 6,750,357 | B1 | 6/2004 | Chiarello et al. |
| 7,038,063 | B2 | 5/2006 | Lee et al. |
| 7,198,958 | B2 | 4/2007 | Meltola et al. |
| 2002/0034761 | A1 | 3/2002 | Benson et al. |
| 2002/0155381 | A1 | 10/2002 | Berneth et al. |
| 2003/0104437 | A1 | 6/2003 | Barnes et al. |
| 2004/0076979 | A1 | 4/2004 | Belik et al. |
| 2005/0170363 | A1 | 8/2005 | Reddington et al. |
| 2005/0239073 | A1 | 10/2005 | Trinquet et al. |
| 2005/0278872 | A1 | 12/2005 | Lagrange |
| 2006/0154251 | A1 | 7/2006 | Arden-Jacob et al. |
| 2006/0179585 | A1 | 8/2006 | Zilles et al. |
| 2006/0183046 | A1 | 8/2006 | Murai et al. |
| 2008/0177086 | A1 | 7/2008 | Frank et al. |
| 2009/0093612 | A1 | 4/2009 | Lukhtanov |
| 2010/0009353 | A1 | 1/2010 | Barnes et al. |
| 2010/0291547 | A1 | 11/2010 | Chen et al. |
| 2011/0124510 | A1 | 5/2011 | Benson et al. |
| 2011/0294675 | A1 | 12/2011 | Brabetz et al. |
| 2012/0003151 | A1 | 1/2012 | Low et al. |
| 2013/0079232 | A1 | 3/2013 | Kain et al. |
| 2013/0344499 | A1 | 12/2013 | Wang |
| 2014/0255920 | A1 | 9/2014 | Romanov et al. |
| 2014/0271468 | A1 | 9/2014 | Low et al. |
| 2016/0187547 | A1 | 6/2016 | Murata et al. |
| 2016/0274112 | A1 | 9/2016 | Zlotnick et al. |
| 2016/0362418 | A1 | 12/2016 | Polukhtin |
| 2017/0044372 | A1 | 2/2017 | Gee et al. |
| 2017/0145216 | A1 | 5/2017 | Suzuki et al. |
| 2018/0194943 | A1 | 7/2018 | Grund |
| 2019/0100653 | A1 | 4/2019 | Kemnitzer et al. |

FOREIGN PATENT DOCUMENTS

| | | |
|---|---|---|
| AU | 2008200036 | 1/2008 |
| CN | 102636957 | 8/2012 |
| CN | 106946838 | 7/2017 |
| EP | 0 272 007 | 6/1988 |
| EP | 0 285 179 | 10/1988 |
| EP | 0 805 441 | 11/1997 |
| EP | 0 966 458 | 8/2003 |
| EP | 1 408 090 | 4/2004 |
| EP | 1 401 962 | 9/2006 |
| EP | 1 828 412 | 11/2012 |
| FR | 2889060 | 2/2007 |
| JP | 09-087534 | 3/1997 |
| JP | 09-241553 | 9/1997 |
| JP | 2011-241372 | 12/2011 |
| JP | 2012-036256 | 2/2012 |

(Continued)

OTHER PUBLICATIONS

ATTO-TEC GmbH, 2018, ATTO 532 and 550 Product Information, https://www.atto-tec.com/product_info/php?infor=p102_atto-532.html, 8 pp.
Armitage, 2005, Cyanine Dye—DNA Interactions: Intercalation, Groove Binding, and Aggregation, Top Curr Chem, 253:55-76.
Beck et al., 2002, Fluorophore-assisted light inactivation A high-throughput tool for direct target validation of proteins, Proteomics, 2:247- 255.

(Continued)

*Primary Examiner* — Alan D Diamond
*Assistant Examiner* — Jerry D Johnson
(74) *Attorney, Agent, or Firm* — Knobbe, Martens, Olson & Bear, LLP

(57) ABSTRACT

Novel rhodamine dye compounds, labelled conjugates comprising the dyes are described, together with methods for their use. The dyes and labelled conjugates are useful as molecular probes in a variety of applications, such as in assays involving staining of cells, protein binding, and analysis of nucleic acids, such as hybridization assays and nucleic acid sequencing.

72 Claims, No Drawings

(56) References Cited

FOREIGN PATENT DOCUMENTS

| | | |
|---|---|---|
| JP | 2014-056214 | 3/2014 |
| JP | 2014-109017 | 6/2014 |
| JP | 2014-115381 | 6/2014 |
| JP | 2014-167554 | 9/2014 |
| JP | 2014-177567 | 9/2014 |
| JP | 2014-201715 | 10/2014 |
| JP | 2014-208815 | 11/2014 |
| JP | 2017-198815 | 11/2017 |
| JP | 2019-124874 | 7/2019 |
| KR | 2011-103861 | 9/2011 |
| KR | 2011-109033 | 10/2011 |
| KR | 2013-137537 | 12/2013 |
| WO | WO 91/06678 | 5/1991 |
| WO | 99/15517 | 4/1999 |
| WO | WO 99/15517 | 4/1999 |
| WO | 00/64988 | 11/2000 |
| WO | WO 00/64988 | 11/2000 |
| WO | WO 02/29003 | 4/2001 |
| WO | 02/12195 | 2/2002 |
| WO | WO 02/12195 | 2/2002 |
| WO | 02/055512 | 7/2002 |
| WO | WO 02/055512 | 7/2002 |
| WO | 2004/018493 | 3/2004 |
| WO | 2004/018497 | 3/2004 |
| WO | WO 04/018493 | 3/2004 |
| WO | WO 04/018497 | 3/2004 |
| WO | 2004/055117 | 7/2004 |
| WO | WO 04/055117 | 7/2004 |
| WO | 2004/101709 | 11/2004 |
| WO | WO 04/101709 | 11/2004 |
| WO | 2005/003086 | 1/2005 |
| WO | WO 05/003086 | 1/2005 |
| WO | WO 09/051807 | 4/2009 |
| WO | WO 14/150943 | 9/2014 |
| WO | WO 15/137224 | 9/2015 |

OTHER PUBLICATIONS

Boutorine et al., 1996, Chlorin-Oligonucleotide Conjugates: Synthesis, Properties, and Red Light-Induced Photochemical Sequence-Specific DNA Cleavage in Duplexes and Triplexes, J. Am. Chem. Soc., 118(40).

DeRosa et al., 2002, Photosensitized singlet oxygen and its applications' Coordination Chemistry Reviews, 233-234:351-371.

Drexhage, 1976, Fluorescence Efficiency of Laser Dyes, J Res Natl Bur Stand A Phys Chem, 80A(3):421-428.

Foote, 1968, Mechanisms of Photosensitized Oxidation, Science, 162:3857.

Haugland, 2002, Handbook of Fluorescent Probes and Research Products, Chapter 19, 9th Edition.

Hockberger, May 2000, Sources and Remedies of Phototoxicity in Live Cell Microscopy, Microscopy Today, 8:30-32.

Kapanidis et al., 2002, Fluorescent probes and bioconjugation chemistries for single-molecule fluorescence analysis of biomolecules, J. Chem. Phys. 117(24):10953-10964.

Klonis et al., 2003, The Thiourea Group Modulates the Fluorescence Emission Decay of Fluorescein-labeled Molecules, Photochemistry and Photobiology, 77(5):502-509.

Lakowicz, 1999, DNA Technology, Chapter 21; 595-617 in Principles of Fluorescence Spectroscopy.

Murphy, 2001, Differential Interference Contrast Microscopy and Modulation Contrast Microscopy, Chapter 11, 1st Edition in Fundamentals of Light Microscopy and Electronic Imaging.

Nazarenko et al., 2002, Multiplex quantitative PCR using self-quenched primers labelled with a single fluorophore, Nucleic Acids Research, 30:9.

Nguyen et al., 2003, Practical Synthetic Route to Functionalized Rhodamine Dyes, Org. Lett., 5(18):3245-3248.

Privat et al., 2002, Fluorescent properties of oligonucleotide-conjugated thiazole orange probes, Photochemistry and Photobiology, 75(3):203.

Prober et al., 1987, A system for rapid DNA sequencing with fluorescent chain-terminating dideoxynucleotides, Science 238(4825):336-341.

Rettig et al., 1999, Photostability of Fluorescent Dyes for Single-Molecule Spectroscopy, Chapter 10 in Applied Fluorescence in Chemistry, Biology and Medicine.

Rothwell et al., 2003, Multiparameter single-molecule fluorescence spectroscopy reveals heterogeneity of HIV-1 reverse transcriptase: primer/template complexes, PNAS, 100(4): 1655-1660.

Skorobogatyi et al., 2006, Fluorescent 5-Alkynyl-2'-Deoxyuridines: High Emission Efficiency of a Conjugated Perylene Nucleoside in a DNA Duplex, ChemBioChem, 7:810-816.

Smith et al., 1986, Fluorescence detection in automated DNA sequence analysis, Nature, 321:674-679.

Stelzer, 2015, Light-sheet fluorescence microscopy for quantitative biology, Nature Methods, 12(1):23-26.

Sugden, 2004, Photochemistry of dyes and fluorochromes used in biology and medicine, Biotechnic & Histochemistry, 79(2):71-90.

Tsien and Waggoner, 1995, Fluorophores for Confocal Microscopy, Chapter 16: 267-279 in Handbook of Biological Confocal Microscopy.

Vigers et al., 1988, Fluorescent Microtubules Break Up Under Illumination, J. Cell. Bio, 107:1011-1024.

Atto-Tec, Fluorescent Labels and Dyes for Biology and Analytics, Catalogue 2004-2005, 27 pp.

Sigma-Aldrich, May 2002, Certificate of Analysis, 4-(Methylamino)butyric acid hydrochloride, 1 p.

Balasubramanian, 2011, Sequencing nucleic acids; from chemistry to medicine, Chem. Commun., 47:7281-7286.

Balasubramanian, 2014, Chemical biology on the genome, Bioorganic & Medicinal Chemistry, 22:4356-4370.

Bentley et al., Nov. 6, 2008, Accurate whole human genome sequencing using reversible terminator chemistry, Nature, 456:53-59 and supplementary information.

Davies, 2010, The $1,000 Genome, Chapter 5. The British Invasion, Free Press, pp. 102-115, 298-299.

Hermanson, 1996, Bioconjugate Techniques, Academic Press, Inc., TOC.

Guo et al., Jul. 8, 2008, Four-color DNA sequencing with 3'-0-modified nucleotide reversible terminators and chemically cleavable fluorescent dideoxynucleotides, PNAS, 105(27):9145-9150.

Panchuk-Voloshina et al., 1999, Alexa Dyes, a Series of New Fluorescent Dyes that Yield Exceptionally Bright, Photostable Conjugates, J. Hist. & Cyto, 47(9):1179-1188.

Stratagene Catalog, 1988, p. 39.

Daré-Doyen, et al., Dimerization of Xanthene Dyes in Water: Experimental Studies and Molecular Dynamic Simulations, *Journal of Physical Chemistry*, vol. 107, No. 50, pp. 13803-13812.

DYE COMPOUNDS AND THE USE OF THEIR LABELLED CONJUGATES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

The present application is a National Stage Application claiming the priority of co-pending PCT Application No. PCT/GB2007/001770, filed May 16, 2007, which in turn, claims priority from U.S. Provisional Application Ser. No. 60/801,270, filed May 18, 2006. Applicants claim the benefits of 35 U.S.C. § 120 as to the PCT application and priority under 35 U.S.C. § 119 as to the said U.S. Provisional application, and the entire disclosures of both applications are incorporated herein by reference in their entireties.

FIELD OF THE INVENTION

The present invention provides novel rhodamine dye compounds, labelled conjugates comprising the dyes and methods for their use. The dyes and labelled conjugates are useful as molecular probes in a variety of applications, such as in assays involving staining of cells, protein binding, and analysis of nucleic acids, such as hybridization assays and nucleic acid sequencing. More particularly the invention relates to the use of such dyes in solid phase sequencing by synthesis.

BACKGROUND TO THE INVENTION

Several publications and patent documents are referenced in this application in order to more fully describe the state of the art to which this invention pertains. The disclosure of each of these publications and documents is incorporated by reference herein.

Non-radioactive detection of nucleic acids utilizing fluorescent labels is an important technology in molecular biology. Many procedures employed in recombinant DNA technology previously relied heavily on the use of nucleotides or polynucleotides radioactively labelled with, for example $^{32}P$. Radioactive compounds permit sensitive detection of nucleic acids and other molecules of interest. However, there are serious limitations in the use of radioactive isotopes such as their expense, limited shelf life and more importantly safety considerations. Eliminating the need for radioactive labels enhances safety whilst reducing the environmental impact and costs associated with, for example, reagent disposal. Methods amenable to non-radioactive fluorescent detection include by way of non-limiting example, automated DNA sequencing, hybridization methods, real-time detection of polymerase-chain-reaction products and immunoassays.

For many applications it is desirable to employ multiple spectrally distinguishable fluorescent labels in order to achieve independent detection of a plurality of spatially overlapping analytes. In such multiplex methods the number of reaction vessels may be reduced simplifying experimental protocols and facilitating the production of application-specific reagent kits. In multi-colour automated DNA sequencing for example, multiplex fluorescent detection allows for the analysis of multiple nucleotide bases in a single electrophoresis lane thereby increasing throughput over single-colour methods and reducing uncertainties associated with inter-lane electrophoretic mobility variations.

However, multiplex fluorescent detection can be problematic and there are a number of important factors which constrain selection of fluorescent labels. First, it is difficult to find dye compounds whose emission spectra are suitably spectrally resolved. In addition when several fluorescent dyes are used together, simultaneous excitation may be difficult because the absorption bands of the dyes are usually widely separated. Many excitation methods use high power lasers and therefore the dye must have sufficient photostability to withstand such laser excitation. A final consideration of particular importance in molecular biology methods is that the fluorescent dyes must be compatible with the reagent chemistries used such as for example DNA synthesis solvents and reagents, buffers, polymerase enzymes and ligase enzymes.

As sequencing technology advances a need has developed for further fluorescent dye compounds, their nucleic acid conjugates and dye sets which satisfy all of the above constraints and which are amenable particularly to high throughput molecular methods such as solid phase sequencing and the like.

SUMMARY OF THE INVENTION

According to a first aspect the invention provides rhodamine dye compounds of the formula (I):

Formula (I)

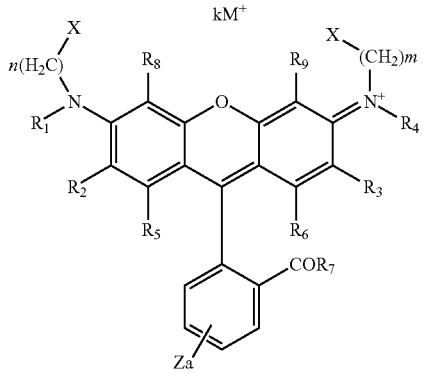

wherein X is a sulfo- or sulfonato- group, $SO_3H$ or $SO_3^-$, $M^+$ is a common counter ion, k, n, m are independently integers of from 1 to 6, $R_1$ is H or an alkyl or substituted alkyl group, $R_2$ is H, alkyl or substituted alkyl group, halogen, carboxy, carboxamide, hydroxy- or alkoxy group, or $R_2$ together with $R_1$ or $R_5$ is a carbon or heterosubstituted chain forming a ring, $R_3$ is H, alkyl or substituted alkyl group, halogen, carboxy, carboxamide, hydroxy- or alkoxy group or $R_3$ together with $R_4$ or $R_6$ is a carbon or heterosubstituted chain forming a ring, $R_4$ is H, or an alkyl or substituted alkyl group, $R_5$ and $R_6$ are H, alkyl or substituted alkyl group, halogen, hydroxy- or alkoxy group, $R_8$is H, halogen, hydroxy- or alkoxy group, alkyl or substituted alkyl group or together with $R_1$ is a carbon or heterosubstituted carbon chain forming a ring, $R_9$ is H, halogen, hydroxy- or alkoxy group, alkyl or substituted alkyl group or together with $R_4$ is a carbon or heterosubstituted carbon chain forming a ring, $R_7$ is OH, $OR_{10}$ where $R_{10}$ is alkyl or substituted alkyl, or $NR_{11}R_{12}$ where $R_{11}$ and $R_{12}$ are independently H, alkyl or a substituted alkyl, or is joined to form aliphatic or aromatic cyclic or substituted aliphatic-, aromatic- or heterocyclic rings, Z is a H, halogen, amino or substituted amino, hydroxyl-, alkoxy-, carboxy-, carboxamido- or substituted carboxamido group, $SO_3H$ or $SO_3^-$ and a is 0 to 4.

In another embodiment the compounds of the present invention can be conjugated with a variety of substrate moieties such as, for example, nucleosides, nucleotides, polynucleotides, polypeptides, carbohydrates, ligands, particles and surfaces.

According to a second aspect of the invention therefore, there are provided dye compounds comprising linker groups to enable, for example, covalent attachment to such substrate moieties.

According to a third aspect the invention provides a nucleoside or nucleotide compound defined by the formula:

N-L-Dye wherein N is a nucleotide, L is an optional linker moiety and Dye is a compound according to the present invention and wherein said compound is a fluorescent compound.

In a fourth aspect the invention includes methods of sequencing using the dye compounds of the present invention.

According to a fifth aspect the invention also provides kits comprising dye compounds of the invention (free or in conjugate form) which may be used in various immunological assays, oligonucleotide and nucleic acid labelling and for DNA sequencing by synthesis. In yet another aspect the invention provides kits comprising dye 'sets' particularly suited to cycles of sequencing by synthesis on an automated instrument platform.

DETAILED DESCRIPTION OF THE INVENTION

The invention relates to novel rhodamine dye compounds particularly suitable for methods of fluorescence detection and sequencing by synthesis.

In reference to rhodamine dyes, the Colour Index (Association of Textile Chemists, 2nd. Ed., 1971) numbering scheme is used to identify the carbon atoms of the rhodamine dyes.

According to the first aspect the invention provides compounds of the formula (I):

Formula (I)

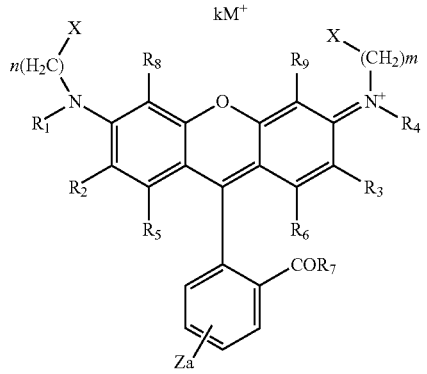

wherein X is $SO_3H$ or $SO_3^-$, k, n, m are independently integers of from 1 to 6, $M^+$ is a common counter ion.

As used herein, the term "common counter ion" includes well known cations such as by way of non-limiting example $Na^+$, $K^+$, $Li^+$ and $NH_4^+$, $NEt_3H^+$, and the like. See, Whitten, K. W., and Gailey, K. D., General Chemistry, Saunders College Publishing, p. 167, 1981 and James E. Huheey, Inorganic Chemistry, 3rd ed., Harper & Row, pp. A-97-A-103, 1983, which are incorporated herein by reference. In some cases, the compounds include such a common counter ion to help balance the charge of the molecule.

$R_1$ is H or an alkyl group or substituted alkyl group, $R_2$ is H, halogen, alkyl group or substituted alkyl group, hydroxy- or alkoxy $R_3$ is H, halogen or alkyl group or substituted alkyl group, hydroxy- or alkoxy $R_4$ is H or a alkyl or substituted alkyl group, $R_8$ is H, halogen, hydroxy- or alkoxy groups, alkyl or substituted alkyl, $R_9$ is H, halogen, hydroxy- or alkoxy groups, alkyl or substituted alkyl In another embodiment, $R_1$ and $R_2$ or $R_8$ and/or $R_4$ and $R_3$ or $R_9$ and/or $R_2$ and $R_5$ and/or $R_3$ and $R_6$ can be connected to form carbo- or heterocyclic rings, an example being five or six membered aliphatic rings, which may contain one or more double bonds. $R_5$ and $R_6$ are H, alkyl or substituted alkyl, halogen, hydroxyl- or alkoxy, $R_7$ may be OH, $OR_{10}$ where $R_{10}$ is alkyl or substituted alkyl, or $NR_{11}R_{12}$ where $R_{11}$ and $R_{12}$ are independently H, alkyl or a substituted alkyl, or may be joined together in the form of cyclic or substituted cyclic rings, Z is a H, halogen, amino or substituted amino, hydroxy-, alkoxy-, carboxy, carboxamido or substituted carboxamido, $SO_3H$ or $SO_3^-$ and a is 0 to 4.

As used herein, the term "Alkyl" refers to $C_1$-$C_{20}$ hydrocarbon and may include $C_3$-$C_{10}$ non-aromatic carbocyclic rings. In particular embodiments the alkyl groups are $C_1$-$C_6$ alkyl which refers to saturated, straight- or branched-chain hydrocarbon radicals containing between one and six carbon atoms, respectively.

The term "alkenyl" as used herein represents $C_1$-$C_{20}$ hydrocarbon containing at least one double bond and may include $C_3$-$C_{10}$ non-aromatic carbocyclic rings.

The term "alkynyl" as used herein represents $C_1$-$C_{20}$ hydrocarbon containing at least one triple bond and may include $C_3$-$C_{10}$ non-aromatic carbocyclic rings.

The term "aryl" as used herein represents an aromatic carbocyclic ring optionally selected from but not limited to phenyl optionally substituted with common aromatic substituents.

The term "halogen" as used herein refers to fluoro—(hereafter designated as F), chloro—(hereafter designated as Cl), bromo—(hereafter designated as Br) or iodo—(hereafter designated as I), and usually relates to substitution for a hydrogen atom in an organic compound, this substitution is optionally a full substitution for the hydrogen.

The terms "substituted alkyl", "substituted alkenyl" and "substituted alkynyl" refers to alkyl, alkenyl or alkynyl groups as defined above where they may optionally be further substituted with, but not limited to, Halo, Cyano, $SO_3^-$, $SR_{12}$, $OR_{12}$, $NR_{13}R_{14}$, oxo, $CONR_{13}R_{14}$, COOH and $COOR_{13}$. Wherein $R_{13}$ and $R_{14}$ are each independently selected from H, alkyl, substituted alkyl, alkenyl, substituted alkenyl, alkynyl, substituted alkynyl, aryl and substituted aryl. Further, said substituted alkyl, substituted alkenyl and substituted alkynyl may optionally be interrupted by at least one hetero atom or group selected from O, $NR_{12}$, S(O), wherein t is 0 to 2, and the like. Substituted alkyl also covers group such as benzyl where the alkyl groups is comprises a further aryl or substituted aryl moiety.

Thus particular compounds according to a first aspect of the present invention are:

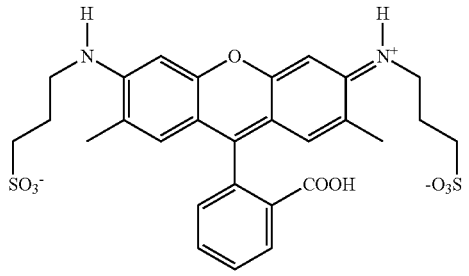

Dye 1

Wherein X is $SO_3^-$, n is 3, $R_1$, $R_4$, $R_5$, $R_6$, $R_8$ and $R_9$ are all H, $R_2$ and $R_3$ are $CH_3$, a is 0 and $R_7$ is OH.
And:

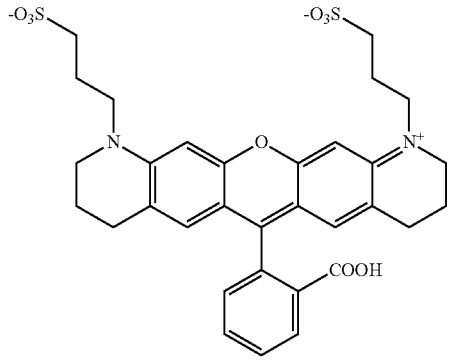

Dye 2

Wherein X is $SO_3^-$, n is 3, $R_1$ and $R_2$ form a six membered ring $R_3$ and $R_4$ form a six membered ring, $R_5$, $R_6$, $R_8$ and $R_9$ are H, a is 0 and $R_7$ is OH.

Dyes according to the present invention may be synthesised from a variety of different starting materials, including N-sulfonatoalkyl derivatives of 3-aminophenol, 5-hydroxy-1,2,3,4-tetrahydroquinoline or 7-hydroxy-1,2,3,4-tetrahydroquinoline. Condensation of these compounds with substituted or unsubstituted phthalic anhydrides gives the dyes as described. The condensation reaction is typically carried out at high temperature with or without suitable solvent, and is assisted by the use of microwave irradiation. The use of ionic liquids, for example 1-ethyl-3-methylimidazolium, as solvent in said condensation reactions is especially advantageous. The reaction can be catalysed by Lewis acids, for example zinc chloride.

Preparation of N-sulfonatoalkyl-5-hydroxy-1,2,3,4-tetrahydroquinoline or N-sulfonatoalkyl-7-hydroxy-1,2,3,4-tetrahydroquinoline can be carried out using catalytic hydrogenation, for example using Raney Nickel as a catalyst. The addition of an organic or inorganic base, for example triethylamine, greatly enhances the rate of reaction.

Mono N-alkylation of 3-aminophenols with alkylsultones can be carried out using one equivalent or more of the aminophenol. Di-alkylation of 3-amino phenol can be achieved using more equivalents of the alkylsultone. Both of the resultant phenolic derivatives can be condensed with phthalic anhydride to make fluorophores as described.

According to a second aspect of the invention there are provided dye compounds suitable for attachment to substrate moieties, particularly comprising linker groups to enable attachment to substrate moieties. Substrate moieties can be virtually any molecule or substance to which the dyes of the invention can be conjugated and, by way of non-limiting example, may include nucleosides, nucleotides, polynucleotides, carbohydrates, ligands, particles, solid surfaces, organic and inorganic polymers and combinations or assemblages thereof, such as chromosomes, nuclei, living cells and the like. The dyes can be conjugated by an optional linker by a variety of means including hydrophobic attraction, ionic attraction and covalent attachment. Particularly the dyes are conjugated to the substrate by covalent attachment. More particularly the covalent attachment is by means of a linker group.

The dyes according to the invention may include a reactive linker group at one of the substituent positions for covalent attachment of the dye to another molecule. Reactive linking groups are moieties capable of forming a covalent bond. In a particular embodiment the linker may be a cleavable linker. Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Particular linker groups may be found in pending patent application number WO2004/018493 (herein incorporated by reference) wherein the present inventors have found that certain linkers which connect the bases of nucleotides to labels such as, for example, dyes according to the present invention, may be cleaved using water-soluble phosphines or water-soluble transition metal catalysts formed from a transition metal and at least partially water-soluble ligands. In aqueous solution the latter form at least partially water-soluble transition metal complexes.

Particular linkers may be found in Applicants pending International application WO2004/018493 (herein incorporated by reference) and may comprise moieties of the formula:

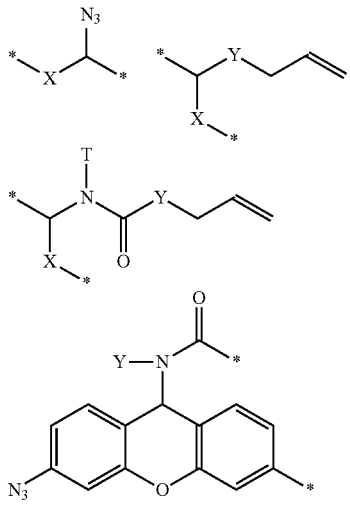

(wherein X is selected from the group comprising O, S, NH and NQ wherein Q is a $C_{1-10}$ substituted or unsubstituted alkyl group, Y is selected from the group comprising O, S, NH and N(allyl), T is hydrogen or a $C_{1-10}$ substituted or unsubstituted alkyl group and * indicates where the moiety is connected to the remainder of the nucleotide or nucleoside).

Still yet more particularly the inventors have determined in pending GB patent application number 0517097.2, published as WO07020457, (herein incorporated by reference) that by altering, and in particular increasing, the length of the linker between a fluorescent dye (fluorophore) and the guanine base, by introducing a polyethylene glycol spacer group, it is possible to increase the fluorescence intensity compared to the same fluorophore attached to the guanine base through other linkages known in the art. The design of the linkers, and especially their increased length, also allows improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula —$((CH_2)_2O)_n$— wherein n is an integer between 2 and 50, as described in applicants pending application number GB0517097.2 (WO07020457).

The present invention further provides conjugates of nucleosides and nucleotides labelled with dyes according to the invention (modified nucleotides). Labelled nucleosides and nucleotides are useful for labelling polynucleotides formed by enzymatic synthesis, such as, by way of non-limiting example, in PCR amplification, isothermal amplification or solid phase amplification, polynucleotide sequencing including solid phase sequencing, nick translation reactions and the like.

Nucleosides and nucleotides may be labelled at sites on the sugar or nucleobase. As known in the art, a "nucleotide" consists of a nitrogenous base, a sugar, and one or more phosphate groups. In RNA the sugar is ribose and in DNA is a deoxyribose, i.e. a sugar lacking a hydroxyl group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxyl group attached to the C-3 or C-5 of the sugar. Nucleotides are usually mono, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. The derivatives should be capable of undergoing Watson-Crick pairing. "Derivative" and "analogue" also mean a synthetic nucleotide or nucleoside derivative having modified base moieties and/or modified sugar moieties. Such derivatives and analogues are discussed in, for example, Scheit, Nucleotide analogs (John Wiley & Son, 1980) and Uhlman et al., Chemical Reviews 90:543-584, 1990. Nucleotide analogues can also comprise modified phosphodiester linkages including phosphorothioate, phosphorodithioate, alkyl-phosphonate, phosphoranilidate, phosphoramidate linkages and the like.

The dye may be attached to any position on the nucleotide base, through a linker, provided that Watson-Crick base pairing can still be carried out. Particular nucleobase labelling sites include the C5 position of a pyrimidine base or the C7 position of a 7-deaza purine base. As described above a linker group may be used to covalently attach a dye to the nucleoside or nucleotide.

In particular embodiments the labelled nucleoside or nucleotide may be enzymatically incorporable and enzymatically extendable. Accordingly a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labelled with dyes of the invention may have the formula:

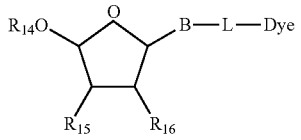

Where Dye is a dye compound according to the present invention, B is a nucleobase, such as, for example uracil, thymine, cytosine, adenine, guanine and the like and L is an optional linker group which may or may not be present. $R_{14}$ can be H, monophosphate, diphosphate, triphosphate, thiophosphate, a phosphate ester analog, 'O— attached to a reactive phosphorous containing group or —O— protected by a blocking group. $R_{15}$ can be H, OH, a phosphoramidite or a 3'OH blocking group and $R_{16}$ is H or OH.

Where $R_{15}$ is phosphoramidite, $R_{14}$ is an acid-cleavable hydroxyl protecting group which allows subsequent monomer coupling under automated synthesis conditions.

In a particular embodiment the blocking group is separate and independent of the dye compound, i.e. not attached to it.

In an alternative embodiment the dye may comprise all or part of the 3'OH blocking group. Thus $R_{15}$ can be a 3'OH blocking group which may or may not comprise the dye compound.

In still yet another alternative embodiment there is no blocking group on the 3' carbon of the pentose sugar and the dye (or dye and linker construct) attached to the base, for example, can be of a size or structure sufficient to act as a block to the incorporation of a further nucleotide from a point other than the 3' site. Thus the block can be due to steric hindrance or can be due to a combination of size, charge and structure.

The use of a blocking group allows polymerisation to be controlled, such as by stopping extension when a modified nucleotide is incorporated. If the blocking effect is reversible, for example by way of non-limiting example by changing chemical conditions or by removal of a chemical block, extension can be stopped at certain points and then allowed to continue.

In another particular embodiment a 3'OH blocking group will comprise moieties disclosed in WO2004/018497 (herein incorporated by reference) for example of the formula:

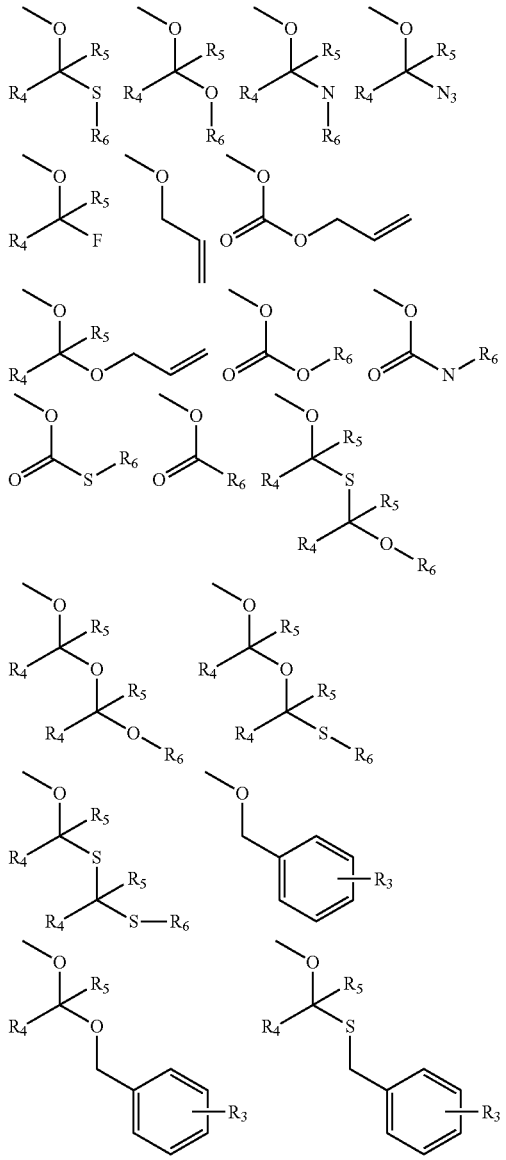

where $R_4$ is H or alkyl, $R_5$ is H or alkyl and $R_6$ is alkyl, cycloalkly, alkenyl, cycloalkenyl or benzyl In a particular embodiment the linker and blocking group are both present and are separate moieties which are both cleavable under substantially similar conditions. Thus deprotection and deblocking processes may be more efficient since only a single treatment will be required to remove both the dye compound and the block.

The invention also encompasses polynucleotides incorporating dye compounds according to the present invention. Such polynucleotides may be DNA or RNA comprised respectively of deoxyribonucleotides or ribonucleotides joined in phosphodiester linkage. Polynucleotides according to the invention may comprise naturally occurring nucleotides, non-naturally occurring (or modified) nucleotides other than the modified nucleotides of the invention or any combination thereof, provided that at least one modified nucleotide, i.e. labelled with a dye compound, according to the invention is present. Polynucleotides according to the invention may also include non-natural backbone linkages and/or non-nucleotide chemical modifications. Chimeric structures comprised of mixtures of ribonucleotides and deoxyribonucleotides comprising at least one modified nucleotide according to the invention are also contemplated.

Modified nucleotides (or nucleosides) comprising a dye compound according to the invention may be used in any method of analysis which requires detection of a fluorescent label attached to a nucleotide or nucleoside, whether on its own or incorporated into or associated with a larger molecular structure or conjugate. In this context the term "incorporated into a polynucleotide" requires that the 5' phosphate is joined in phosphodiester linkage to the 3' hydroxyl group of a second (modified or unmodified) nucleotide, which may itself form part of a longer polynucleotide chain. The 3' end of the modified nucleotide of the invention may or may not be joined in phosphodiester linkage to the 5' phosphate of a further (modified or unmodified) nucleotide. Thus, in one non-limiting embodiment the invention provides a method of detecting a modified nucleotide incorporated into a polynucleotide which comprises:

(a) incorporating at least one modified nucleotide according to the third aspect of the invention into a polynucleotide and (b) detecting the modified nucleotide(s) incorporated into the polynucleotide by detecting the fluorescent signal from the dye compound attached to said modified nucleotide(s).

This method requires two essential steps: a synthetic step (a) in which one or more modified nucleotides according to the invention are incorporated into a polynucleotide and a detection step (b) in which one or more modified nucleotide(s) incorporated into the polynucleotide are detected by detecting or quantitatively measuring their fluorescence.

In one embodiment of the invention the at least one modified nucleotide is incorporated into a polynucleotide in the synthetic step by the action of a polymerase enzyme. However, other methods of joining modified nucleotides to polynucleotides, such as for example chemical oligonucleotide synthesis or ligation of labelled oligonucleotides to unlabelled oligonucleotides, are not excluded. Therefore, in the specific context of this method of the invention, the term "incorporating" a nucleotide into a polynucleotide encompasses polynucleotide synthesis by chemical methods as well as enzymatic methods.

In a specific embodiment the synthetic step may comprise incubating a template polynucleotide strand with a reaction mixture comprising fluorescently labelled modified nucleotides of the invention and a polymerase under conditions which permit formation of a phosphodiester linkage between a free 3' hydroxyl group on a polynucleotide strand annealed to said template polynucleotide strand and a 5' phosphate group on said modified nucleotide. This embodiment comprises a synthetic step in which formation of a polynucleotide strand is directed by complementary base-pairing of nucleotides to a template strand.

In all embodiments of the method, the detection step may be carried out whilst the polynucleotide strand into which the modified nucleotides are incorporated is annealed to a template strand, or after a denaturation step in which the two strands are separated. Further steps, for example chemical or enzymatic reaction steps or purification steps, may be included between the synthetic step and the detection step. In particular, the target strand incorporating the modified nucleotide(s) may be isolated or purified and then processed further or used in a subsequent analysis. By way of example, target polynucleotides labelled with modified nucleotide(s) according to the invention in a synthetic step may be subsequently used as labelled probes or primers. In other embodiments the product of the synthetic step (a) may be subject to further reaction steps and, if desired, the product of these subsequent steps purified or isolated.

Suitable conditions for the synthetic step will be well known to those familiar with standard molecular biology techniques. In one embodiment the synthetic step may be analogous to a standard primer extension reaction using nucleotide precursors, including modified nucleotides according to the invention, to form an extended target strand complementary to the template strand in the presence of a suitable polymerase enzyme. In other embodiments the synthetic step may itself form part of an amplification reaction producing a labelled double stranded amplification product comprised of annealed complementary strands derived from copying of the target and template polynucleotide strands. Other exemplary "synthetic" steps include nick translation, strand displacement polymerisation, random primed DNA labelling etc. The polymerase enzyme used in the synthetic step must be capable of catalysing the incorporation of modified nucleotides according to the invention. Otherwise, the precise nature of the polymerase is not particularly limited but may depend upon the conditions of the synthetic reaction. By way of example, if the synthetic reaction is carried out using thermocycling then a thermostable polymerase is required, whereas this may not be essential for standard primer extension reactions. Suitable thermostable polymerases which are capable of incorporating the modified nucleotides according to the invention include those described in WO 2005/024010 or WO06120433.In synthetic reactions which are carried out at lower temperatures such as 37° C., polymerase enzymes need not necessarily be thermostable polymerases, therefore the choice of polymerase will depend on a number of factors such as reaction temperature, pH, strand-displacing activity and the like.

In specific non-limiting embodiments the invention encompasses use of the modified nucleotides or nucleosides labelled with dyes according to the invention in a method of nucleic acid sequencing, re-sequencing, whole genome sequencing, single nucleotide polymorphism scoring, any other application involving the detection of the modified nucleotide or nucleoside when incorporated into a polynucleotide, or any other application requiring the use of polynucleotides labelled with the modified nucleotides comprising fluorescent dyes according to the invention.

In a particular embodiment the invention provides use of modified nucleotides comprising dye compounds according to the invention in a polynucleotide "sequencing-by-synthesis" reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) is determined in a detection or "imaging" step. The identity of the added base may be determined after each nucleotide incorporation step. The sequence of the template may then be inferred using conventional Watson-Crick base-pairing rules. The use of the modified nucleotides labelled with dyes according to the invention for determination of the identity of a single base may be useful, for example, in the scoring of single nucleotide polymorphisms, and such single base extension reactions are within the scope of this invention.

In an embodiment of the invention, the sequence of a template polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide is primed with a suitable primer (or prepared as a hairpin construct which will contain the primer as part of the hairpin), and the nascent chain is extended in a stepwise manner by addition of nucleotides to the 3' end of the primer in a polymerase-catalysed reaction.

In particular embodiments each of the different nucleotide triphosphates (A, T, G and C) is labelled with a unique fluorophore and also comprises a blocking group at the 3' position to prevent uncontrolled polymerisation. The polymerase enzyme incorporates a nucleotide into the nascent chain complementary to the template polynucleotide, and the blocking group prevents further incorporation of nucleotides. Any unincorporated nucleotides are removed and the fluorescent signal from each incorporated nucleotide is "read" optically by suitable means, such as a charge-coupled device using laser excitation and suitable emission filters. The 3'-blocking group and fluorescent dye compounds are then removed (deprotected), particularly by the same chemical or enzymatic method, to expose the nascent chain for further nucleotide incorporation. Typically the identity of the incorporated nucleotide will be determined after each incorporation step but this is not strictly essential. Similarly, U.S. Pat. No. 5,302,509 discloses a method to sequence polynucleotides immobilised on a solid support. The method relies on the incorporation of fluorescently labelled, 3'-blocked nucleotides A, G, C and T into a growing strand complementary to the immobilised polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group which serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments sequencing may proceed by strand displacement. In certain embodiments a primer bearing the free 3' hydroxyl group may be added as a separate component (e.g. a short oligonucleotide) which hybridises to a single-stranded region of the template to be sequenced. Alternatively, the primer and the template strand to be sequenced may each form part of a partially self-complementary nucleic acid strand capable of forming an intramolecular duplex, such as for example a hairpin loop structure. Hairpin polynucleotides and methods by which they may be attached to solid supports are disclosed in applicant's co-pending International application publication nos. WO0157248 and WO 2005/047301. Nucleotides are added successively to the free 3'hydroxyl group, resulting in synthesis of a polynucleotide chain in the 5' to 3' direction. The nature of the base which has been added may be determined, particularly but not necessarily after each nucleotide addition, thus providing sequence information for the nucleic acid template. The term "incorporation" of a nucleotide into a nucleic acid strand (or polynucleotide) in this context refers to joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments the nucleic acid template to be sequenced may be attached to a solid support via any suitable linkage method known in the art, for example via covalent attachment. In certain embodiments template polynucleotides may be attached directly to a solid support (e.g. a silica-based support). However, in other embodiments of the invention the surface of the solid support may be modified in some way so as to allow either direct covalent attachment of template polynucleotides, or to immobilise the template polynucleotides through a hydrogel or polyelectrolyte multilayer, which may itself be non-covalently attached to the solid support.

Arrays in which polynucleotides have been directly attached to silica-based supports are those for example disclosed in WO00006770, wherein polynucleotides are immobilised on a glass support by reaction between a pendant epoxide group on the glass with an internal amino group on the polynucleotide. In addition, Applicants disclose in a copending International patent application publication number WO2005/047301 arrays of polynucleotides attached to a solid support, e.g. for use in the preparation of SMAs, by reaction of a sulphur-based nucleophile with the solid support. A still further example of solid-supported template polynucleotides is where the template polynucleotides are attached to hydrogel supported upon silica-based or other solid supports. Silica-based supports are typically used to support hydrogels and hydrogel arrays as described in W000/31148, W001/01143, W002/12566, W003/014392, U.S. Pat. No. 6,465,178 and W000/53812.

A particular surface to which template polynucleotides may be immobilised is a polyacrylamide hydrogel. Polyacrylamide hydrogels are described in the prior art, some of which is discussed above. However, a particular hydrogel is described in WO2005/065814.

DNA template molecules can be attached to beads or microparticles for the purposes of sequencing; for example as described in U.S. Pat. No. 6,172,218. Further examples of the preparation of bead libraries where each bead contains different DNA sequences can be found in the prior art (Nature. 437, 376-380 (2005); Science. 309, 5741, 1728-1732 (2005)). Sequencing of arrays of such beads using nucleotides as described is within the scope of the invention.

The template(s) to be sequenced may form part of an "array" on a solid support, in which case the array may take any convenient form. Thus, the method of the invention is applicable to all types of "high density" arrays, including single-molecule arrays, clustered arrays and bead arrays. Modified nucleotides labelled with dye compounds of the invention may be used for sequencing templates on essentially any type of array formed by immobilisation of nucleic acid molecules on a solid support, and more particularly any type of high-density array. However, the modified nucleotides labelled with dye compounds of the invention are particularly advantageous in the context of sequencing of clustered arrays.

In multi-polynucleotide or clustered arrays, distinct regions on the array comprise multiple polynucleotide template molecules. The term "clustered array" refers to an array wherein distinct regions or sites on the array comprise multiple polynucleotide molecules that are not individually resolvable by optical means. Depending on how the array is formed each site on the array may comprise multiple copies of one individual polynucleotide molecule or even multiple copies of a small number of different polynucleotide molecules (e.g. multiple copies of two complementary nucleic acid strands). Multi-polynucleotide or clustered arrays of nucleic acid molecules may be produced using techniques generally known in the art. By way of example, WO 98/44151 and WO00/18957 both describe methods of amplification of nucleic acids wherein both the template and amplification products remain immobilised on a solid support in order to form arrays comprised of clusters or "colonies" of immobilised nucleic acid molecules. The nucleic acid molecules present on the clustered arrays prepared according to these methods are suitable templates for sequencing using the modified nucleotides labelled with dye compounds of the invention.

The modified nucleotides labelled with dye compounds of the invention are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to effect individual resolution of the polynucleotides. The target nucleic acid molecules immobilised onto the surface of the solid support should thus be capable of being resolved by optical means. This means that, within the resolvable area of the particular imaging device used, there must be one or more distinct signals, each representing one polynucleotide.

This may be achieved wherein the spacing between adjacent polynucleotide molecules on the array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualised, it is possible to distinguish one molecule on the array from its neighbouring molecules. Separation between individual molecules on the array will be determined, in part, by the particular technique used to resolve the individual molecules. The general features of single molecule arrays will be understood by reference to published applications WO00/06770 and WO 01/57248. Although one use of the modified nucleotides of the invention is in sequencing-by-synthesis reactions, the utility of the modified nucleotides is not limited to such methods. In fact, the nucleotides may be used advantageously in any sequencing methodology which requires detection of fluorescent labels attached to nucleotides incorporated into a polynucleotide.

In particular, the modified nucleotides labelled with dye compounds of the invention may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labelled dideoxynucleotides in a primer extension sequencing reaction. So called Sanger sequencing methods, and related protocols (Sanger-type), rely upon randomised chain termination with labelled dideoxynucleotides.

Thus, the invention also encompasses modified nucleotides labelled with dye compounds according to the invention which are dideoxynucleotides lacking hydroxyl groups at both of the 3' and 2' positions, such modified dideoxynucleotides being suitable for use in Sanger type sequencing methods and the like.

Modified nucleotides labelled with dye compounds of the present invention incorporating 3' blocking groups, it will be recognized, may also be of utility in Sanger methods and related protocols since the same effect achieved by using modified dideoxy nucleotides may be achieved by using modified nucleotides having 3'-OH blocking groups: both prevent incorporation of subsequent nucleotides. Where nucleotides according to the present invention, and having a 3' blocking group are to be used in Sanger-type sequencing methods it will be appreciated that the dye compounds or detectable labels attached to the nucleotides need not be connected via cleavable linkers, since in each instance where a labelled nucleotide of the invention is incorporated; no nucleotides need to be subsequently incorporated and thus the label need not be removed from the nucleotide.

The invention also provides kits including modified nucleosides and/or nucleotides labelled with dyes according to the invention. Such kits will generally include at least one modified nucleotide or nucleoside labelled with a dye according to the invention together with at least one further component. The further component(s) may be further modified or unmodified nucleotides or nucleosides. For example, modified nucleotides labelled with dyes according to the invention may be supplied in combination with unlabelled or native nucleotides, and/or with fluorescently labelled nucleotides or any combination thereof. Accordingly the kits may comprise modified nucleotides labelled with dyes according to the invention and modified nucleotides labelled with other, for example, prior art dye compounds. Combinations of nucleotides may be provided as separate individual components or as nucleotide mixtures.

Where kits comprise a plurality, particularly two, more particularly four, modified nucleotides labelled with a dye compound, the different nucleotides may be labelled with different dye compounds. Where the different nucleotides are labelled with different dye compounds it is a feature of the kits that said dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary based DNA sequencing platform) when two or more such dyes are present in one sample. When two modified nucleotides labelled with fluorescent dye compounds are supplied in kit form, it is a feature of the invention that the spectrally distinguishable fluorescent dyes can be excited at the same wavelength, such as, for example by the same laser. When four modified nucleotides labelled with fluorescent dye compounds are supplied in kit form, it is a feature of the invention that two of the spectrally distinguishable fluorescent dyes can both be excited at one wavelength and the other two spectrally distinguishable dyes can both be excited at another wavelength. Particular excitation wavelengths are 532 nm, 630 nm to 700 nm, particularly 660 nm.

In one embodiment a kit comprises a modified nucleotide labelled with 'DYE 2' and a second modified nucleotide labelled with a second dye wherein the dyes have a difference in absorbance maximum of at least 10 nm, particularly 20 nm is to 50 nm. More particularly the two dye compounds have Stokes shifts of between 15-40 nm where "Stokes shift" is the distance between the peak absorption and peak emission wavelengths. Particularly the modified nucleotides are labelled with 'Dye 1' and 'Dye 2'. Yet more particularly the modified nucleotides are labelled with 'Dye 2' and an alternative dye that excites at 532 nm (such as Atto 532 (Atto-tec catalogue number AD532-3), as described in WO 04055117; or Alexa 532 (Molecular Probes catalogue number A20001, patent U.S. Pat. No. 6,130,101).

In a further embodiment said kit further comprises two other modified nucleotides labelled with fluorescent dyes wherein said dyes are excited by the same laser at 600 nm to 700 nm, particularly 630 nm to 700 nm, more particularly 660 nm. Wherein the dyes have a difference in absorbance maximum of at least 10 nm, particularly 20 nm to 50 nm. More particularly the two dye compounds have Stokes shifts of between 20-40 nm. Still yet more particularly the two dye compounds have a different absorbance maximum above 600 nm, particularly above 640 nm. Particular dyes which are spectrally distinguishable from 'DYE 1' and 'DYE 2' and which meet the above criteria are polymethine analogues as described in U.S. Pat. No. 5,268,486 (for example Cy5) or WO 0226891 (Alexa 647; Molecular Probes A20106) or unsymmetrical polymethines as disclosed in U.S. Pat. No. 6,924,372.Thus, in a particular embodiment the invention provides a set of four nucleotides (A, C, G and T) each labelled with one of the following spectrally distinguishable fluorescent dye compounds: 'Dye 2', atto 532, a dicarbocyanine (Cy5) analogue such as Ferrania S-07181, and Dy681 (U.S. Pat. No. 6,924,372). Another particular embodiment of so the invention provides a set of four nucleotides (A, C, G and T) each labelled with one of the following spectrally distinguishable dye compounds: 'DYE 2', 'DYE 1', a dicarbocyanines such as Ferrania S-07181, and Dy 681. Yet more particularly the set of four nucleotides further each comprise a 3'OH blocking group. Still yet more particularly both the dye compound and the 3'OH group are removable under the same reaction conditions. Synthesis of an exemplary set of four dye-nucleotide structures is given in the examples section below.

The Dyomics compound Dy681 can be substituted by a number of commercially available, structurally similar analogues also detailed in U.S. Pat. No. 6,924,372. For example dyes such as Dy675, Dy676, Dy677, Dy680, Dy682, Dy700, Dy701 (also available from Dyomics) may also be used.

The pentamethine cyanine analogue used (S-07181) contains a sulphonamide moiety on the aromatic ring, and can be obtained from Ferrania Imaging technologies (Italy). This-material can be substituted with a number of other commercially available materials that have a spectral similarity, for example Cy5 (GE Healthcare; PA15100), Alexa 647 (Molecular Probes; A20106), Atto 647 (Atto-tec; AD647-3), Dy647, Dy648, Dy650, Dy651 or Dy652 (Dyomics).

In other embodiments the kits may include a polymerase enzyme capable of catalyzing incorporation of the modified nucleotides into a polynucleotide. Other components to be included in such kits may include buffers and the like. The modified nucleotides labelled with dyes according to the invention, and other any nucleotide components including mixtures of different nucleotides, may be provided in the kit in a concentrated form to be diluted prior to use. In such embodiments a suitable dilution buffer may also be included.

It is noted that, as used in this specification and the appended claims, the singular forms "a", "an" and "the" include plural referents unless expressly and unequivocally limited to one referent. It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

EXAMPLE

Experimental Overview

The following experimental details describe the complete exposition of one embodiment of the invention as described above.

Example 1

Preparation of 'Dye 1'

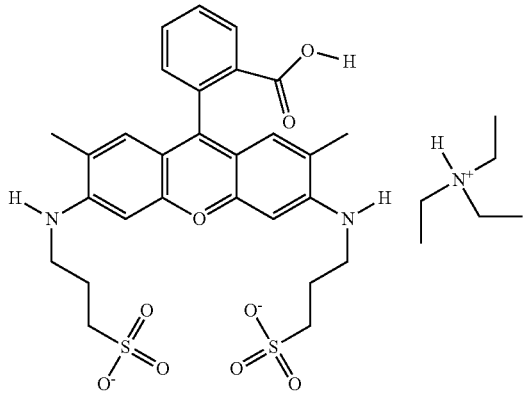

Dye 1

Step 1

Synthesis of Triethylammonio 3-[(5-hydroxy-2-methyl-phenyl)amino]propanesulfonate

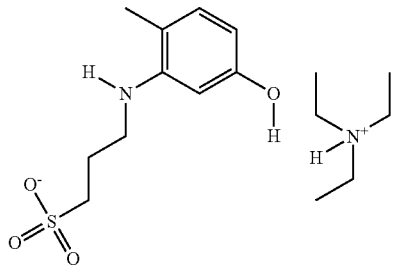

Mixture of 12.3 g (0.1 mol) 3-amino-4-methylphenol, 15 g (1.1 mol) 1,3-propanesultone and 50 ml methanol was stirred for 48 hours. The methanol was evaporated in vacuum, white solid mass triturated with diethyl ether and filtered off. This 3-[(5-hydroxy-2-methyl-phenyl)amino] propanesulfonate suspended in 50 ml of acetone, 10 ml triethylamine was added and mixture stirred overnight. Product filtered off, washed with diethyl ether. Yield 21 g (60.7%)

Proton NMR (PMR) ($CD_3OD$): 6.97 (1H, d), 6.36 (1H, d), 6.24 (1H, dd), 3.47 (2H, t), 3.37 (6H, q), 3.08 (2H, t), 2.27 (2H, dt), 2.22 (3H, s), 1.47 (9H, t).

Step 2

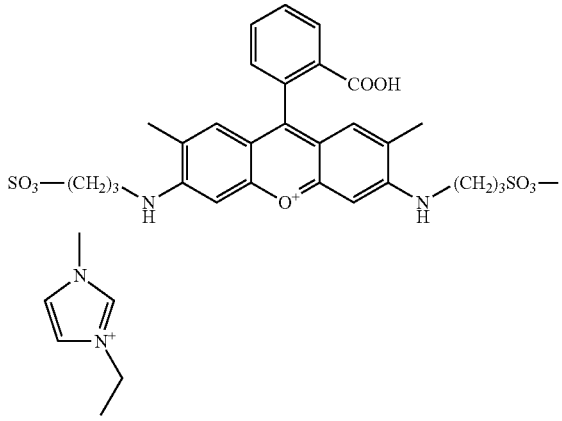

The reaction was performed according to Example 2; step 3 using triethylammonium 3-[(5-hydroxy-2-methyl-phenyl) amino]propanesulfonate instead of triethylammonium 3-(7-hydroxy-3,4-dihydro-quinoline-1-yl)-propanesulfonate. The reaction mixture was cooled to room temperature, solid mass treated with acetonitrile and the product was filtered off then under vacuum to give quantitative yield of DYE 1 as a purple powder.

PMR (CD3OD): 8.83 (1H, s), 8.13 (1H, d), 7.64 (2H, m), 7.55 (1H, s), 7.50 (1H, s), 7.22 (1H, d), 6.89 (1H, s), 6.86 (1H, s), 4.15 (2H, k), 3.81 (3H, s), 3.54 (4H, t), 2.86 (4H, m), 2.11 (4H, t), 2.06 (6H, s), 1.42 (3H, t).

Coupling of 'Dye 1' with t-butyl ester isonipecotic acid hydrochloride

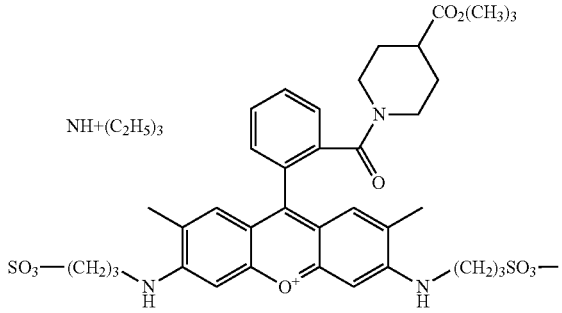

Mixture of 100 mg of dye from step 2, 2 ml of dry DMF, 0.5 ml N-ethyl-N,N-diisopropylamine and 80 mg BOP was stirred at room temperature for 20 min. then 80 mg t-butyl ester isonipecotic acid hydrochloride was added and stirring was continued for 4 h.

DMF removed in vacuum and residue purified by flash column ($CH_3CN$—$H_2O$).

Removal of Ester.

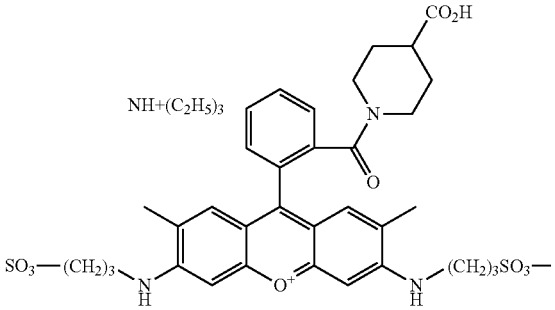

Mixture of the dye from previous step, 2 ml dry methylene chloride and 2 ml trifluoroacetic acid was stirred at room temperature for 2 hours.

Methylene chloride and trifluoroacetic acid removed in vacuum. Methanol (2 ml) and triethylamine (0.5 ml) added to residue then solvents removed in vacuum again. In some cases pre-purification using ion-exchange resin may be useful. Absorption max. 525 nm.

Dye purified by HPLC

Structure was confirmed by NMR.

Coupling of 'Dye 1' with t-butyl ester N-methylaminoacetic acid hydrochloride

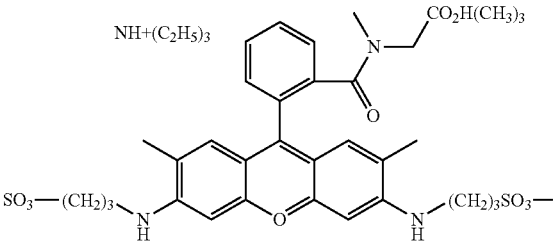

Mixture of 100 mg of dye from step 2, 2 ml of dry DMF, 0.5 ml N-ethyl-N,N-diisopropylamine and 80 mg BOP was stirred at room temperature for 20 min. then 80 mg t-butyl ester N-methylaminoacetic acid hydrochloride was added and stirring was continued for 4 h.

DMF removed in vacuum and residue purified by flash column ($CH_3CN$—$H_2O$).

Removal of Ester.

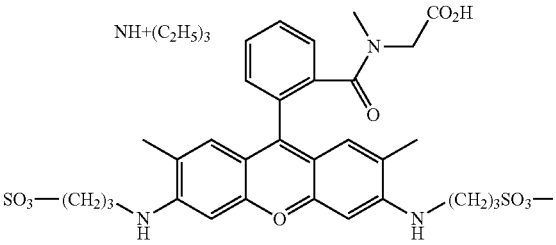

Mixture of the dye from previous step, 2 ml dry methylene chloride and 2 ml trifluoroacetic acid was stirred at room temperature for 2 hours.

Methylene chloride and trifluoroacetic acid removed in vacuum. Methanol (2 ml) and triethylamine (0.5 ml) added to residue then solvents removed in vacuum again. In some cases pre-purification using ion-exchange resin may be useful.

Dye purified by HPLC

Structure was confirmed by NMR.

Coupling of 'Dye 1' with N-methylaminobutyric acid

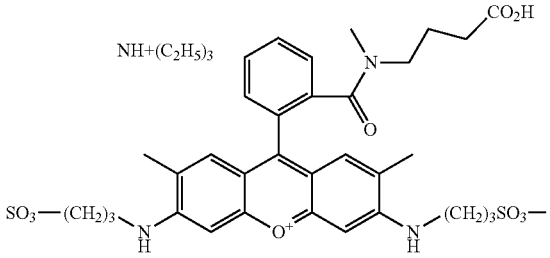

Mixture of 100 mg of dye from step 2, 2 ml of dry DMF, 0.5 ml N-ethyl-N,N-diisopropylamine and 80 mg BOP was stirred at room temperature for 20 min. then 80 mg N-methylaminobutyric acid and stirring was continued for 4 h.

DMF removed in vacuum and residue purified by flash column ($CH_3CN$—$H_2O$).

Example 2

Preparation of 'Dye 2'

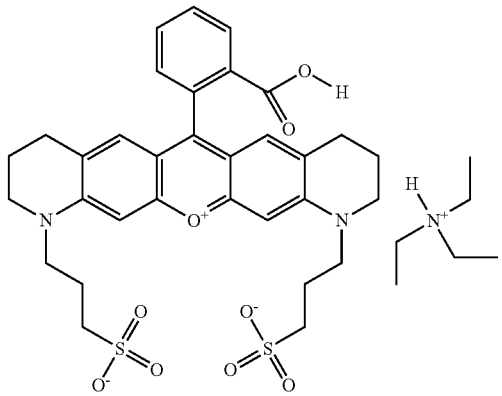

Dye 2

Step 1

Synthesis of 3-(7-Hydroxyquinolinio-1-yl)propanesulfonate

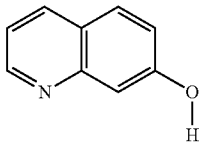

Molecular Weight = 145.16
Molecular Formula = C9H7NO

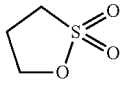

Molecular Weight = 122.14
Molecular Formula = C3H6O3S

-continued

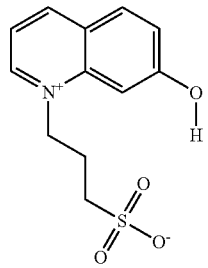

Molecular Weight = 267.31
Molecular Formula = C12H13NO4S

This compound is prepared from 7-hydroxyquinoline and 1,3-propanesultone as published (GB 1,122,704) for 3-(8-hydroxyquinolinio-1-yl)propanesulfonate.

Step 2

Synthesis of Triethylammonium 3-(7-hydroxy-3,4-dihydro-quinoline-1-yl)propanesulfonate

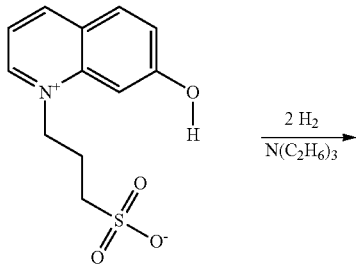

Molecular Weight = 267.31
Molecular Formula = C12H13NO4S

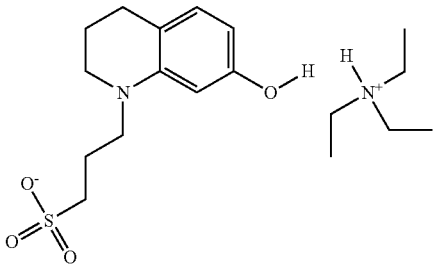

Molecular Weight = 270.33 102.20 = 372.53
Molecular Formula = C12H16NO4S•C6H16N

To a suspension of 2.67 g (10 mmole) of 3-(7-hydroxy-quinolinio-1-yl)propanesulfonate in 500 ml of methanol, 1.5 g of triethylamine was added and stirred 3-5 min until clear solution was prepared. To this solution 0.5 g Ni Raney was added and mixture hydrogenated at room temperature for 3 hours. The reaction mixture was suction filtered through diatomaceous earth and the filtrate evaporated under reduced pressure. The resulting crystallized yellow compound washed with diethyl ether and filtered off. Yield 3.7 g (99%).

The structure was confirmed by PMR ($CD_3OD$): 6.69 (1H, d), 6.14 (1H, d), 5.97 (1H, dd), 3.38 (2H, t), (2H, t), 3.20 (6H, q), 2.87 (2H, t), 2.65 (2H, t), (2H, t), 1.90 (2H, t), 1.31 (9H, t).

Step 3

Synthesis of 9-(2-Carboxyphenyl)xanthylium dye (DYE 2)

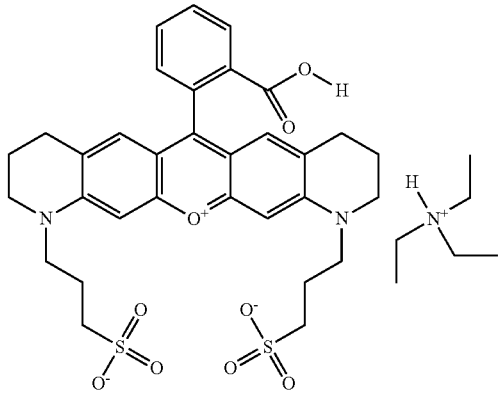

Molecular Weight = 653.76 102.20 = 755.98
Molecular Formula = C32H33N2O9S2•C6H16N The product of step two (0.05 g, 0.13 mmole) was combined with 0.05 g (0.34 mmole) of phthalic anhydride, 0.3 ml 1-ethyl-3-methylimidazolium chloride (ionic liquid) and 0.02 g of anhydrous $ZnCl_2$. The resulting mixture was heated in an oil bath at 140° C. for 3 hours and then cooled to room temperature. The resultant solid mass was treated with acetonitrile and the product was filtered off under vacuum to give quantitative yield (0.06 g) of (DYE 2) as a purple powder. Absorption max. 560 nm.

Structure was confirmed by PMR ($CD_3OD$): 8.26 (1H, d), 7.64 (1H, t), 7.54 (1H, t), 7.32 (1H, d), 7.04 (2H, s), 6.84 (2H, s), 3.77 (4H, m), 3.61 (4H, m), 2.97 (4H, m), 2.71 (4H, t), 2.21 (4H, t), 1.95 (4H, t).

By suspension of this product and 20 mg sodium acetate in ethanol, a sodium salt of this dye was prepared with quantitative yield.

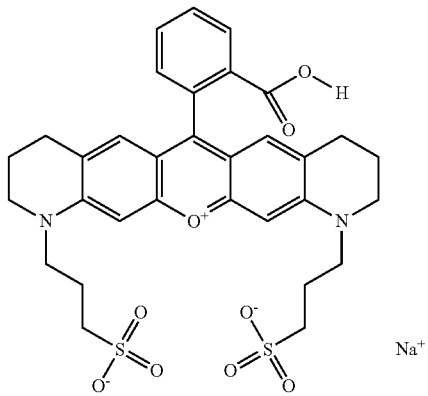

Molecular Weight = 653.76 22.99
Molecular Formula = C32H33N2O9S2•Na

Step 4a
Attachment of Carboxyfunctional-Linker Arm

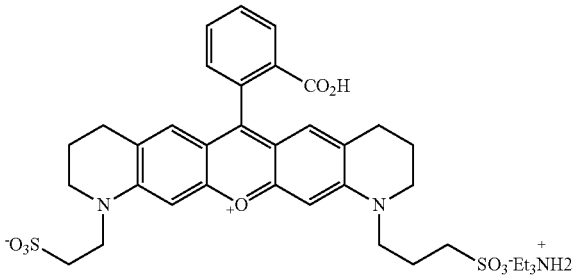

(I)

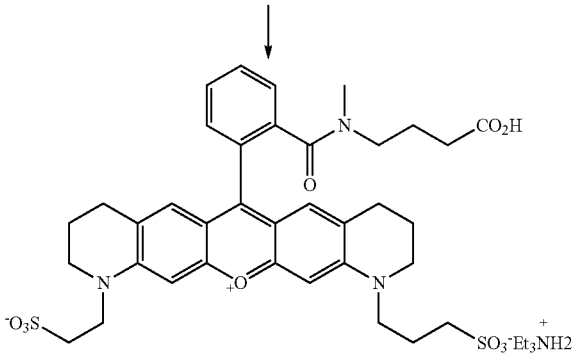

(II)

A solution of (benzotriazol-1-yloxy)tripyrrolidinophosphonium hexafluorophosphate (93 mg, 178 μmol) in DMF (0.5 ml) was added dropwise at room temperature to a stirred solution of the 'dye 2' from step 3 (89 μmol) and triethylamine (89 mg, 890 μmol) in DMF (30 ml) under nitrogen. After 70 min a solution of the Methyl N-Methyl-4-aminobutanoate hydrochloride (75 mg, 445 μmol) in DMF (0.5 ml) was added dropwise and left to stir for 18 h. The reaction mixture was cooled to 5° C. and a solution of 0.1 M sodium hydroxide (20 ml) was added dropwise. After 48 h the reaction mixture was concentrated in vacuum to remove solvents and purified on an Agilent Zorbax SB-C18 21.2×250 mm preparative HPLC. This gave 34.9 μmol of desired product. λ (max) 570 nm (EtOH), MS (ESP—) 752.

Step 4b
Attachment of Aminofunctional-Linker Arm

9-[2-(Piperazin-1-yl)carbonyl)phenyl]xanthylium dye 2

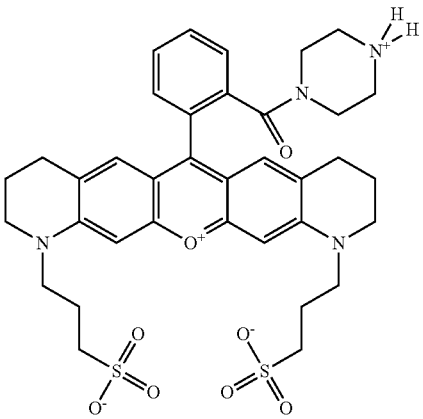

Molecular Weight = 722.89
Molecular Formula = C36H42N4O8S2

A mixture of 20 mg (0.35 mMol) 9-(2-Carboxyphenyl) xanthylium dye (Dye 2), 2 ml DMF, 0.5 ml triethylamine and 20 mg TMBU hexafluorophosphate was stirred at room temperature 20 minutes. Reaction was quenched with solution 0.05 g piperazine in 1 ml DMF and DMF evaporated in vacuum. Mixture diluted with ether and product filtered off. Yield of the dye as a purple powder 15 mg (78%). Absorption max. 564 nm.

Example 3

9-(2,4-Dicarboxyphenyl)- and
9-(2,5-Dicarboxyphenyl)xanthylium dye 3a,b

Dye 3a, b

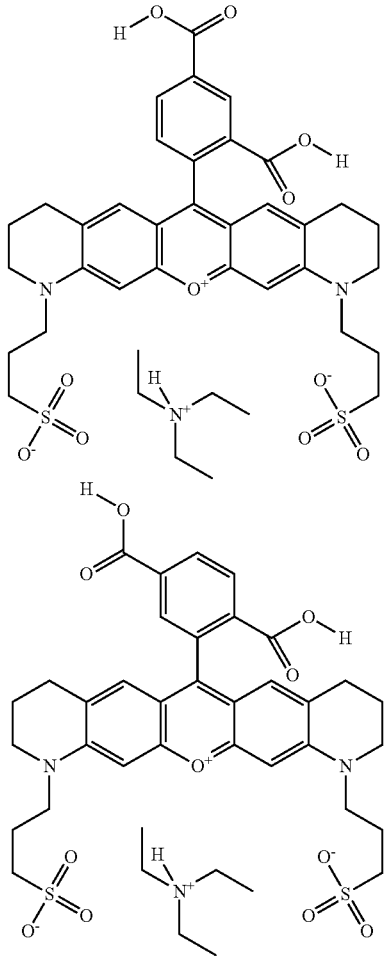

Molecular Weight = 697.77 102.20
Molecular Formula = C33H33N2O11S2, C6H16N

Triethylammonium 3-(7-hydroxy-3,4-2H-dihydro-quinoline-1-yl)sulfonate (Example 2, step 2) (0.05 g, 0.13 mmole) was combined with 0.05 g (0.26 mmole) of trimellitic anhydride in 0.5 ml of 1-ethyl-3-methylimidazolium chloride and 0.05 g of anhydrous $ZnCl_2$. The resulting mixture was heated at 120° C. for 0.5 hour then 5 ml of acetonitrile was added to the reaction mixture. The resulting precipitate is filtered, washed with acetonitrile and dried. Yield: 0.05 g. (92%). Isomers separated by HPLC and structure confirmed by NMR and mass-spectra Example 4

Step 1

9-(2-Carboxy-sulfophenyl)xanthylium dyes 4A,B,C

Dye 4A, B, C

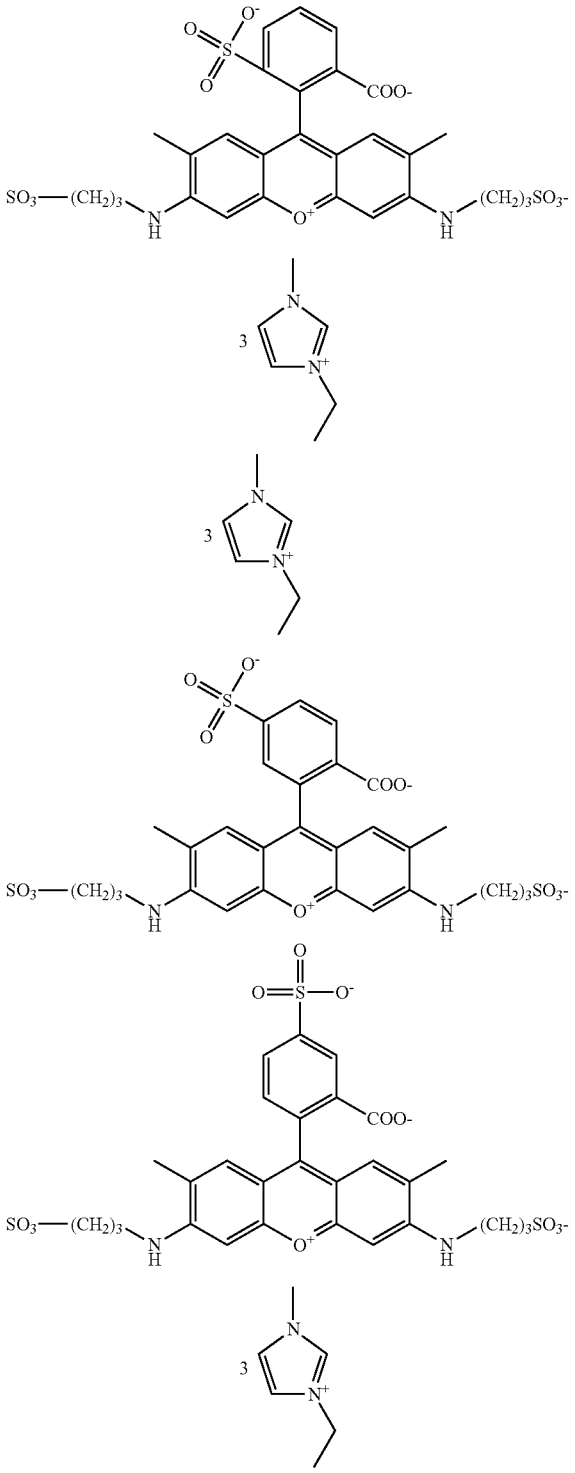

Triethylammonium 3-(3-sulfonatopropyl)amino-4-methylphenol (0.7 g, 2 mmole) was combined with solution of 0.5 g (~mmole) of sulfophthalic anhydride in 1 g 1-ethyl-3-methylimidazolium chloride (IL=ionic liquid) and 1 g of anhydrous $ZnCl_2$. The resulting mixture was heated 4 hours at 180° C. The reaction mixture was cooled to room temperature, solid mass treated with mixture acetonitrile-water and applied to a flash column. Dyes prepared as a purple powder.

TLC: $CH_3CN—H_2O$ 9:1.

Yield ~10%.

Step 2

Coupling with t-butyl ester isonipecotic acid hydrochloride

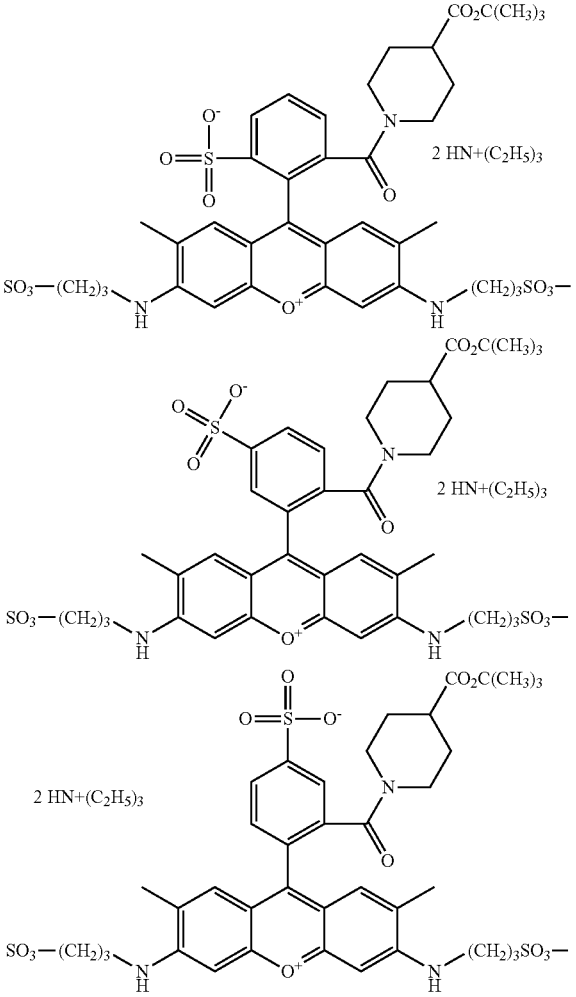

Mixture of 100 mg appropriate dye from previous step, 2 ml dry DMF, 0.5 ml N-ethyl-N,N-diisopropylamine and 80 mg BOP was stirred at room temperature for 20 min. then 80 mg t-butyl ester isonipecotic acid hydrochloride was added and stirring was continued for 4 h.

DMF removed in vacuum and residue purified by flash column ($CH_3CN—H_2O$).

Step 3

Deprotection.

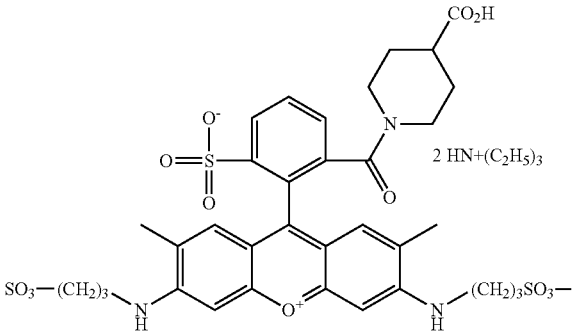

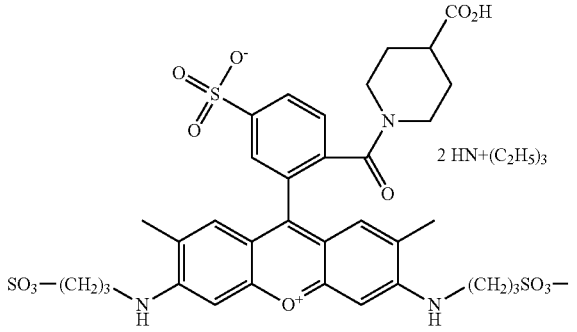

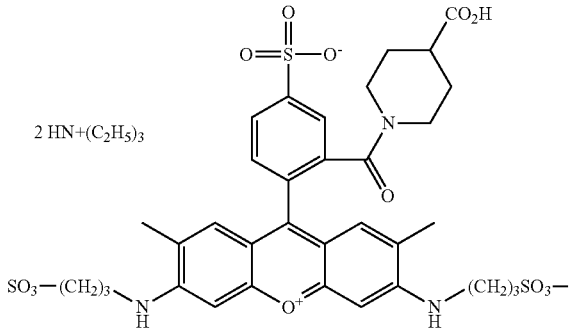

Mixture of appropriate dye from previous step, 2 ml dry methylene chloride and 2 ml trifluoroacetic acid was stirred at room temperature for 2 hours.

Methylene chloride and trifluoroacetic acid removed in vacuum. Methanol (2 ml) and triethylamine (0.5 ml) added to residue then solvents removed in vacuum again. In some cases pre-purification using ion-exchange resin may be useful.

Dyes purified by HPLC. Absorption max. 525 nm.

Structure was confirmed by NMR.

Example 5

Step 1.

9-(2-Carboxy-sulfonatophenyl)xanthylium dyes Dye 5a,b,c

Dye 5A, B, C

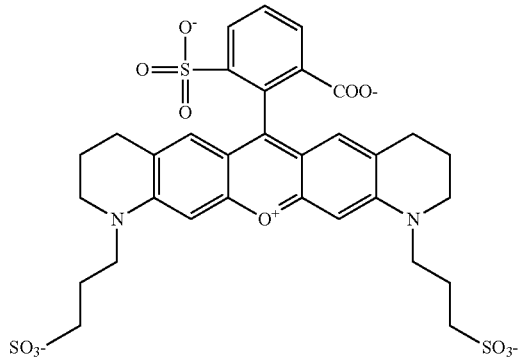

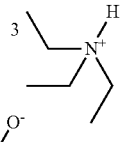

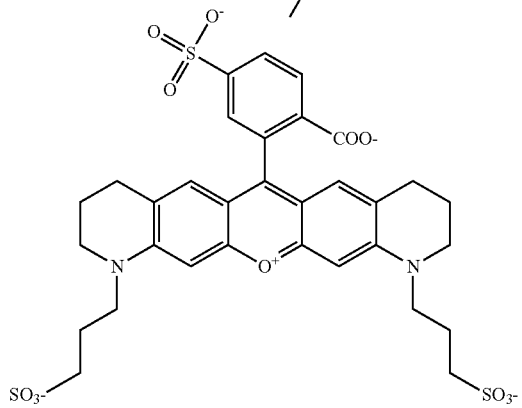

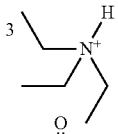

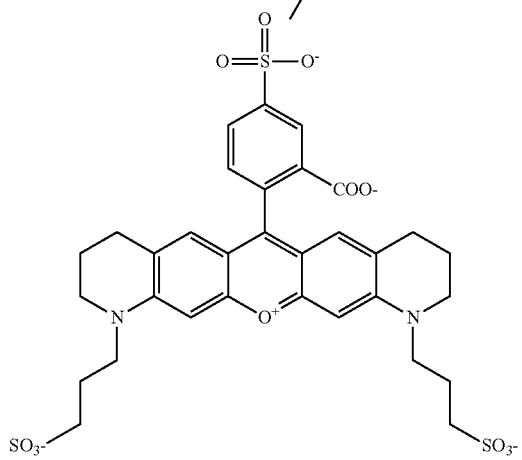

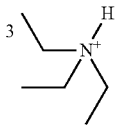

Triethylammonio 3-(7-hydroxy-3,4-dihydro-2H-quinoline-1-yl)propanesulfonate (0.74 g, 2 mmole) was combined with solution of 0.5 g (~2 mmole) of 3- or 4-sulfophthalic anhydride in 1 g 1-ethyl-3-methylimidazolium chloride and 1 g of anhydrous $ZnCl_2$. The resulting mixture was heated 4 hours at 180° C. The reaction mixture was cooled to room temperature, solid mass treated with mixture acetonitrile-water and applied to a flash column. Dyes prepared as a purple powder.

TLC: $CH_3CN—H_2O$ 9:1.

Yield ~20%.

Step 2

Coupling with t-butyl ester isonipecotic acid hydrochloride

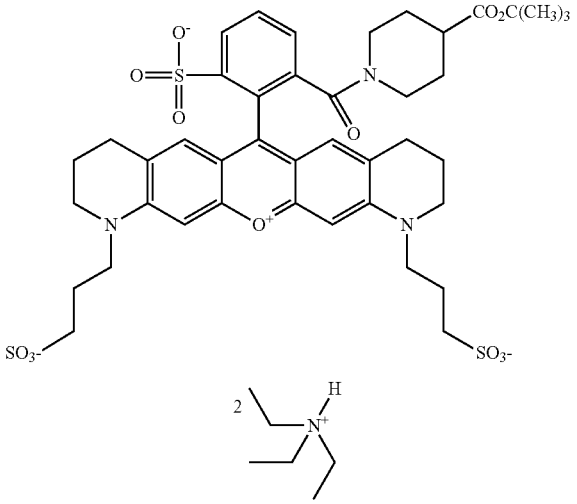

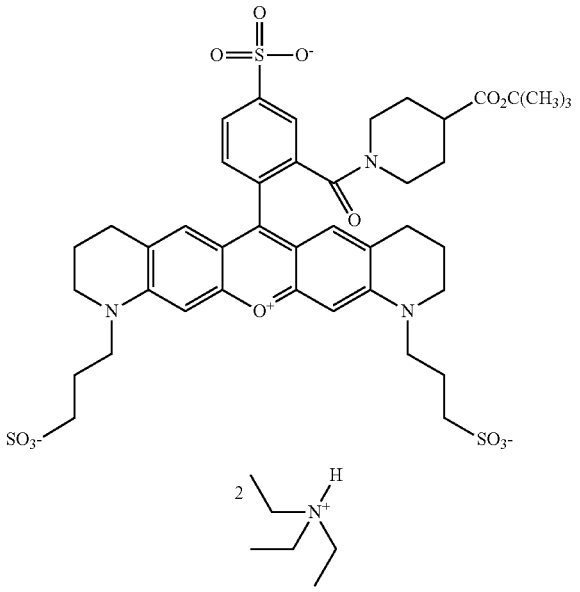

Mixture of 100 mg appropriate dye from previous step, 2 ml dry DMF, 0.5 ml N-ethyl-N,N-diisopropylamine and 80 mg BOP was stirred at room temperature for 20 min. then 80 mg t-butyl ester isonipecotic acid hydrochloride was added and stirring was continued for 4 h.

DMF removed in vacuum and residue purified by flash column ($CH_3CN—H_2O$).

Step 3

Deprotection.

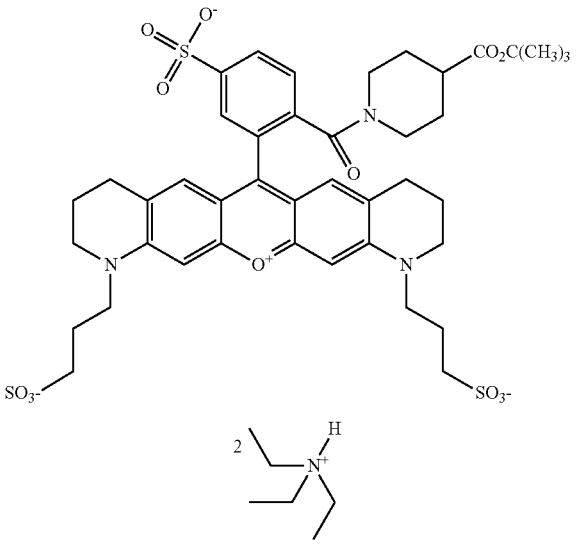

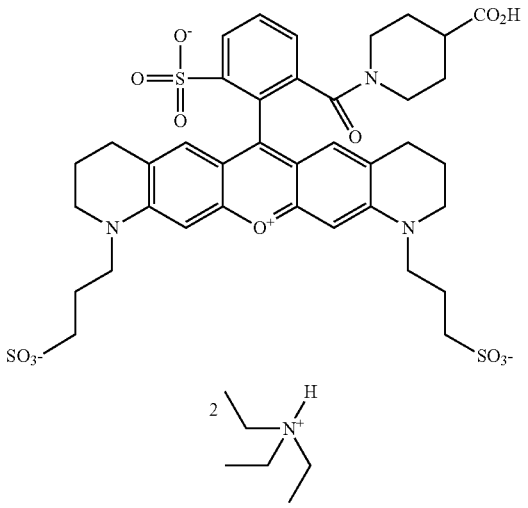

-continued

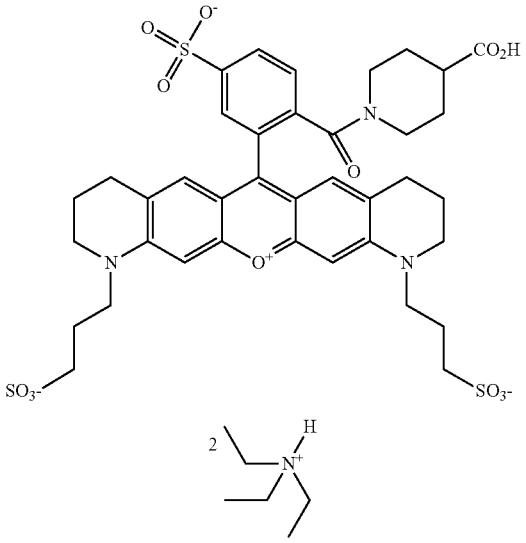

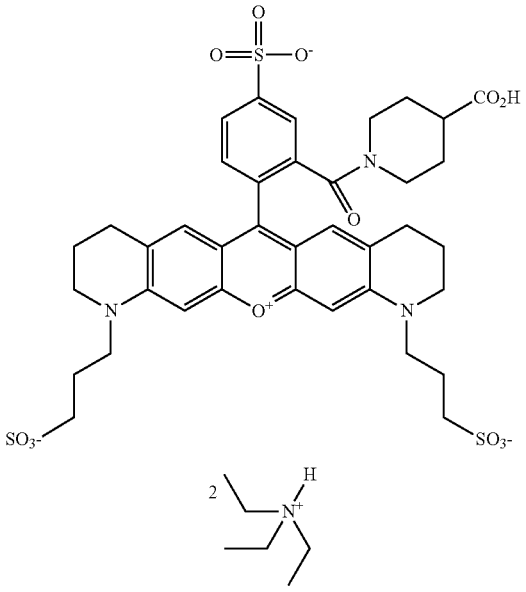

Mixture of appropriate dye from previous step, 2 ml dry methylene chloride and 2 ml trifluoroacetic acid was stirred at room temperature for 2 hours.

Methylene chloride and trifluoroacetic acid removed in vacuum. Methanol (2 ml) and triethylamine (0.5 ml) added to residue then solvents removed in vacuum again. In some cases pre-purification using ion-exchange resin may be useful.

Dyes purified by HPCL

Structure was confirmed by NMR.

Example 6

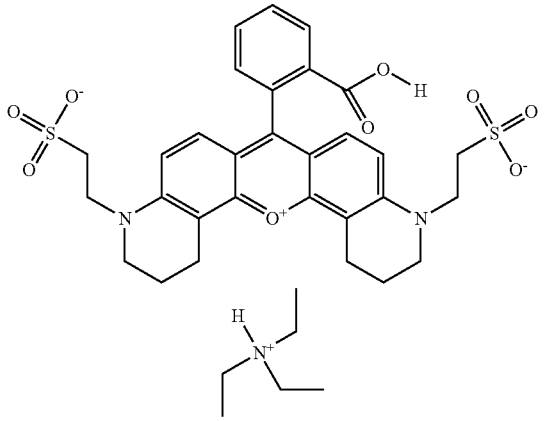

Dye 6

Step 1a 3-(5-Hydroxy-3,4-dihydro-2H-quinoline-1-yl)propanesulfonic acid

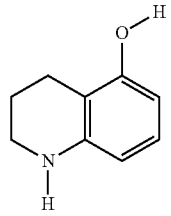

Molecular Weight = 149.19
Molecular Formula = C9H11NO

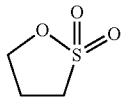

Molecular Weight = 122.14
Molecular Formula = C3H6O3S

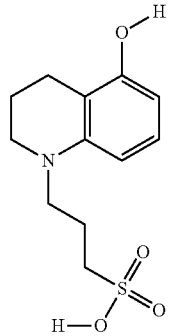

Molecular Weight = 271.34
Molecular Formula = C12H17NO4S

A mixture of 0.8 g (5.36 mmol) of 5-hydroxy-1,2,3,4-tetrahydroquinoline and 0.5 g 1,3-propanesultone (4.1 mmol) in 12 ml of butyronitrile was heated at 125° C. for hours. The mixture was suction filtered and the filtrate evaporated under reduced pressure. The resulting off white compound crystallized. Product washed with ethyl ether and filtered of. Yield 0.8 g (80%)

Structure and purity confirmed by NMR.

Step 1b.

Triethylammonium 3-(5-hydroxy-3,4-2H-dihydro-quinoline-1-yl)sulfonate

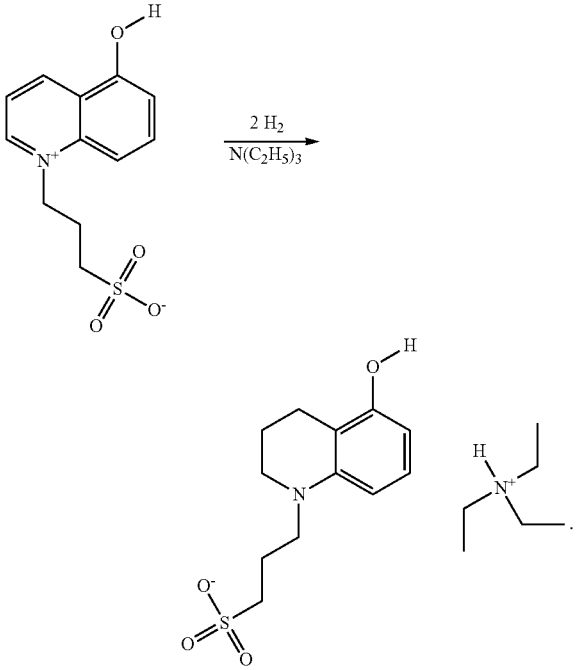

To a suspension of 5.3 g (20 mmol) of 3-(5-hydroxyquinolinio-1-yl)propanesulfonate in 200 ml of methanol, 3 ml of triethylamine was added and stirred 3-5 min until clear solution was prepared. To this solution 0.5 g Ni Raney added and mixture hydrogenated at room temperature for 3 hours. Reaction mixture was suction filtered through diatomaceous earth and the filtrate evaporated under reduced pressure. The resulting crystallized yellow compound washed with diethyl ether and filtered off. Yield 5 g (68%).

Structure and purity confirmed by NMR.

Step 2

9-(2-Carboxyphenyl)xanthylium dye 6

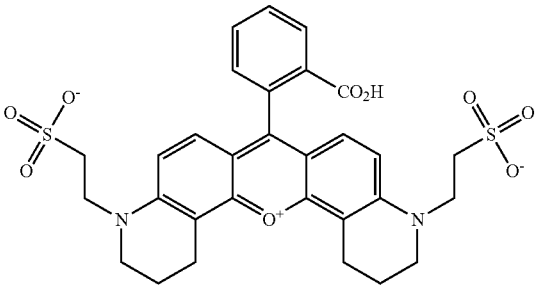

-continued

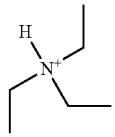

Dye 6

The product from previous step (0.7 g, 1.88 mmol) was combined with 0.2 g (1.35 mmol) of phthalic anhydride, 1 ml 1-ethyl-3-methylimidazolium chloride (ionic liquid) and 0.5 g of anhydrous $ZnCl_2$. The resulting mixture was heated at 180° C. for 2 hours. The reaction mixture was cooled to room temperature, solid mass treated with ethanol and the product was filtered off. Yield 1 gas a purple powder. Absorption max. 570 nm.

Structure was confirmed by NMR:

Example 7

9-(2,4-Dicarboxyphenyl)- and 9-(2,5-Dicarboxyphenyl)xanthylium dye 7A, B

Dye 7A, B

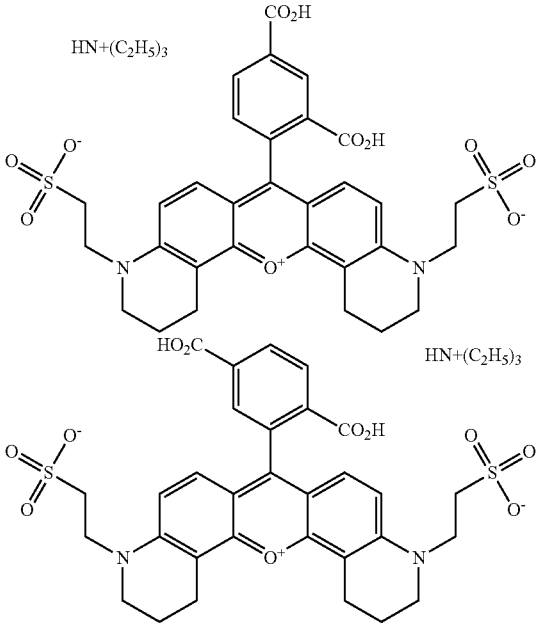

3-(5-Hydroxy-3,4-dihydro-2H-quinoline-1-yl)propanesulfonic acid triethylamonium salt from step la example 6 (0.025 g, 0.9 mmole) was combined with 0.02 g (0.10 mmole) of trimellitic anhydride and 0.03 g of anhydrous $ZnCl_2$. The resulting mixture was heated in an oil bath at 170° C. for 1 hours. The reaction mixture was cooled to room temperature, solid mass pulverized with acetonitrile and the product was filtered off The crude product was purified on silica gel. Yield: 0.005 g. (16%).

Mixture of isomers was separated by HPLC

Structure was confirmed by NMR.

Example 8

Synthesis of Azide linker (LN3):

Step 1

3-([1,3]Dioxolan-2-ylmethoxy)-benzoic acid ethyl ester

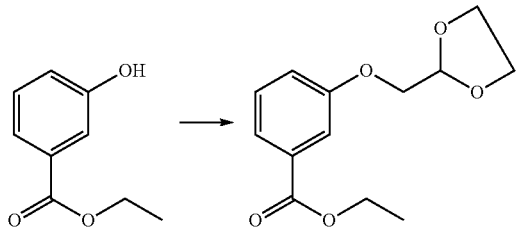

2-Bromomethyl-1,3-dioxolane (8.3 ml, 80 mmol), ethyl-3-hydroxy-benzoate (3.32 g, 20 mmol), potassium carbonate (5.53 g, 40 mmol) and sodium iodide (1.2 g, 8 mmol) were heated at 120° C. in DMF (8 ml) for 17 hrs. The reaction was cooled to room temperature and all the solvents were evaporated under reduced pressure. The residues were partitioned between DCM (250 ml) and water (250 ml). The DCM layer was separated and the aqueous layer was back-extracted with DCM (2×100 ml). All the DCM extracts were combined, dried over $MgSO_4$ and evaporated under reduced pressure.

The residue was purified by column chromatography (4×25 cm). The product was eluted with 20% petroleum ether (60-80° C.) in DCM and the title compound was obtained as a slightly brown oil (4.63 g, 91.8%). APCI-MS, m/z 252.95 (M+1).

$^1$HNMR [CDC1$_3$]: 1.39 (3H, $CH_3$, t, J 7.2), 3.96-4.09 (6H, $OCH_2CH_2O$, $ArOCH_2$, m), 4.36 (2H, $OCH_2$, q, J 7.2), 5.31 (1H, CH, t, J 4.0), 7.14 (1H, Ar—H, ddd, J 1.6, 2.6 and 8.2), 7.34 (1H, Ar—H, t, J 7.9), 7.59 (1H, Ar—H, dd, J 1.5 and 2.5) and 7.67 (1H, Ar—H, dt, J 1.4 and 7.6).

Step 2

3-[2-Azido-2-(2-hydroxy-ethoxy)ethoxy]benzoic acid ethyl ester

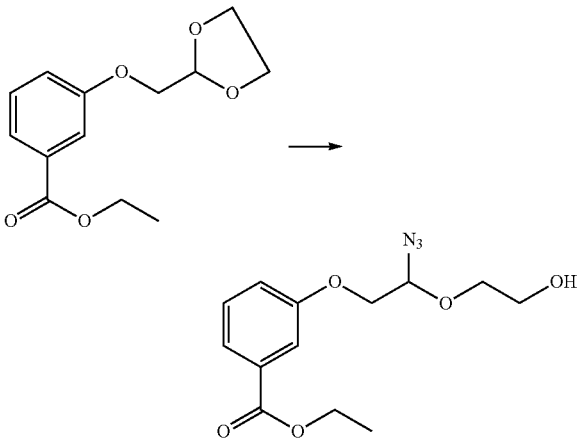

To a mixture of 3-([1,3]-dioxolan-2-ylmethoxy)-benzoic acid ethyl ester (2.02 g, 8 mmol) and azidotrimethylsilane (1.17 ml, 8.8 mmol) was added $SnCl_4$ (60 μl) at room temperature under nitrogen. After 2 hr, 2% aqueous methanol (10 ml) was added to the reaction mixture and the reaction was stirred at room temperature for 30 minutes. All the solvents were evaporated under reduced pressure. The residue was co-evaporated with ethanol (2×10 ml). The residue was purified by column chromatography (3×20 cm). The product was eluted with 0 to 1% methanol in DCM. The title compound was obtained as a colourless oil (2.01 g, 85.1%). APCI-MS, m/z 267.90 (M—$N_2$+1).

$^1$HNMR [$CDCl_3$]: 1.38 (3H, $CH_3$, t, J 7.1), 3.73-3.86 (3H, $OCH_2$, $H_a$, $OCH_2$, m), 3.99-4.05 (1H, $OCH_2$, $H_b$, m), 4.17 (1H, Ar—$OCH_2$, $H_a$, dd, J 4.9 and 10.1), 4.23 (1H, $ArOCH_2$, $H_b$, dd, J 5.2 and 10.1), 4.38 (2H, $OCH_2$, q, J 7.1), 4.89 (1H, CH—$N_3$, t, J 5.1), 7.13 (1H, Ar—H, dd, J 2.1 and 8.4), 7.36 (1H, Ar—H, t, J 7.9), 7.60 (1H, Ar—H, dd, J 1.0 and 2.5) and 7.70 (1H, Ar—H, d, J 7.8).

Step 3

3-[2-Azido-2-(2-hydroxyethoxy)ethoxy]benzoic acid

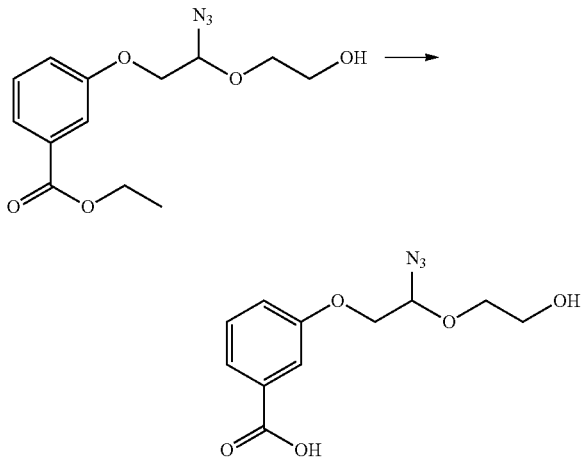

32-Azido-2-(2-hydroxyethoxy)ethoxy]benzoic acid ethyl ester (1.34 g, 4.55 mmol) was stirred with 4 M aqueous sodium hydroxide (11.4 ml, 45.5 mmol) and ethanol (11.4 ml) at room temperature. After 3 hrs, all the solvents were removed under reduced pressure and the residue was dissolved in 50 ml water. The solution was acidified with 1N HCl to pH 2 and then extracted with DCM (3×50 ml). All the DCM extracts were combined, dried over $MgSO_4$ and evaporated under reduced pressure. The title compound was obtained as a colourless solid (1.2 g, 98.7%). ES-MS, m/z 265.85 (M−1).

$^1$HNMR [$CDCl_3$]: 3.75-3.90 (3H, $OCH_2$, $H_a$, $OCH_2$, m), 4.00-4.08 (1H, $OCH_2$, $H_b$, m), 4.17 (1H, Ar—$OCH_2$, $H_a$, dd, J 4.8 and 10.1), 4.24 (1H, $ArOCH_2$, $H_b$, dd, J 5.1 and 10.1), 4.90 (1H, CH—$N_3$, t, J 5.1), 7.19 (1H, Ar—H, dd, J 2.5 and 8.2), 7.40 (1H, Ar—H, t, J 8.0), 7.60 (1H, Ar—H, s) and 7.70 (1H, Ar—H, d, J 7.9).

Step 4

3-[2-Azido-2-(2-ethoxycarbonylmethoxyethoxy)ethoxy]benzoic acid

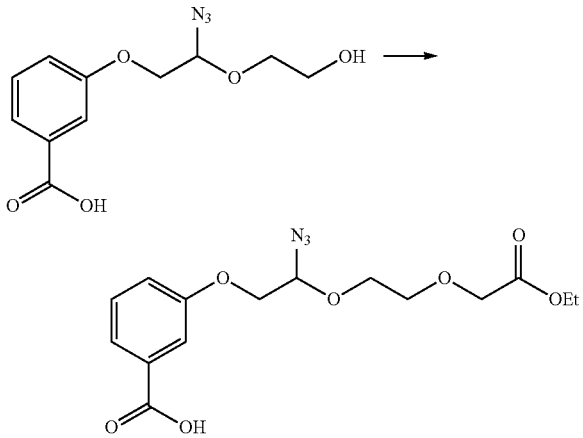

To a solution of 3-[2-azido-2-(2-hydroxyethoxy)ethoxy]benzoic acid (0.535 g, 2 mmol) in dry THF (6 ml) was added NaH (60% dispersion, 0.246 g, 6 mmol) at 0° C. After 10 minutes, ethyl 2-bromoacetate (0.488 ml, 4.4 mmol) was added. The reaction was then warmed up to room temperature and stirred for 4 hours. The reaction was quenched by pouring it into ice-cold water (50 ml). The mixture was extracted with DCM (2×50 ml) and the-DCM extracts were discarded. The aqueous layer was then acidified to pH 2 with 1 N HCl, and extracted with DCM (2×50 ml). These DCM extracts were combined, dried over $MgSO_4$ and evaporated under reduced pressure. The residue was purified by column chromatography (1×20 cm). The title compound, eluted with 2% methanol in DCM, was obtained as an oil (0.223 g, 31.6%). ES-MS, m/z 351.95 (M−1).

$^1$HNMR [$CDCl_3$]: 1.29 (3H, $CH_3$, t, J 7.2), 3.81 (2H, $OCH_2$, t, J 4.4), 3.90 (1H, $OCH_2$, $H_a$, m), 4.04 (1H, $OCH_2$, $H_b$, m), 4.13-4.27 (6H, $ArOCH_2$, $OCH_2$ and $OCH_2C(O)$), 4.95 (1H, CH—$N_3$, m), 7.19 (1H, Ar—H, dd, J 1.7 and 8.3), 7.40 (1H, Ar—H, t, J 7.8), 7.63 (1H, Ar—H, s) and 7.76 (1H, Ar—H, d, J 7.6).

Step 5

[2-(1-Azido-2-{3-[2-(2,2,2-trifluoroacetylamino)ethylcarbamoyl]phenoxy}ethoxy)ethoxy]acetic acid ethyl ester

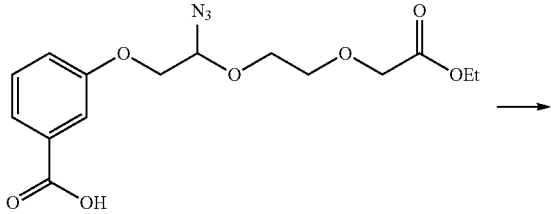

-continued

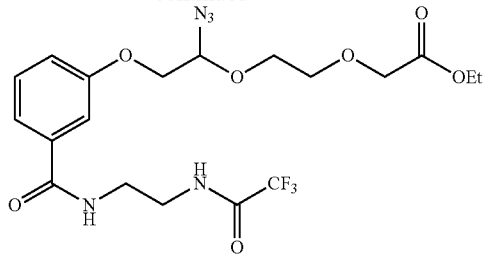

3-[2-Azido-2-(2-ethoxycarbonylmethoxyethoxy)ethoxy]benzoic acid (0.212 g, 0.6 mmol) was stirred with N,N'-disuccinimidyl carbonate (0.184 g, 0.72 mmol) and DMAP (0.088g, 0.72 mmol) in dry DMF (1 ml) at room temperature. After 10 minutes, trifluoroacetic acid salt of N-(2-aminoethyl)-2,2,2-trifluoroacetamide (0.194 g, 0.72 mmol) was added followed by diisopropylethylamine (DIPEA) (0.251 ml, 1.44 mmol). The reaction mixture was then stirred at room temperature for 17 hours. All the solvents were evaporated under reduced pressure and the residues were partitioned between DCM (50 ml) and aqueous $NaH_2PO_4$ (1 N, 50 ml). The aqueous layer was further extracted with DCM (2×25 ml). All the DCM extracts were combined, dried over $MgSO_4$ and evaporated under reduced pressure. The residue was purified by column chromatography (1×20 cm). The title compound, eluted with 1% methanol in DCM, was obtained as an oil (0.255 g, 86.6%). ES-MS, m/z 490.10 (M−1).

$^1$HNMR [$CDCl_3$]: 1.28 (3H, $CH_3$, t, J 7.1), 3.60 (2H, $CH_2N$, m), 3.69 (2H, $CH_2N$, m), 3.80 (2H, $OCH_2$, t, J 4.3), 3.86 (1H, $OCH_2$, $H_a$, m), 4.04 (1H, $OCH_2$, $H_b$, m), 4.10-4.25 (6H, $ArOCH_2$, $OCH_2$ and $OCH_2C(O)$, m), 4.92 (1H, CH—$N_3$, m), 6.85 (1H, NH, br), 7.09 (1H, Ar—H, m), 7.37 (3H, Ar—H, m), and 7.96 (1H, NH, br).

Step 6

(2-{2-[3-(2-Amino-ethylcarbamoyl)phenoxy]-1-azidoethoxy}ethoxy)acetic acid (LN3)

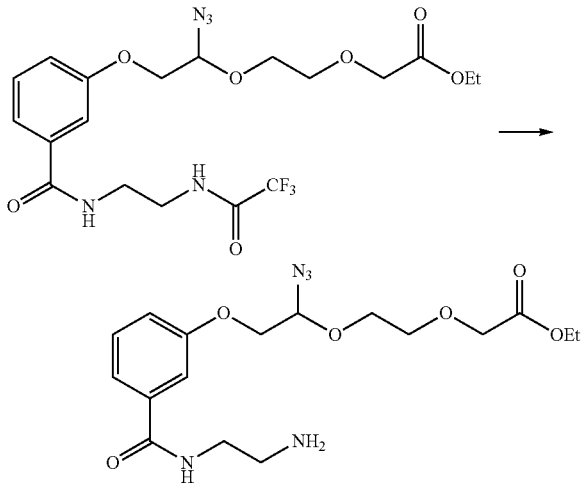

[2-(1-Azido-2-{3-[2-(2,2,2-trifluoroacetylamino)ethoxycarbamoyl]phenoxy}ethoxy)ethoxy]acetic acid ethyl ester (0.196 g, 0.4 mmol) was stirred with 4 M aqueous sodium hydroxide (1ml, 4 mmol) and ethanol (1 ml) at room temperature. After 2 hrs, all the solvents were removed under reduced pressure and the residue was dissolved in 15 ml water. The solution was extracted with DCM (2×15 ml). The DCM extracts were discarded and the aqueous layer was acidified with 1N HCl to pH 2. Then the solution was extracted again with DCM (3×15 ml). The DCM extracts were discarded and the aqueous layer was neutralised with 1N NaOH to pH 8 and then evaporated under reduced pressure to dryness. The white solids were triturated with DCM/MeOH (v/v; 1:1, 2×25 ml). All the solids were filtered off and the filtrates were combined and evaporated under reduced pressure to give a gum. The gum was added in 10% MeOH in DCM (15 ml) and the insoluble, white solids were filtered off. The filtrates were evaporated under reduced pressure to give the mono-sodium salt of the title compound as colourless powders (0.135 g, 86.6%). ES-MS, m/z 368.00 (M+1).

$^1$HNMR [$D_2O$]: 3.01 (2H, $CH_2NH_2$, t, J 6.0), 3.51 (2H, $CH_2N$, t, J 6.0), 3.62 (2H, $OCH_2$, m), 3.77 (1H, $OCH_2$, $H_a$, m), 3.80 (2H, $CH_2C(O)$, s), 3.96 (1H, $OCH_2$, $H_b$, m), 4.19 (2H, $ArOCH_2$, d, J 4.3), 5.01 (1H, CH—$N_3$, t, J 4.5), 7.13 (1H, Ar—H, d, J 7.9) and 7.25-7.39 (3H, Ar—H, m).

The preparation of the four 3'-blocked nucleotide triphosphate structures used to attach the dyes in the following synthesis, is fully described in the previously published patent application WO04018497, which is incorporated herein by reference in its entirety.

Example 9

Preparation of DYE 2 Nucleoside Triphosphate

Step 1

Attachment of an Azide Linker (Preparation of 'Dye 2'-LN3)

Reaction Scheme:

Target compound molecular formula: $C_{52}H_{61}N_8O_{15}S_2^-$

Target compound molecular weight: 1102.22

Reaction Conditions: An aqueous solution of Dye 2 (30.58 μmol) was evaporated in a round bottom flask and dissolved in anhydrous DMF (5 ml) under Argon. Solid TSTU (13.8 mg, 45.87 μmol) was added followed by neat DIPEA. The reaction mixture was allowed to stir at ambient temperature under argon for 19 minutes before analysing by TLC (4:1 acetonitrile-water, Aldrich TLC plates 200 μm layer, 2-25 μm particle size, 60 A pore). Full activation of the dye ($R_f$ 0.38) was observed, generating the activated ester ($R_f$0.55). A solution of LN3 (33.7 mg, 91.74 μmol) and DIPEA (32 μL, 183.48 μmol) in anhydrous DMF (1.8 mL) was added. The reaction progress was monitored by TLC using the aforementioned eluant system. After 1.8 hour complete consumption of activated ester ($R_f$ 0.55) and formation of the product ($R_f$ 0.32) was observed.

Work up procedure: The reaction was quenched with ice-cold 0.1 M TEAB (5 mL) and the solvent evaporated to dryness. The resulting crude material was re-dissolved in 0.1 M TEAB and filtered through 0.2μ syringe.

Purification procedure: Purified using an automated Agilent HPLC (5-50 method in 25 min on a prep Zorbax Agilent Column SB-C18 21.2×250 mm, 7 μm). Retention time 17.08 min.

Yield: 21.4 μmol (70%)

Proton NMR 400 MHz ($D_20$) (aromatic region only): 7.51-7.54 (3H, m, $CH_{AR}$, $CH_{AR}$, $CH_{AR}$), 7.38-7.41 (1 H, m, $CH_{AR}$), 7.20-7.22 (1H, m, $CH_{AR}$), 7.09-7.18 (2H, m, $CH_{AR}$), 6.93-6.95 (2H, m, $CH_{AR}$, $CH_{AR}$), 6.59 (1H, s, $CH_{AR}$), 6.41 (2H, d, J 8.0 $CH_{AR}$ Mass spec details: MS (es$^-$, m/z): 550.2 doubly charged.

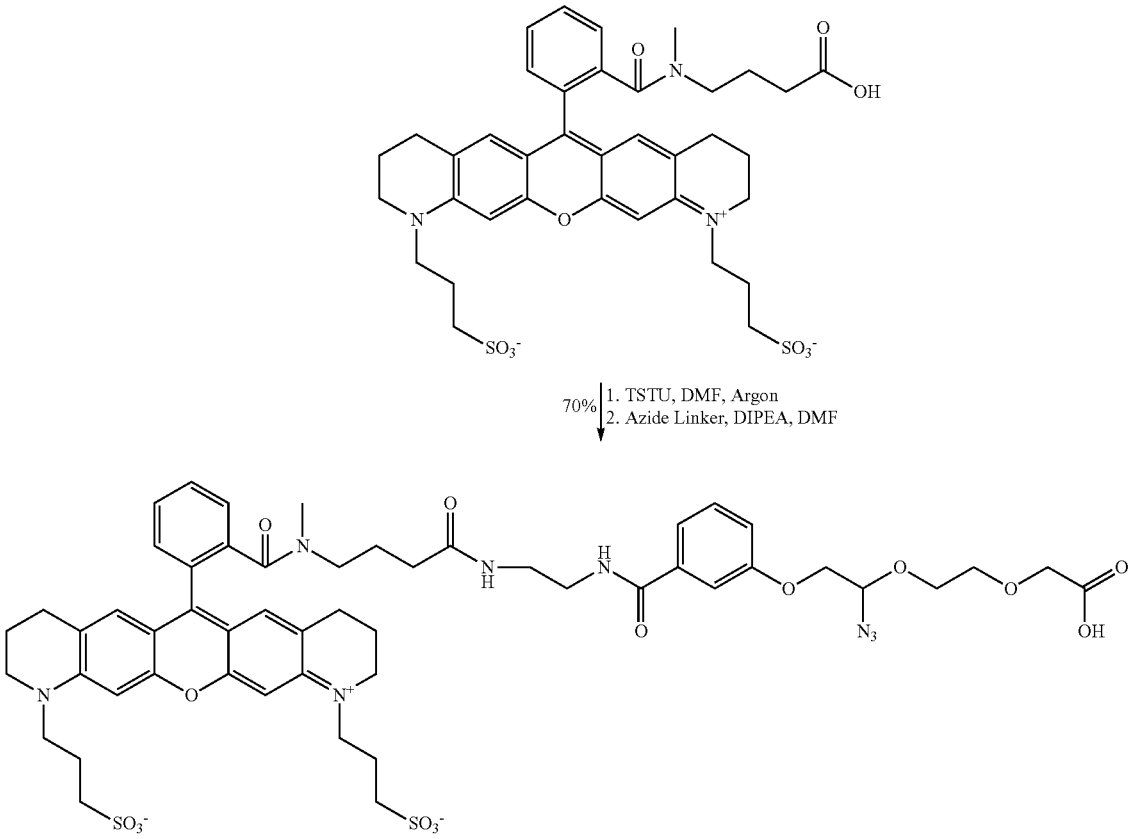

Step 2

Attachment of 'Dye 2'-LN3 to T Nucleotide Triphosphate

Reaction Scheme:

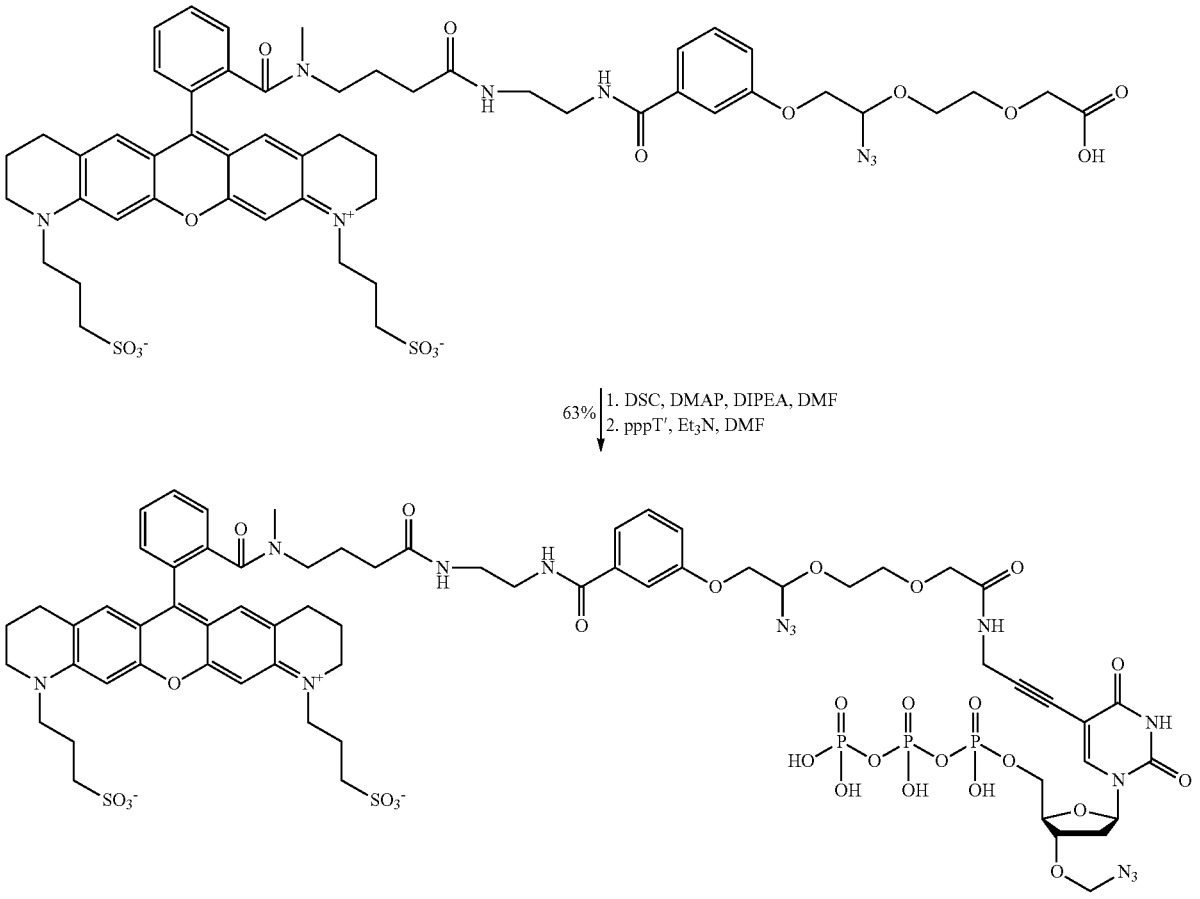

Target compound molecular formula: $C_{65}H_{78}N_{14}0_{28}P_3S_2^-$

Target compound molecular weight: 1660.44

Reaction Conditions: DYE 2-LN3 (3.39 μmol) was dissolved in anhydrous DMF (2.5 mL) under argon in a 50 mL plastic tube.

To this was added DSC (1.3 mg, 5.09 μmol} and DMAP (0.62 mg, 5.09 μmol) in 30 μL each respectively and DIPEA (10 μL). The reaction mixture was allowed to stir at ambient temperature under argon for 28 minutes before analysing by TLC (4:1 acetonitrile: water, Aldrich TLC plates 200μ layer, 2-25μ particle size, 60 A pore). Full activation of DYE 2-LN3 ($R_f$40) was observed, generating the activated linker ($R_f$0.63). A solution of pppT (10.17 μmol, 5 mM) which had been evaporated to dryness; was dissolved in anhydrous DMF (400 μL) and added to the activated linker. This was stirred at ambient temperature for 5 min and then $Et_3N$ (1.4 μL, 10.17 μmol) was added. The reaction progress was monitored by TLC using the aforementioned eluant system. After 90 minutes complete consumption of activated linker ($R_f$0.40) and formation of major product ($R_f$0.21) was observed.

Work up procedure: The reaction was quenched with ice-cold 0.1 M TEAB (2.5 mL) and the solvent evaporated to dryness. The resulting crude material was re-dissolved in 0.1M TEAB and filtered through 0.2μ syringe.

Purification procedure: Purified using the automated Agilent HPLC (5-50 method in 25 min on a semi-prep Eclipse XDB SB-C18 Agilent Column 9.4'250 mm, 5 μm). Retention time 14.28 min.

Yield : 2.14 μmol (63%)

Proton NMR ($D_2O$) (aromatic region only): 7.54-7.60 (2H, m, $CH_{Ar}$, $CH_{Ar}$), 7.51 (1 H, s, $CH_{Ar}$), 7.36-7.39 (1H, m, $CH_{Ar}$), 7.29-7.31 (1H, m, $CH_{Ar}$), 7.13-7.18 (2H, m, $CH_{Ar}$, (2H, d, J 6.0 $CH_{Ar}$).

$^{31}P$ NMR (162 MHz, $D_2O$, 300 K): δ −21.08 (t, J=19.8 Hz, $^{\beta}P$), −10.28 (d, J=18.5 Hz, $^{\alpha}P$), −5.17 (d, J=20.4 Hz, $^{\gamma}P$).

Mass spec details: MS(es−, m/z):829.25 doubly charged, triply charged.

Preparation of the Other 3 Nucleotide Kit Components

Example 10

Preparation of A-S-07181 Step 1

Synthesis of Ferrania S-07181-LN3

Molecular formula: $C_{47}H_{58}N_8O_{12}S_2$

Molecular weight: 991.14

Reaction Scheme:

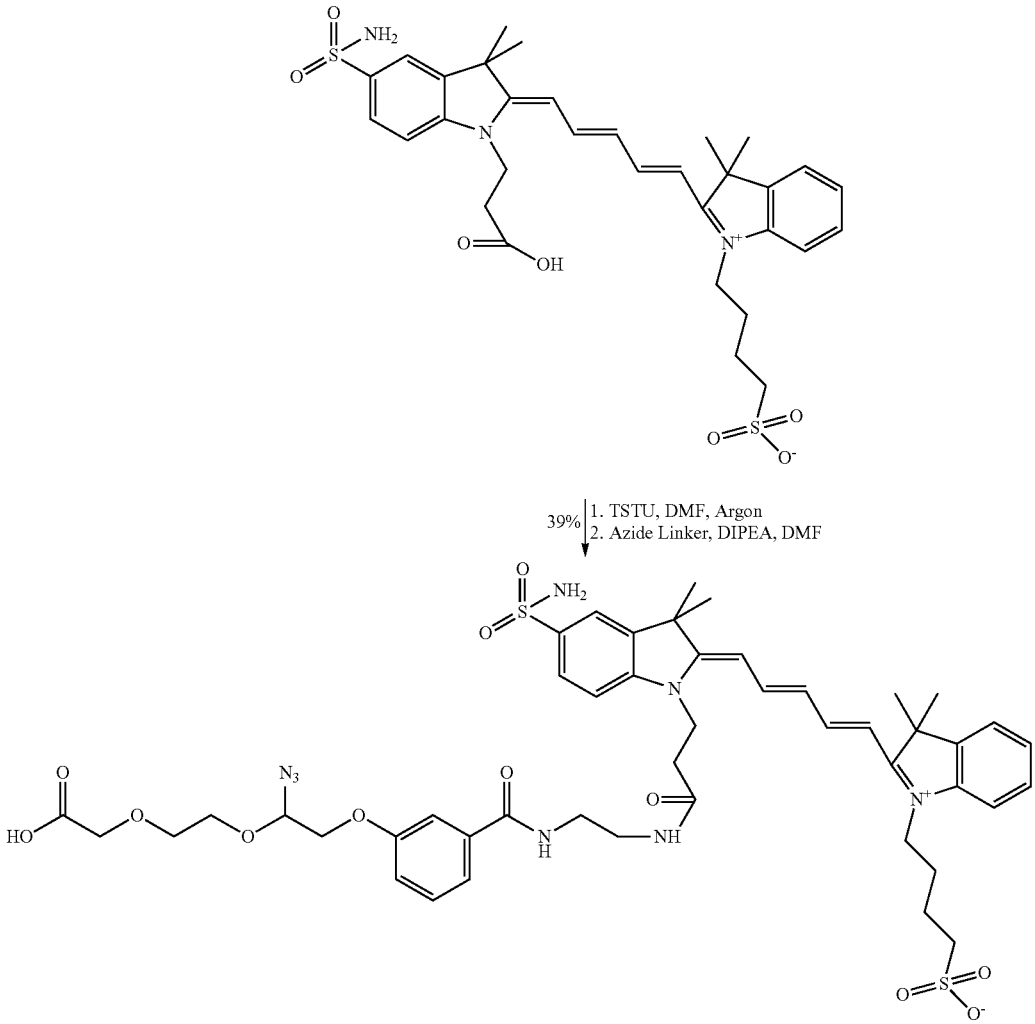

Reaction Conditions: The Dye S-07181 (19.17 μmol) as supplied (Ferrania Imaging Technologies, Italy) was dissolved in anhydrous DMF (9 mL) under argon. TSTU (14 mg, 46.8 μmol) in DMF (250 μL) was added. The reaction mixture was stirred at ambient temperature under Argon for 28 minutes before analysing by TLC (4:1 acetonitrile: water, Aldrich TLC plates 200μ layer, 2-25μ particle size, 60A pore). Partial activation of Ferrania S-07181 acid ($R_f$ 0.46) was observed, generating the activated ester ($R_f$ 0.60). An extra batch of TSTU (14 mg, 46.8 μmol) in DMF (250 μL) was added followed by the addition of DIPEA (10 μL). Complete activation was achieved after 12 minutes. A solution of LN3 (34.4 mg, 93.6 μmol) and DIPEA (33 μL, 187.2 μmol) in anhydrous DMF (2 mL) was added. This mixture was stirred at ambient temperature under argon. The reaction progress was monitored by TLC using the aforementioned eluant system. After 18 hours, complete consumption of activated ester ($R_f$ 0.60) and formation of the product ($R_f$ 0.23) was observed.

Work-up procedure: The reaction was quenched with ice-cold 0.1 M TEAB (8 mL) and the solvent evaporated to dryness. The resulting crude material was re-dissolved in 0.1 M TEAB and filtered through 0.2μ syringe.

Purification procedure: Purified using the automated Agilent HPLC (5-50 method in 25 min on a semi-prep Eclipse XDB SB-C18 Agilent Column 9.4×250 mm, 5 μm). Retention time 17.09 min. Recovered Ferrania S-07181 acid 16.39 min.

Yield: 7.41 μmol (39%)

PMR ($D_2O$) (Aromatic region only): 8.30 (1H, t, J 12.0 $CH_{Ar}$), 8.15 (1H, t, J 13.0 $CH_{Ar}$), 7.85-7.87 (2H, m, $CH_{Ar}$, $CH_{Ar}$), 7.48-7.58 (3H, m, $CH_{Ar}$, $CH_{Ar}$, $CH_{Ar}$), 7.43-7.45 (2H, m, $CH_{Ar}$, $CH_{Ar}$), 7.36-7.40 (2H, m, $CH_{Ar}$, $CH_{Ar}$), 7.28 (1H, d, J 9.0 $CH_{Ar}$), 7.11-7.14 (1H, m, $CH_{Ar}$), 6.51 (2H, d, J 9.0 $CH_{Ar}$).

Mass spec details: MS ($es^-$, m/z): 989.40 singly charged, 494.45 doubly charged.

Step 2

Synthesis of Ferrania S-07181-LN3-ATP

Molecular formula: $C_{62}H_{77}N_{16}O_{23}S_2$

Molecular weight: 1571.42

Reaction Scheme:

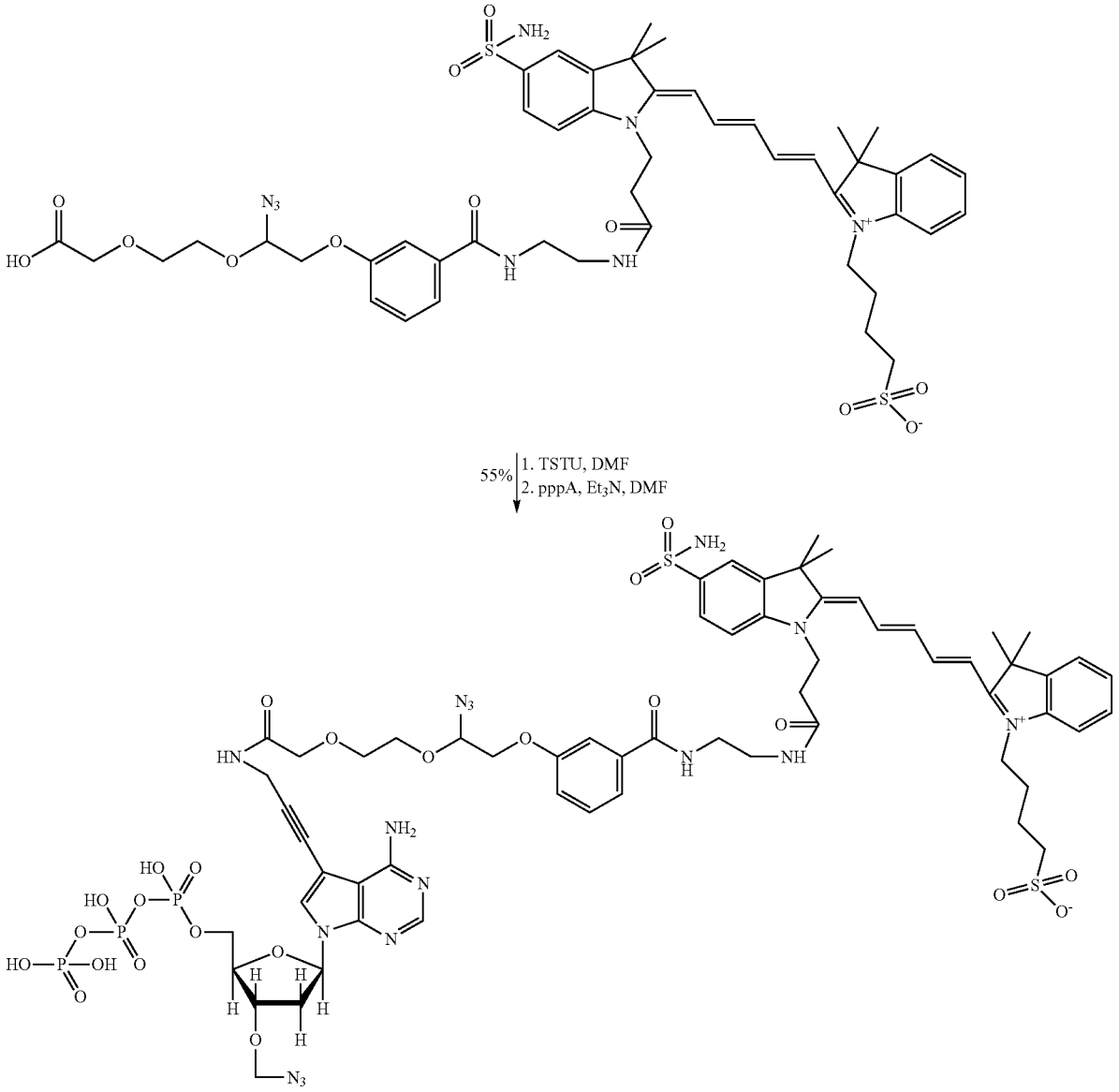

Reaction Conditions: The product (S-07181LN3CO2H) from previous step (11.8 μmol) was dissolved in anhydrous DMF (7 mL) under argon in a 50 mL plastic tube. TSTU (5.3 mg, 17.7 μmol) in DMF (150 μL) was added. The reaction mixture was stirred at ambient temperature under Argon for 9 minutes before analysing by TLC (4:1 acetonitrile: water, Aldrich TLC plates 200μ layer, 2-25μ particle size, 60 A pore). Full activation of Ferrania S-07181LN3CO2H ($R_f$ 0.39) was observed, generating the activated linker ($R_f$ 0.74). A solution of pppA (35.4 μmol, 9.84 mM) which had been evaporated to dryness; was dissolved in anhydrous DMF (500 μL) and added to the activated linker. This was stirred at ambient temperature for 5 min and then $Et_3N$ (5 μL, 35.4 μmol) was added. The reaction progress was monitored by TLC using the aforementioned eluent system. After 43 minutes complete consumption of activated linker ($R_f$ 0.74) and formation of the product ($R_f$ 0.15) was observed.

Work-up procedure: The reaction was quenched with ice-cold 0.1 M TEAB (20 mL) and the solvent evaporated to dryness. The resulting crude material was re-dissolved in 0.1 M TEAB and filtered through 0.2μ syringe.

Purification procedure: Purified using the automated Agilent HPLC (5-50 method in 20 min on a prep Zorbax Agilent Column SB-C18 21.2×250 mm, 7 μm, SOL-P2-AUG-2005). Retention time 16.38 min.

Yield: 6.45 μmol (55%)

PMR ($D_2O$) (aromatic region only): 7.79 (1H, d, J 5.0 $CH_{Ar}$), 7.64-7.67 (3H, m, $CH_{Ar}$, $CH_{Ar}$, $CH_{Ar}$), 7.52 (1H, t, J 13.0 $CH_{Ar}$), 7.22-7.41 (6H, m, $CH_{Ar}$, $CH_{Ar}$ $CH_{Ar}$, $CH_{Ar}$, $CH_{Ar}$, $CH_{Ar}$), 6.99-7.08 (3H, m, $CH_{Ar}$, $CH_{Ar}$, $CH_{Ar}$), 6.73-7.00 (2H, m, $CH_{Ar}$, $CH_{Ar}$), 6.12 (1H, dd, J 6, J 3 $CH_{Ar}$), 5.92-5.99 (1H, m, $CH_{Ar}$), 5.78 (1H, d, J 13.0 $CH_{Ar}$).

Phosphorus NMR ($D_2O$): −5.02 (1P, d, J 20.0), −10.18 (1P, d, J 20), −21.0 (1P, t, J 20).

Mass spec details: MS ($es^-$, m/z): 784.50 doubly charged, 528.85 Na triply charged.

Example 11

Preparation of Alexa 647-LN3-dATP

Step 1

Preparation of Alexa 647-LN3

Reaction Conditions: Alexa647NHS ester (10 mg, 8 μmol), (Molecular probes A20106), LN3 (8.8 mg, 24 μmol) and DIPEA (8 μL, 48 μmol) were dissolved in anhydrous DMF (4 mL) in a round bottom flask under $N_2$. Analysis by TLC after 24 h, (4:1 acetonitrile: water, Aldrich TLC plates 200μ layer, 2-25μ particle size, 60 A pore) showed complete reaction.

Work-up procedure: The reaction was quenched with 0.1 M TEAB (5 mL) and the solvent evaporated to dryness and stored in the fridge. The resulting crude material was re-dissolved in 0.1 M TEAB and filtered through 0.2μ syringe.

Purification procedure: The material was purified by HPLC using a 5-50% MeCN method in 20 min; 5 ml $min^{-1}$ on a semi-prep Zorbax Agilent Column SB-C18 4.6×250 mm, 5 μm). Retention time 11.04 min.

Yield: 5.65 μmol (71%)

Compound appearance: Deep blue colour.

PMR ($D_2O$) (aromatic region): 7.77-7.88 (2H, m, 2×$CH_{Ar}$), 7.54-7.61 (4H, m, 4×$CH_{Ar}$), 7.09-7.15 (2H, dd, J 8.5, 8.0 Hz, 2×$CH_{Ar}$), 7.01-7.05 (2H, m, 2×$CH_{Ar}$), 6.88-6.91 (2H, m, 2×$CH_{Ar}$), 6.37 (1H, dd, J 12.5, 12.0 Hz, C═CH), 6.18 (1H, d, J 13.5 Hz, ═CH), 5.98-6.01 (1H, d, J 13.5 Hz, ═CH.

Mass spec details: MS ($es^-$, m/z): 603.00 doubly charged. 401.75 triply charged.

Step 2

Synthesis of Alexa 647-LN3-dATP

Reaction Conditions: Alexa647$LN_3CO_2H$ (3.35 μmol) was dissolved in anhydrous DMF (1.1 mL) in a 5 mL round bottom flask under $N_2$. To this was added DSC (1.28 mg, 5.02 μmol) and DMAP (0.61 mg, 5.02 μmol) in 20 μL each respectively. The reaction mixture was stirred at ambient temperature under $N_2$ for 5 minutes before analysing by TLC (4:1 acetonitrile: water, Aldrich TLC plates 200μ layer, 2-25μ particle size, 60 A pore). Full activation of Alexa647$LN_3CO_2H$ ($R_f$ 0.48) was observed, generating the activated linker ($R_f$ 0.64). A solution of pppA (10.05 μmol, 9.84 mM), which had been concentrated in Bu3N (20 μL); was dissolved first in 0.1M TEAB (20 μL) followed by the addition of anhydrous DMF (200 μL) and cooled to 0° C. This was added to the cold activated linker. After 60 minutes complete consumption of activated linker ($R_f$0.64) and formation of the product ($R_f$ 0.24) was observed by TLC Work-up procedure: The reaction was quenched with ice-cold 0.1 M TEAB (1.5 mL) and the solvent evaporated to dryness. The resulting crude material was re-dissolved in 0.1 M TEAB and filtered through 0.2μ syringe.

Purification procedure: The material was purified by HPLC as described in step 1. Retention time 11.537 min.

Yield: 2.19 μmol (65%)

Compound appearance: Deep blue colour.

PMR ($D_2O$) (aromatic region): 7.66-7.75 (7H, m, 7×$CH_{Ar}$), 7.48-7.58 (5H, m, 5×$CH_{Ar}$), 7.28-7.30 (1H, m, $CH_{Ar}$), 7.08 (1H, d, J 8 Hz, $CH_{Ar}$), 6.99-7.01 (1H, m, $CH_{Ar}$), 6.88-6.92 (2H, m, 2×$CH_{Ar}$), 6.72 (1H, br. s, $CH_{Ar}$), 6.65-6.66 (1H, m, $CH_{Ar}$), 6.27-6.33 (1H, m, $CH_{Ar}$), 6.05-6.09 (2H, m, $CH_{Ar}$, $CH_{Ar}$), 5.92-5.95 (1H, m, $CH_{Ar}$).

Phosphorus NMR (state solvent): $^{31}P$ NMR (162 MHz, $D_2O$, 300K): δ −20.43 (dt, J=19.0 Hz, $^{\beta}P$), −10.06 (dd, J=18.0 Hz, $^{\alpha}P$), −4.95 (d, J=21 Hz, $^{\gamma}P$).

Mass spec details: MS ($es^-$, m/z): 893.1 doubly charged, 595.05 triply charged.

Example 12

Preparation of Dy681-LN3-dCTP

Step 1

Synthesis of DY681-LN3

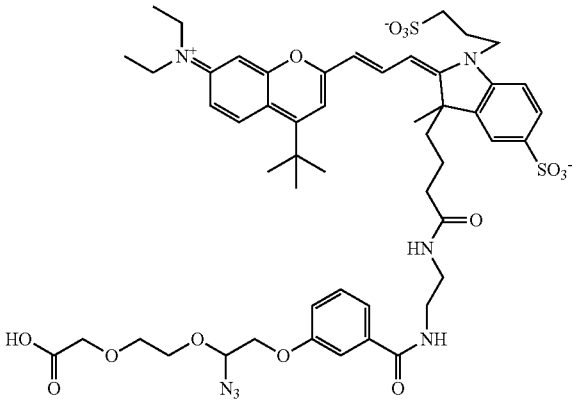

$C_{51}H_{64}N_7O_{14}S_2^-$
Exact Mass: 1062.40
Mol. Wt.: 1063.22

DY681NHS ester (5 mg, 5.9 pmol) (Dyomics 681-01) was dissolved in DMF (1.3 ml). A solution of LN3 (6.6 mg, 17.9 μmol) and DIPEA (6 μl, 35.9 μmol) in DMF (0.5 ml) was added. The reaction progress was monitored by TLC (eluting system $CH_3CN$:$H_2O$ 4:1) and by HPLC (5-100 method in 20 min in the semiprep Zorbax column). The reaction was stopped after 4 h. The solvent was evaporated and the reaction crude was redissolved in 0.1 M TEAB. The crude was purified by HPLC using the same method and column aforementioned, retention time 11.5 min. DY681LN3 was obtained in 55% yield.

MS (es−, m/z): 530.9

$^1H$ NMR (400 MHz; $D_2O$) 7.86 (1H, d, J 13.6, CHar), 7.79 (1H, d, J 9.6, CHar), 7.57-7.56 (2H, m, CHar,CHar), 7.17 (1H, t, J 8.0, CHar), 6.98 (1H, d, J 8.0, CHar), 6.83-6.73 (4H, m, CHar, CHar, CHar, CHar), 6.59 (1H, d, J 9.6, CHar), 6.10 (1H, s, CHar), 5.98 (1H, d, J 13.6, CHar), 5.69 (1H, br.s, J 14.0, CHar), 4.96-4.93 (1H, m, $CHN_3$), 4.11-4.03 (2H, m, $CH_2$—O-Ph), 3.96-3.90 (1H, m, CHH), 3.81 (2H, s, $CH_2$—O), 3.80-3.74 (1H, m, CHH—O), 3.64-3.58 (2H, m, $CH_2$—O), 3.48-3.34 (1H, br.s, CHH), 3.31-3.17 (1H, br.s, CHH), 3.16-2.82 (8H, m, 4×$CH_2$), 2.80-2.62 (4H, m, partially under $NEt_3$ signal, 2×$CH_2$), 2.03-1.90 (2H, br.m, $CH_2$), 1.88-1.61 (8H, m, 2×$CH_2$, CHH, $CH_3$), 1.30 (9H, s, 3$CH_3$), 0.88-0.72 (4H, m, partially under $NEt_3$ signal, 2×$CH_2$), 0.60 (1H, br.s, CHH).

Step 2
Synthesis of C-LN3-DY681

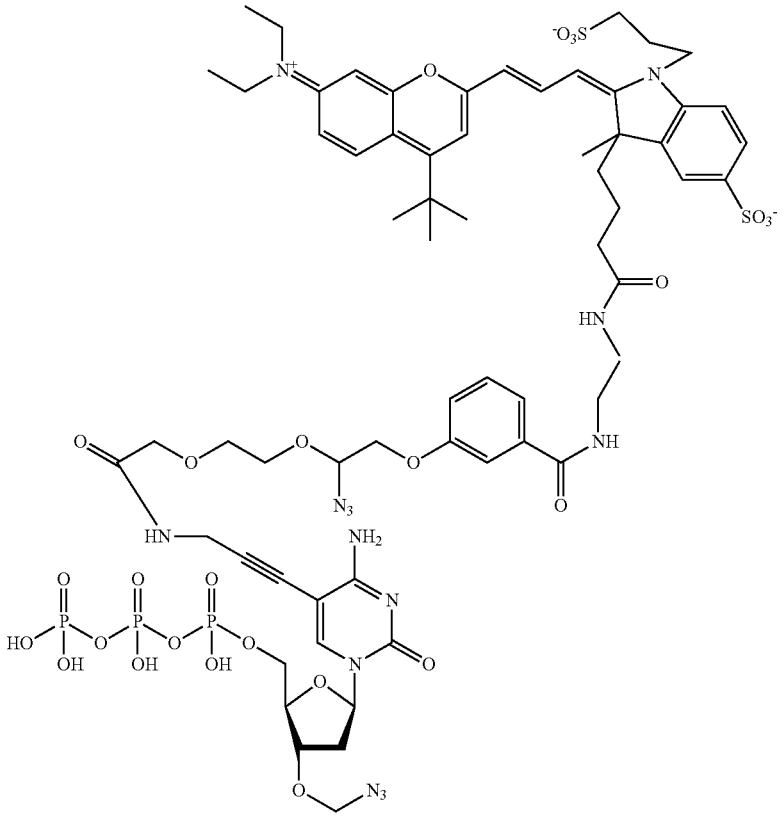

$C_{64}H_{82}N_{14}O_{26}P_3S_2^-$
Exact Mass: 1619.42
Mol. Wt.: 1620.47

DY681LN3 (3.13 μmol) was dissolved in DMF (1.5 ml). A solution of TSTU (1.4 mg, 4.7 μmol) in DMF (120 μl) was added. The activation progress was monitored by TLC (eluting system $CH_3CN:H_2O$ 4:1). DIPEA (2.7 μl) was added to aid the activation, which had a 80% progress in 20 min. PPPC (9.4 μmol, 4.87 mM) was co-evaporated with tributylamine (22 μl, 94 μmol), re-dissolved in DMF (300 μl) and added to the reaction mixture. The progress of the reaction was monitored by TLC (eluting system $CH_3CN:H_2O$ 4:1) and HPLC (5-100 method in 20 min in the semiprep Zorbax column). No further progress is observed 3.5 hours after adding the triphosphate, so the reaction was quenched with 2 ml of 0.1 M TEAB at 0° C. The solvents were evaporated and the reaction crude was re-dissolved in 0.1 M TEAB. The crude was purified by HPLC (5-100 method in 20 min in the semiprep Zorbax column) retention time 10.7 min. The compound was obtained in 62% yield.

$^{31}P$ NMR (162 MHz, $D_2O$, 300 K): δ −21.13 (t, J=19.8 Hz, $^{\beta}P$), −10.43 (d, J=19.1 Hz, $^{\alpha}P$), −5.07 (d, J=20.6 Hz, $^{\gamma}P$).

MS (es−, m/z): 809, 539, 404

Example 13

Preparation of Atto532-Peg12-LN3-dGTP
Step 1
Synthesis of Atto532-Peg12

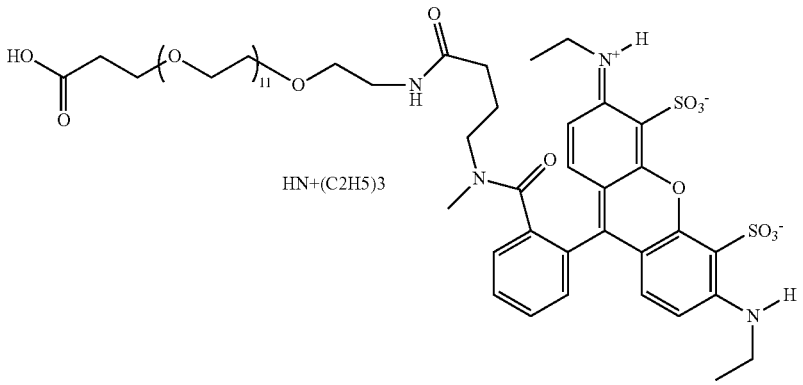

Atto532NHS ester (20 mg, 26.9 μmol) (Atto-tecAD532-3) was dissolved in DMF (1.5 ml). A solution of H2N-PEG12-COOH (49.8 mg, 80.7 mol) in 0.1 M TEAB (0.5 ml) was added to the reaction. The reaction was monitored by TLC (eluting system $CH_3CN:H_2O$ 4:1) and reached completion in 90 min. It was quenched with 2 ml of 0.1 M TEAB and concentrated to dryness. The crude reaction mixture was purified by doing a Sephadex column (1×10 cm). We eluted three fractions, first with 40 ml of 0.1 M TEAB, second with 100 ml of 0.3 M TEAB and finally with 100 ml of 0.5 M TEAB. The product of the reaction was contained in fraction 2. This was submitted to HPLC purification (5-50 method in 20 min in the semiprep Zorbax column), retention time 13.7 min. The product was obtained in 64% yield.

MS (es−, m/z): 1243, 622

1H NMR (400 MHz; $D_2O$) 7.65-7.56 (2H, m, CHar, CHar), 7.52-7.45 (1H, m, CHar), 7.40-7.36 (1H, m, CHar), 7.23-7.18 (2H, m which includes doublet, J 9.6, CHar, CHar), 6.92 (1H, d, J 9.6 CHar), 6.91 (1H, d, J 9.6, CHar), 3.58 (2H, t, J 6.8, $CH_2$), 3.55-3.45 [44H, m, 11×(O—$CH_2$)+11×($CH_2$—O)], 3.40 (2H, t, J 5.6, $CH_2$), 3.33 (4H, q, J 7.2, 2×$CH_2$), 3.19 (1H, t, J 5.6, CH), 3.14 (1H, t, J 5.6, CH), 3.09 (1H, br.t, CH), 2.78 (3H, s, $CH_3$), 2.31 (2H, t, J 6.8, $CH_2$), 1.60-1.52 (2H, m, $CH_2$), 1.32-1.24 (2H, m, $CH_2$), 1.17 (6H, t, J 7.2, 2×$CH_3$).

Step 2

Preparation of Atto532-PEG12-LN3

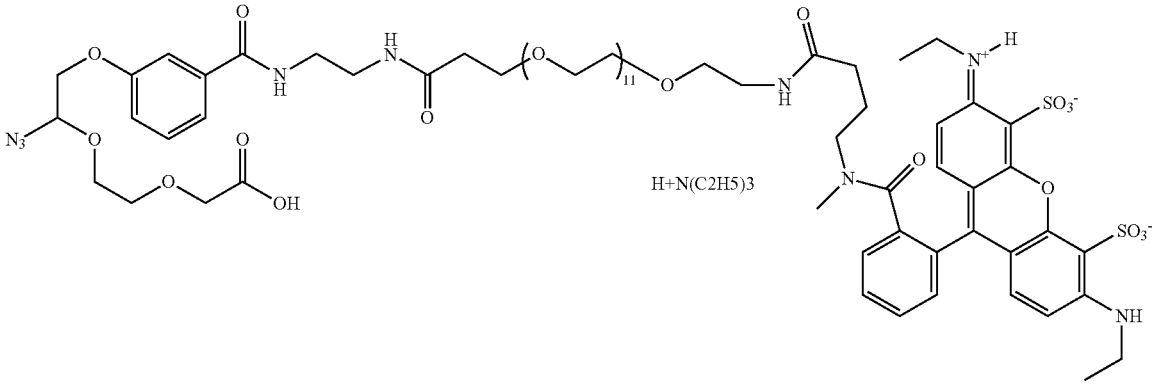

Atto532PEG (21.6 mg, 17.4 μmol) was dissolved in DMF (1.8 ml). A solution of TSTU (7.8 mg, 26.1 μmol) in DMF was added to the reaction. DIPEA (15 μl, 87 μmol) was added. The activation was completed in 30 min and LN3 (15.9 mg, 43.5 μmol) dissolved in DMF was added. The reaction was left stirring for 16 h, after which it was quenched with 10 ml of 0.1 M TEAB and vacuumed off. The crude reaction mixture was purified by HPLC (5-50 method in 20 min in the semiprep Zorbax column), retention time 14.9 min. The product was obtained in 66% yield.

MS (es−, m/z): 796

1H NMR (400 MHz; $D_2O$) 7.66-7.56 (2H, m, CHar, CHar), 7.54-7.45 (1H, m, CHar), 7.38-7.34 (1H, m, CHar), 7.28 (1H, q, J 8.0, CHar), 7.23-7.15 (4H, m, CHar), 7.08-7.01 (1H, br.d, J 8.0, CHar), 6.90 (1H, d, J 5.2, CHar), 6.88 (1H, d, J 5.2, CHar), 4.94 (1H, t, J 4.4, $CHN_3$), 4.12 (2H, br.d, J 4.0, $CH_2$), 4.00-3.86 (2H, double m, CHH), 3.81 (2H, s, O—$CH_2$), 3.81-3.72 (1H, m, CHH), 3.63-3.55 (5H, m, 2×$CH_2$+CH), 3.54-3.26 [53 H, triple m, 4×$CH_2$+CH+11×(O—$CH_2$)+11×($CH_2$ —O)], 3.22-3.12 (2H, m, $CH_2$), 2.76 (3H, s, $CH_3$), 2.35 (2H, t, J 5.6, $CH_2$), 1.96-1.90 (1H, m, CH), 1.60-1.49 (1H, m, CH), 1.31-1.22 (1H, m, $CH_2$), 1.17 (6H, t, J 7.2, 2×$CH_3$).

Step 3
Synthesis of G-Atto532-PEG12-LN3

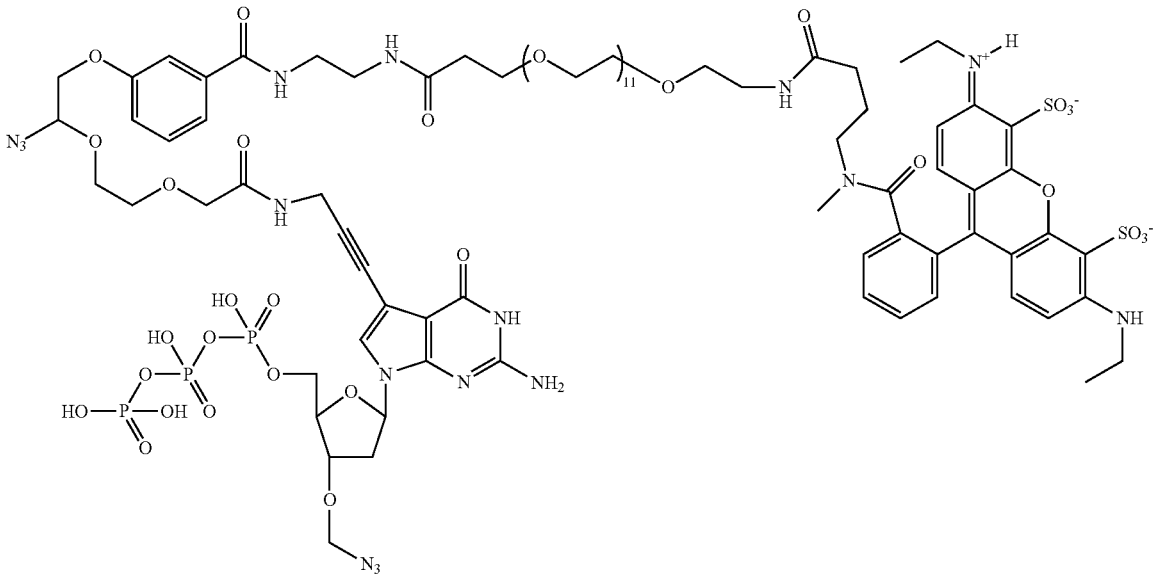

Atto532PEGLN3 (18 mg, 11.3 μmol) was dissolved in DMF (3 ml). A solution of TSTU (5.1 mg, 17 μmol) in DMF (200 μl) was added. The progress of the reaction was monitored by TLC (eluting system $CH_3CN:H_2O$ 4:1 and DIPEA (10 μl) was added. After 30 min, the TLC shows that the activation was completed. PPPG (34 μmol, 2.25 mM) was co-evaporated with tributylamine (81 μl) and redissolved in 0.1 M TEAB (0.5 ml). After 30 min, TLC showed that the reaction had gone to completion (eluting system $CH_3CN$: $H_2O$ 4:1). The reaction was quenched with 10 ml of 0.1 M TEAB at 0° C. and vacuumed off. The reaction crude was purified by HPLC (5-50 method in 20 min in the semiprep Zorbax column), retention time 14.8 min. The product was obtained in 57% yield.

MS (es−, m/z): 1095, 729, 546

1H NMR (400 MHz; $D_2O$) 7.64-7.60 (2H, m, CHar), 7.51-7.44 (1H, m, CHar), 7.35-7.31 (1H, m, CHar), 7.16-7.12 (4H, m, CHar), 7.09 (1H, s, CHbase), 6.99-6.96 (1H, br.s, CHar), 6.88 (1H, d, J 4.0, CHar), 6.86 (1H, d, J 4.0, CHar), 6.83-6.77 (1H, m, CHar), 6.06-5.96 (1H, m, H-1'), 4.96 (1H, br.s, $CHHN_3$), 4.82 (1H, br.s, $CHHN_3$), 4.54-4.46 (1H, m, H-3'), 4.20-4.14 (1H, m, H-4'), 4.12-3.89 (8H, double m, 3×$CH_2$+2H-5'), 3.86-3.60 (4H, m, $CH_2$+$CH_2$—N), 3.56 (2H, t, J 6.0, $CH_2$), 3.54-3.28 [56H, set m, 11×(O—$CH_2$)+11×($CH_2$—O)+6$CH_2$], 3.18 (2H, t, J 5.6, $CH_2$), 2.74 (3H, s, $CH_3$), 2.46-2.23 (4H, m+t+m, J 6.0, 2H-2'+$CH_2$), 1.61-1.34 (3H, m, $CH_2$+CH), 1.29-1.14 (8H, m+t, J 7.2, $CH_2$+2×$CH_3$).

Example 14

Preparation and Use of Nucleotide Kits for Sequencing Clusters of Amplified DNA Molecules Using SBS Preparation of Clusters for Sequencing The following are examples of general techniques which may be applied in carrying out the method of the invention. Detailed techniques for the preparation and treatment of clusters can be found in co-pending application WO07010251, the protocols from which are incorporated herein by reference in their entirety.

Acrylamide Coating of Glass Chips

The solid supports used are typically 8-channel glass chips such as those provided by Silex Microsystems (Sweden). However, the experimental conditions and procedures are readily applicable to other solid supports.

Chips were washed as follows: neat Decon for 30 min, milliQ $H_2O$ for 30 min, NaOH 1N for 15 min, milliQ $H_2O$ for 30 min, HCl 0.1N for 15 min, milliQ $H_2O$ for 30 min.

Polymer Solution Preparation

For 10 ml of 2% polymerisation mix.

- 10 ml of 2% solution of acrylamide in milliQ $H_2O$
- 165 μl of a 100 mg/ml N-(5-bromoacetamidylpentyl) acrylamide (BRAPA) solution in DMF (23.5 mg in 235 μl DMF)
- 11.5 μl of TEMED
- 100 μl of a 50 mg/ml solution of potassium persulfate in milliQ $H_2O$ (20 mg in 400 μl $H_2O$)

The 10 ml solution of acrylamide was first degas sed with argon for 15 min. The solutions of BRAPA, TEMED and potassium persulfate were successively added to the acrylamide solution. The mixture was then quickly vortexed and immediately used. Polymerization was then carried out for 1 h 30 min(?) at RT. Afterwards the channels were washed with milliQ $H_2O$ for 30 min and filled with 0.1 M potassium phosphate buffer for storage until required.

Example 15

Synthesis of N-[5-(2-bromoacetyl)aminopentyl] acrylamide

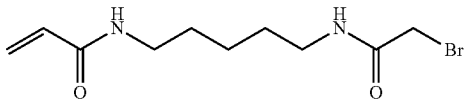

Starting Materials:

N-Boc-1,5-diaminopentane p-toluenesulfonate was obtained from Novabiochem. The bromoacetyl chloride and acryloyl chloride were obtained from Fluka. All other reagents were Aldrich products.

Step 1

N-[5-(t-Bytoxycarbonyl)aminopentyl]acrylamide

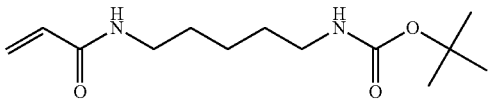

To a stirred suspension of N-Boc-1,5-diaminopentane p-toluenesulfonate (5.2 g, 13.88 mmol) and triethylamine (4.83 ml, 2.5 eq) in THF (120 ml) at 0° C. was added acryloyl chloride (1.13 ml, 1 eq) through a pressure equalized dropping funnel over a one hour period. The reaction mixture was then stirred at room temperature and the progress of the reaction checked by TLC (petroleum ether: ethyl acetate 1:1). After two hours, the salts formed during the reaction were filtered off and the filtrate evaporated to dryness. The residue was purified by flash chromatography (neat petroleum ether followed by a gradient of ethyl acetate up to 60%) to yield 2.56 g (9.98 mmol, 71%) of product as a beige solid.

$^1$H NMR (400 MHz, $d_6$-DMSO): 1.20-1.22 (m, 2H, $CH_2$), 1.29-1.43 (m, 13H, tBu, 2×$CH_2$), 2.86 (q, 2H, J=6.8 Hz and 12.9 Hz, $CH_2$), 3.07 (q, 2H, J=6.8 Hz and 12.9 Hz, $CH_2$), 5.53 (dd, 1H, J=2.3 Hz and 10.1 Hz, CH), 6.05 (dd, 1H, J=2.3 Hz and 17.2 Hz, CH), 6.20 (dd, 1H, J=10.1 Hz and 17.2 Hz, CH), 6.77 (t, 1H, J=5.3 Hz, NH), 8.04 (bs, 1H, NH).

Mass (electrospray+) calculated for $C_{13}H_{24}N_2O_3$ 256, found 279 (256+$Na^+$).

Step 2

N-(5-ammoniopentyl]acrylamide trifluoracetate

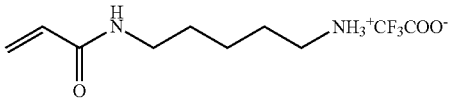

N-[5-(t-Bytoxycarbonyl)aminopentyl]acrylamide (2.56 g, 10 mmol) was dissolved in mixture of trifluoroacetic acid and dichloromethane (1:9, 100 ml) and stirred at room temperature. The progress of the reaction was monitored by TLC (dichloromethane:methanol 9:1). On completion, the reaction mixture was evaporated to dryness, the residue co-evaporated three times with toluene and then purified by flash chromatography (neat dichloromethane followed by a gradient of methanol up to 20%). Product was obtained as a white powder (2.43 g, 9 mmol, 90%).

$^1$H NMR (400 MHz, $D_2O$): 1.29-1.40 (m, 2H, $CH_2$), 1.52 (quint., 2H, J=7.1 Hz, $CH_2$), 1.61 (quint., 2H, J=7.7 Hz, CH2), 2.92 (t, 2H, J=7.6 Hz, $CH_2$), 3.21 (t, 2H, J=6.8 Hz, $CH_2$), 5.68 (dd, 1H, J=1.5 Hz and 10.1 Hz, CH), 6.10 (dd, 1H, J=1.5 Hz and 17.2 Hz, CH), 6.20 (dd, 1H, J=10.1 Hz and 17.2 Hz, CH).

Mass (electrospray+) calculated for $C_8H_{16}N_2O$ 156, found 179 (156+$Na^+$).

Step 3.

N-[5-(2-Bromoacetyl) aminopentyl]acrylamide (1)

To a suspension of N-(5-ammoniopentyl]acrylamide trifluoracetate (6.12 g, 22.64 mmol) and DIPEA (6.94 ml, 2.2 eq) in THF (120 ml) was added bromoacetyl chloride (2.07 ml, 1.1 eq) through a pressure equalized dropping funnel, over a one hour period and at −60° C. (cardice and isopropanol bath). The reaction mixture was then stirred at room temperature overnight and the completion of the reaction was checked by TLC (dichloromethane:methanol 9:1) the following day. The salts formed during the reaction were filtered off and the reaction mixture evaporated to dryness. The residue was purified by chromatography (neat dichloromethane followed by a gradient of methanol up to 5%). 3.2 g (11.55 mmol, 51%) of the product (N-[5-(2-Bromoacetyl) aminopentyl]acrylamide) were obtained as a white powder. A further recrystallization performed from petroleum ether: ethyl acetate mixture gave 3 g of the product.

$^1$H NMR (400 MHz, $d_6$-DMSO): 1.21-1.30 (m, 2H, $CH_2$), 1.34-1.48 (m, 4H, 2×$CH_2$), 3.02-3.12 (m, 4H, 2×$CH_2$), 3.81 (s, 2H, $CH_2$), 5.56 (d, 1H, J=9.85 Hz, CH), 6.07 (d, 1H, J=16.9 Hz, CH), 6.20 (dd, 1H, J=10.1 Hz and 16.9 Hz, CH), 8.07 (bs, 1H, NH), 8.27 (bs, 1H, NH).

Mass (electrospray+) calculated for $C_{10}H_{17}BrN_2O_2$ 277 (276 and 278, found 279 (278+$H^+$), 299 (276+$Na^+$)

The Cluster Formation Process

Fluidics

For all fluidic steps during the cluster formation process, a peristaltic pump Ismatec IPC equipped with tubing Ismatec Ref 070534-051 (orange/yellow, 0.51 mm internal diameter) is used. The pump is run in the forward direction (pulling fluids). A waste dish is installed to collect used solution at the outlet of the peristaltic pump tubing. During each step of the process, the different solutions used are dispensed into 8 tube microtube strips, using 1 tube per chip inlet tubing, in order to monitor the correct pumping of the solutions in each channel. The volume required per channel is specified for each step.

Thermal Control

To enable incubation at different temperatures during the cluster formation process, the Silex chip is mounted on top of an MJ-Research thermocycler. The chip sits on top of a custom made copper block, which is attached to the flat heating block of the thermocycler. The chip is covered with a small Perspex block and is held in place by adhesive tape.

Both pump and thermocycler are controlled by computer run scripts, which prompt the user to change solutions between each step.

1.Grafting Primers Onto Surface of SFA Coated Chip

An SFA coated chip is placed onto a modified MJ-Research thermocycler and attached to a peristaltic pump as described above. Grafting mix consisting of 0.5 μM of a forward primer and 0.5 μM of a reverse primer in 10 mM phosphate buffer (pH 7.0) is pumped into the channels of the chip at a flow rate of 60 μl/min for 75 s at 20° C. The thermocycler is then heated up to 51.6° C., and the chip is incubated at this temperature for 1 hour. During this time, the grafting mix undergoes 18 cycles of pumping: grafting mix is pumped in at 15 μl/min for 20 s, then the solution is pumped back and forth (5 s forward at 15 μl/min, then 5 s backward at 15 μl/min) for 180 s. After 18 cycles of pumping, the chip is washed by pumping in 5×SSC/5 mM EDTA at 15 μl/min for 300 s at 51.6° C. The thermocycler is then cooled to 20° C.

2.Template DNA Hybridisation

The DNA templates to be hybridised to the grafted chip are diluted to the required concentration (currently 0.5-2 pM) in 5×SSC/0.1% Tween. The diluted DNA is heated on a heating block at 100° C. for 5 min to denature the double stranded DNA into single strands suitable for hybridisation. The DNA is then immediately snap-chilled in an ice/water bath for 3 min. The tubes containing the DNA are briefly spun in a centrifuge to collect any condensation, and then transferred to a pre-chilled 8-tube strip and used immediately.

The grafted chip from step 1 is primed by pumping in 5×SSC/0.1% Tween at 60 μl/min for 75 s at 20° C. The thermocycler is then heated to 98.5° C., and the denatured DNA is pumped in at 15 μl/min for 300 s. An additional pump at 100 μl/min for 10 s is carried out to flush through bubbles formed by the heating of the hybridisation mix. The temperature is then held at 98.5° C. for 30 s, before being cooled slowly to 40.2° C. over 19.5 min. The chip is then washed by pumping in 0.3×SSC/0.1% Tween at 15 μl/min for 300 s at 40.2° C. The script then runs straight to the next step.

3.Bridge Amplification

The hybridised template molecules are amplified by a bridging polymerase chain reaction using the grafted primers and a thermostable polymerase.

PCR buffer consisting of 10 mM Tris (pH 9.0), 50 mM KCl, 1.5 mM $MgCl_2$, 1 M betaine and 1.3% DMSO is pumped into the chip at 15 μl/min for 200 s at 40.2° C. Then PCR mix of the above buffer supplemented with 200 μM dNTPs and 25 U/ml Taq polymerase is pumped in at 60 μl/min for 75 s at 40.2° C. The thermocycler is then heated to 74° C. and held at this temperature for 90 s. This step enables extension of the surface bound primers to which the DNA template strands are hybridised. The thermocycler then carries out 50 cycles of amplification by heating to 98.5° C. for 45 s (denaturation of bridged strands), 58° C. for 90 s (annealing of strands to surface primers) and 74° C. for 90 s (primer extension). At the end of each incubation at 98.5° C., fresh PCR mix is pumped into the channels of the chip at 15 μl/min for 10 s. As well as providing fresh reagents for each cycle of the PCR, this step also removes DNA strands and primers which have become detached from the surface and which could lead to contamination between clusters. At the end of thermocycling, the chip is cooled to 20° C. The chip is then washed by pumping in 0.3×SSC/0.1% Tween at 15 μl/min for 300 s at 74° C. The thermocycler is then cooled to 20° C.

4.Linearization

Linearization mix consisting of 0.1 M sodium periodate and 0.1 M ethanolamine is pumped into the chip at 15 μl/min for 1 hr at 20° C. The chip is then washed by pumping in water at 15 μl/min for 300 s at 20° C.

5.Blocking (Optional)

This step uses Terminal Transferase to incorporate a dideoxynucleotide onto the free 3' OH ends of DNA strands (both grafted primers and amplified cluster molecules).

Blocking buffer consisting of 50 mM potassium acetate, 20 mM Tris-acetate, 10 mM magnesium acetate, 1 mM dithiothreitol (pH 7.9) and 250 μM $CoCl_2$ is pumped into the chip at 15 μl/min for 200 s at 20° C. Then Blocking Mix of the above buffer supplemented with 2.4 μM ddNTPs and 250 U/ml Terminal Transferase is pumped in at 15 μl/min for 300 s at 37.7° C. The thermocycler is held at 37.7° C. for 30 min, $d_{ur}i_{ng\ w}$hich time Blocking Mix is pumped into the chip at 15 μl/min for 20 s every 3 min. After blocking, the chip is then washed by pumping in 0.3 ×SSC/0.1% Tween at 15 μl/min for 300 s at 20° C.

6.Denaturation of Clusters and Hybridisation of Sequencing Primer

This step uses NaOH to denature and wash away one of the strands of the amplified, linearised and blocked clusters. After a wash to remove the NaOH, the sequencing primer is then hybridised onto the single strands left on the surface.

After blocking, the double stranded DNA in the clusters is denatured by pumping in 0.1N NaOH at 15 μl/min for 300 s at 20° C. The chip is then washed by pumping in TE (10 mM Tris pH 8.0, 1 mM EDTA) at 15 μl/min for 300 s at 20° C. Sequencing primer is diluted to 0.5 μM in 5×SSC/0.1% Tween, and pumped into the channels at 15 μl/min for 300 s at 20° C. The thermocycler is then heated up to 60° C. and held at this temperature for 15 min. The thermocycler is then cooled to 40.2° C. and the chip is washed by pumping in 0.3×SSC/0.1% Tween at 15 μl/min for 300 s.

The clusters are now ready for $1^{st}$ cycle sequencing enzymology.

The DNA sequence used in this process was a single monotemplate sequence of 400 bases, with ends complementary to the grafted primers. The duplex DNA was denatured as described above.

The primers are typically 5'-phosphorothioate oligonucleotides incorporating any specific sequences or modifications required for cleavage. Their sequences and suppliers vary according to the experiment they are to be used for, and in this case were complementary to the 5'-ends of the template duplex.

Sequencing of Linearised Clusters

The amplified clusters contained a diol linkage in one of the grafted primers. Diol linkages can be introduced by including a suitable linkage into one of the primers used for solid-phase amplification.

Suitable primers including any desired template-specific sequence can be manufactured by standard automated DNA synthesis techniques using components available from commercial suppliers (e.g. Fidelity Systems Inc., ATD).

A cleavable diol-containing primer would typically have the following structure:

5'-phosphorothioate-arm 26-diol22A-sequence-3'OH wherein "sequence" represents a sequence of nucleotides capable of hybridising to the template to be amplified.

The structures of the arm26 and diol22A components (from Fidelity Systems Inc, MD, USA) are as follows:

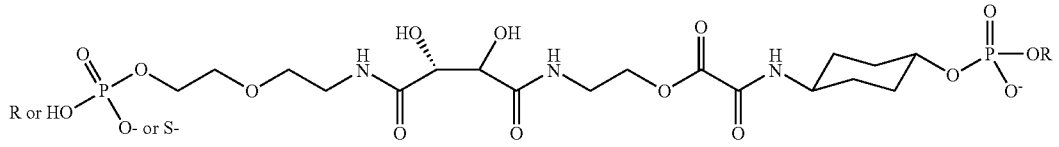

Diol 22A

-continued

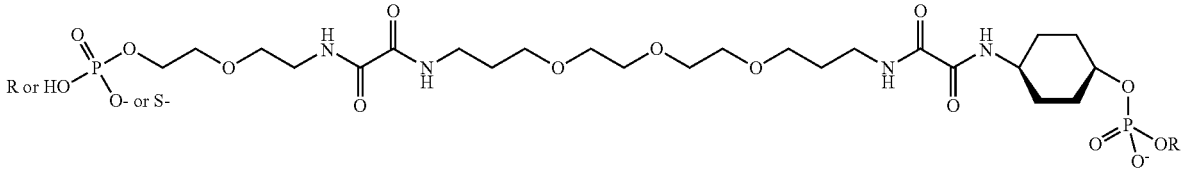

Arm 26

Products containing such diol linkages can be cleaved using periodate as described above, and the resulting single stranded polynucleotides hybridised as described above.

DNA Sequencing Cycles

Sequencing was carried out using modified nucleotides prepared as described above. A nucleotide kit (also called incorporation mix) was prepared and used throughout the whole sequencing experiment A mutant 9° N polymerase enzyme (an exo- variant including the triple mutation L408Y/Y409A/P410V and C223S) was used for the nucleotide incorporation steps.

Incorporation mix: Incorporation buffer (50 mM Tris-HCl pH 8.0, 6 mM MgSO4, 1 mM EDTA, 0.05% (v/v) Tween 20, 50 mM NaCl) plus 110 nM YAV exo- C223S, and 1 μM each of the four labelled modified nucleotides, was applied to the clustered templates, and heated to 45° C.

Templates were maintained at 45° C. for 30 min, cooled to 20° C. and washed with Incorporation buffer, then with 5×SSC/0.05% Tween 20.Templates were then exposed to Imaging buffer (100 mM Tris pH 7.0, 30 mM NaCl, 0.05% Tween 20, 50 mM sodium ascorbate, freshly dissolved).

Templates were scanned in 4 colours at room temp.

Templates were then exposed to sequencing cycles of Cleavage and Incorporation as follows:

Cleavage

Prime with Cleavage buffer (0.1 M Tris pH 7.4, 0.1 M NaCl and 0.05% Tween 20). Heat to 60° C.

Treat the clusters with Cleavage mix (100 mM TCEP in Cleavage buffer).

Wait for a total of 15 min in addition to pumping fresh buffer every 4 min.

Cool to 20° C.

Wash with Enzymology buffer.

Wash with 5×SSC/0.05% Tween 20.

Prime with Imaging buffer.

Scan in 4 colours at RT.

Incorporation

Prime with Incorporation buffer Heat to 60° C.

Treat with Incorporation mix. Wait for a total of 15 min in addition to pumping fresh Incorporation mix every 4 min.

Cool to 20° C.

Wash with Incorporation buffer.

Wash with 5×SSC/0.05% Tween 20.

Prime with imaging buffer.

Scan in 4 colours at RT.

Repeat the process of Incorporation and Cleavage for as many cycles as required.

Incorporated nucleotides were detected using a fluorescent imaging apparatus built for sequencing clustered arrays as described. The system comprises a mounted flow cell chip, a fluid direction system that controllably moves various reagents (e.g., buffers, labelled nucleotides wherein each type of nucleotide has its own specific fluorescent moiety, etc.) into contact with the polynucleotides; a temperature control system that regulates the temperature of the substrate and/or of the reagents; a TIRF laser system for exciting the fluorescent moiety; a detector component (e.g., a CCD camera and objective lenses, etc.) that is proximal to the substrate and which detects fluorescence from the laser excited moiety; a computer, connected to the detector, which has instruction sets for acquiring fluorescence data from the detector and optionally for determining sequence of the polynucleotide based on the fluorescence data.

Each of each chip was recorded in each of the four colours corresponding to the labelled nucleotides. The images were analysed to pick the brightest colour for each cluster, and this image intensity analysis was used to call the base for each cluster at each cycle. Images from each cycle were colocalised to obtain the sequence corresponding to each cluster. As the sequence of each cluster is known; and is the same for every cluster in the above experiment, the error rates (i.e. clusters not called as the correct sequence) can be analysed for each cycle of nucleotide incorporation. The error rates were less than 1% for the first 20 cycles of the experiment, meaning the known sequence of the monotemplate was correctly identified.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. A compound of the Formula (I): [

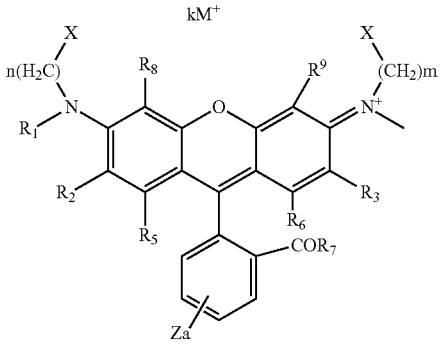

]

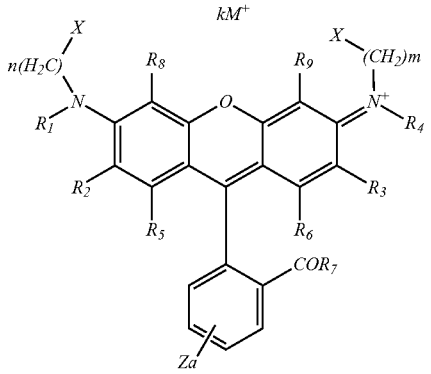

wherein

X is $SO_3^-$, $M^+$ is a common counter ion, k and m are independently integers from 1 to 6, n is 3, $R_1$, $R_4$, $R_5$, $R_6$, $R_8$ and $R_9$ are all H, $R_2$ and $R_3$ are independently H or $CH_3$, Z is carboxy-, carboxamido- or a substituted carboxamido group, a is 1 and $R_7$ is OH.

2. A compound of the Formula (I):

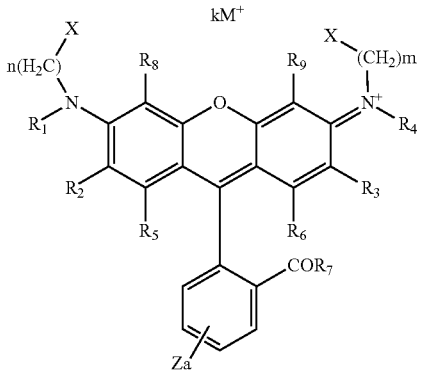

wherein

X is $SO_3H$ or $SO_3^-$, $M^+$ is a common counter ion, k, n, m are independently integers from 1 to 6, $R_1$ is linked to $R_2$ via a chain of $CH_2$ groups to form a ring, [or]

$R_4$ is linked to $R_3$ via a chain of $CH_2$ groups to form a ring, $R_5$ and $R_6$ are independently H, alkyl or substituted alkyl group, halogen, hydroxy- or alkoy group, $R_8$ is H, halogen, hydroxy- or alkoxy group, alkyl or substituted alkyl group or together with $R_1$ is a carbon or heterosubstituted carbon chain forming a ring, $R_9$ is H, halogen, hydroxy- or alkoxy group, alkyl or substituted alkyl group or together with $R_4$ is a carbon or heterosubstituted carbon chain forming a ring, $R_7$ is $NR_{11}R_{12}$ where $R_{11}$ is H, alkyl or a substituted alkyl, and $R_{12}$ is a substituted alkyl, Z is halogen, amino or substituted amino, [hydroxyl-] *hydroxy*-, alkoxy-, carboxy-, carboxamido- or a substituted carboxamido group, $SO_3H$ or $SO_3^-$, and a is 0 to 4[, wherein if a is 0, $R_7$ is $NR_{11}R_{12}$ where $R_{11}$ and $R_{12}$ are independently H, alkyl or a substituted alkyl].

3. The compound of claim 2, wherein a is 0, $R_{11}$ is H or alkyl, $R_{12}$ is an alkyl substituted with $COOR_{13}$, and $R_{13}$ is H, alkyl or substituted alkyl group, halogen, hydroxy- or alkoxy group.

4. A compound of the Formula (I):

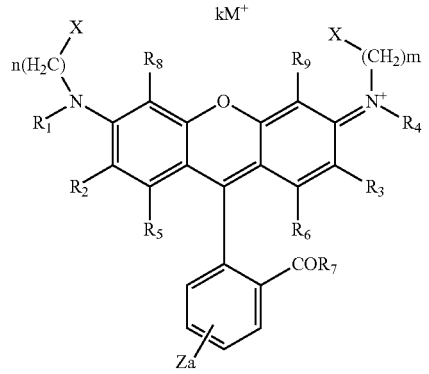

wherein

X is $SO_3^-$, $M^+$ is a common counter ion, k is an integer from 1 to 6, n=3, m=3 and $R_1$ is [H or an alkyl or substituted alkyl group] $(CH_2)_m SO_3^-$, $R_2$, $R_3$, $R_5$, $R_6$, $R_8$ and $R_9$ are all H, $R_4$ is [H, or an alkyl or substituted alkyl group] $(CH_2)_m SO_3^-$, $R_7$ is OH[or is joined to form aliphatic or aromatic cyclic or substituted aliphatic-, aromatic- or heterocyclic rings], Z is halogen, amino or substituted amino, [hydroxyl-] *hydroxy*-, alkoxy-, carboxy-, carboxamido- or a substituted carboxamido group, $SO_3H$ or $SO_3^-$ and a is 0.

[5. A compound of claim 4, wherein $R_1$ and $R_4$ are $(CH_2)_m SO_3^-$.]

6. A nucleotide or oligonucleotide labelled with a compound according to claim 1, 2, 3, or 4.

7. A labelled nucleotide or oligonucleotide according to claim 6 wherein the label is attached to the C5 position of a pyrimidine base or the C7 position of a 7-deaza purine base through a linker moiety.

8. A labelled nucleotide or oligonucleotide according to claim 7 wherein said linker moiety comprises a moiety selected from the group consisting of:

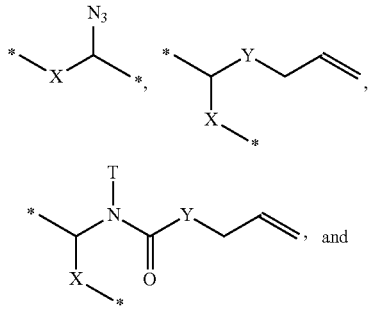

-continued

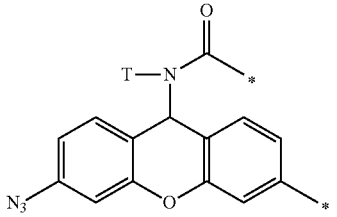

wherein

X *in said linker moiety* is selected from the group comprising O, S, NH and NQ;

wherein Q is a C1-10 substituted or unsubstituted alkyl group,

Y is selected from the group comprising O, S, NH and N(allyl),

T is hydrogen or a C1-10 substituted or unsubstituted alkyl group.

9. A labelled nucleotide according to claim 7, further comprising a 3' OH blocking group covalently attached to the ribose or deoxyribose sugar of the nucleotide.

10. A kit comprising two or more nucleotides wherein at least one nucleotide is a labelled nucleotide according to claim 6.

11. A kit according to claim 10 wherein each nucleotide can be cleaved from an attached compound by chemical or enzymatic treatment.

12. A kit according to claim 11 wherein said chemical treatment comprises treating with a phosphine reagent.

13. A kit according to claim 10 wherein two of the labelled nucleotides are [excited] *excitable* using a single laser.

14. A kit according to claim 10 wherein a first of four nucleotides is the labelled nucleotide and the second, third, and fourth nucleotides are each labelled with a different compound, wherein each compound has a distinct absorbance maximum and each of the compounds is distinguishable from the other three compounds.

15. A kit according to claim 14 wherein the second and third labelled nucleotides have a distinct absorbance maximum above 600 nm.

16. A kit according to claim 14 wherein the first of four nucleotides is the labelled nucleotide and a second and third nucleotide are each labelled with a different compound, wherein each of the compounds of the second and third nucleotides can be excited using a single laser with a wavelength between 630-700 nm.

17. A kit according to claim 14 wherein the first of four nucleotides is the labelled nucleotide and a second, third, and fourth nucleotide are each labelled with a different compound, wherein the compound of the second nucleotide can be excited using a laser with a wavelength at 532 nm and each of the compounds of the third and fourth nucleotides can be excited using a single laser with a wavelength at 660 nm.

18. A kit according to claim 10 further comprising a DNA polymerase.

19. A method of synthesizing a compound of the Formula (I):

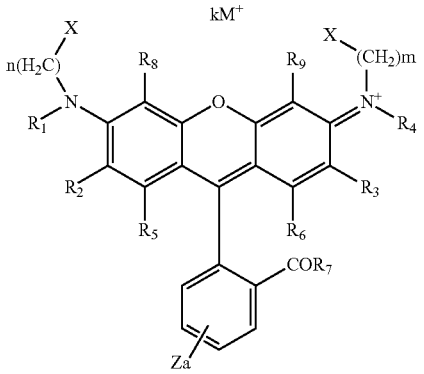

wherein

X is $SO_3H$ or $SO_3^-$, $M^+$ is a common counter ion, k, n, m are independently integers from 1 to 6, $R_1$ is H or an alkyl or substituted alkyl group, $R_2$ is H, alkyl or substituted alkyl group, halogen, carboxy, carboxamide, hydroxy- or alkoxy group, or $R_2$ together with $R_1$ or $R_5$ is a carbon or heterosubstituted chain forming a ring, $R_3$ is H, alkyl or substituted alkyl group, halogen, carboxy, carboxamide, hydroxy- or alkoxy group $R_4$ is H, or an alkyl or substituted alkyl group, or $R_3$ together with $R_4$ or $R_6$ is a carbon or heterosubstituted chain forming a ring, $R_5$ and $R_6$ are independently H, alkyl or substituted alkyl group, halogen, hydroxy- or alkoxy group, $R_8$ is H, halogen, hydroxy- or alkoxy group, alkyl or substituted alkyl group or together with $R_1$ is a carbon or heterosubstituted carbon chain forming a ring, $R_9$ is H, halogen, hydroxy- or alkoxy group, alkyl or substituted alkyl group or together with $R_4$ is a carbon or heterosubstituted carbon chain forming a ring, $R_7$ is OH, $OR_{10}$ where $R_{10}$ is alkyl or substituted alkyl, or $NR_{11}R_{12}$ where $R_{11}$ and $R_{12}$ are independently H, alkyl or a substituted alkyl, or is joined to form aliphatic or aromatic cyclic or substituted aliphatic-, aromatic- or heterocyclic rings, Z is halogen, amino or substituted amino, [hydroxyl-] *hydroxy*-, alkoxy-, carboxy-, carboxamido- or a substituted carboxamido group, $SO_3H$ or [$SO_3^{31}$] $SO_3^-$ and a is 0 to 4, wherein if a is 0, $R_7$ is $NR_{11}R_{12}$ where $R_{11}$ and $R_{12}$ are independently H, alkyl or a substituted alkyl, comprising the steps of:

(a) providing the following starting materials

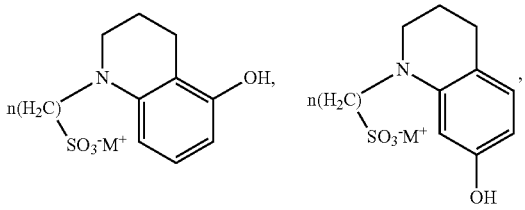

-continued

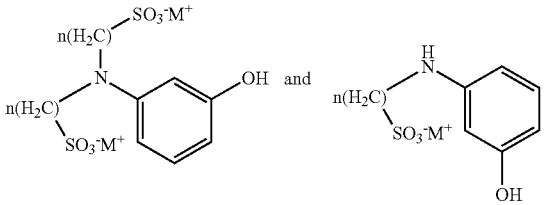

(b) further providing substituted or unsubstituted phthalic anhydride derivatives, and (c) allowing a condensation reaction to occur, thereby obtaining the compound.

20. The compound of claim 2, wherein

X is $SO_3^-$, $R_1$ and $R_2$ form a six membered ring, $R_3$ and $R_4$ form a six membered ring, Z is carboxy-, carboxamido- or a substituted carboxamido group, a is 1.

*21. The compound of claim 2, wherein*

*$R_8$ is H, halogen, hydroxy- or alkoxy group, alkyl or substituted alkyl group; and*

*$R_9$ is H, halogen, hydroxy- or alkoxy group, alkyl or substituted alkyl group.*

*22. The compound of claim 21, wherein*

*X is $SO_3^-$;*

*$M^+$ is selected from $Na^+$, $K^+$, $Li^+$, $NH_4^+$, and $N(Et)_3H^+$;*

*$R_1$ is linked to $R_2$ to form a six membered aliphatic ring;*

*$R_4$ is linked to $R_3$ to form a six membered aliphatic ring;*

*$R_5$, $R_6$, $R_8$, and $R_9$ are H;*

*n and m are 3;*

*k is 1 or 2;*

*$R_{11}$ is H or alkyl; and*

*$R_{12}$ is alkyl substituted with halo, cyano, $SO_3^-$, $NR_{13}R_{14}$, $CONR_{13}R_{14}$, COOH or $COOR_{13}$, and where $R_{13}$ and $R_{14}$ are each independently H, alkyl, substituted alkyl, alkenyl, substituted alkenyl, alkynyl, substituted alkynyl, aryl or substituted aryl.*

*23. The compound of claim 22, wherein*

*$R_{11}$ is H or methyl;*

*$R_{12}$ is alkyl substituted with —COOH; and*

*a is 0.*

*24. The compound of claim 23, having the structure of:*

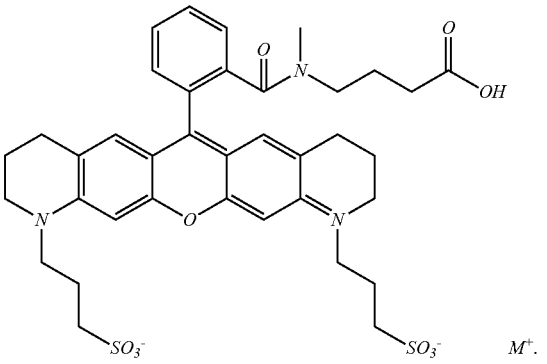

*25. The nucleotide or oligonucleotide according to claim 6, labeled with a compound of the Formula (I):*

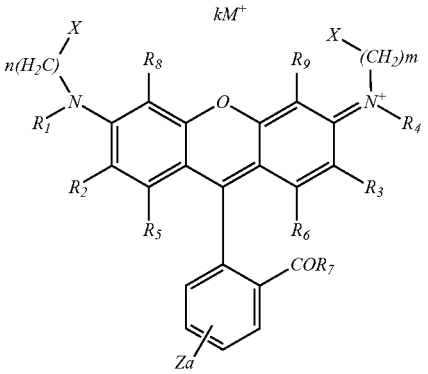

*wherein*

*X is $SO_3H$ or $SO_3^-$,*

*$M^+$ is a common counter ion,*

*k, n, m are independently integers from 1 to 6,*

*$R_1$ is linked to $R_2$ via a chain of $CH_2$ groups to form a ring,*

*$R_4$ is linked to $R_3$ via a chain of $CH_2$ groups to form a ring,*

*$R_5$ and $R_6$ are independently H, alkyl or substituted alkyl group, halogen, hydroxy- or alkoxy group,*

*$R_8$ is H, halogen, hydroxy- or alkoxy group, alkyl or substituted alkyl group or together with $R_1$ is a carbon or heterosubstituted carbon chain forming a ring,*

*$R_9$ is H, halogen, hydroxy- or alkoxy group, alkyl or substituted alkyl group or together with $R_4$ is a carbon or heterosubstituted carbon chain forming a ring,*

*$R_7$ is $NR_{11}R_{12}$ where $R_{11}$ is H, alkyl or a substituted alkyl, and $R_{12}$ is a substituted alkyl,*

*Z is halogen, amino or substituted amino, hydroxy-, alkoxy-, carboxy-, carboxamido- or a substituted carboxamido group, $SO_3H$ or $SO_3^-$, and*

*a is 0 to 4.*

*26. The nucleotide or oligonucleotide according to claim 25, wherein the nucleotide or oligonucleotide is a nucleotide.*

*27. The nucleotide according to claim 26, wherein the compound is attached to the C5 position of a pyrimidine base or the C7 position of a 7-deaza purine base through a cleavable linker moiety, wherein the nucleotide comprises a deoxyribose sugar and a cleavable 3' OH blocking group is covalently attached to the deoxyribose sugar of the nucleotide.*

*28. The nucleotide according to claim 27, wherein said linker moiety comprises:*

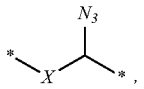

*wherein X in said linker moiety is O.*

*29. The nucleotide according to claim 27, wherein the 3' OH blocking group comprises the structure of*

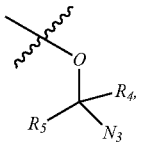

*wherein $R_4$ and $R_5$ in the 3' OH blocking group are H.*

30. The nucleotide according to claim 26, comprising a label moiety of the following structure:

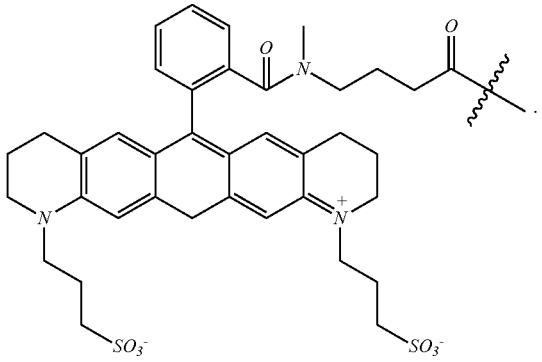

31. The nucleotide according to claim 30, wherein the nucleotide has the structure of:

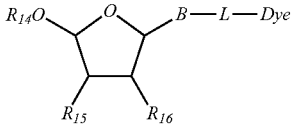

wherein
B is a nucleobase;
L is a linker moiety;
Dye is the label moiety;
$R_{14}$ is H, monophosphate, diphosphate, triphosphate, thiophosphate, or a phosphate ester;
$R_{15}$ is a cleavable 3' OH blocking group; and
$R_{16}$ is H or OH.

32. The nucleotide according to claim 31, wherein L comprises a moiety of the structure

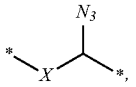

wherein X in said linker moiety is O;
$R_{14}$ is triphosphate;
$R_{15}$ is a 3' OH blocking group of the structure

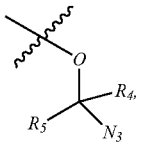

wherein $R_4$ and $R_5$ in the 3' OH blocking group are H; and
$R_{16}$ is H.

33. The nucleotide according to claim 32, where L comprises a moiety of the structure:

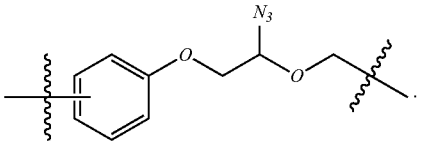

34. The nucleotide according to claim 33, wherein L has the structure:

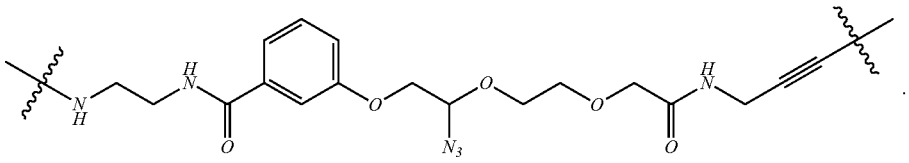

35. The nucleotide according to claim 34, wherein the nucleobase is 7-deaza adenine or 7-deaza guanine, and L is attached to the 7-deaza adenine or 7-deaza guanine at the C7 position.

36. The nucleotide according to claim 34, wherein the nucleobase is cytosine and L is attached to the cytosine at the C5 position.

37. The nucleotide according to claim 34, having the structure:

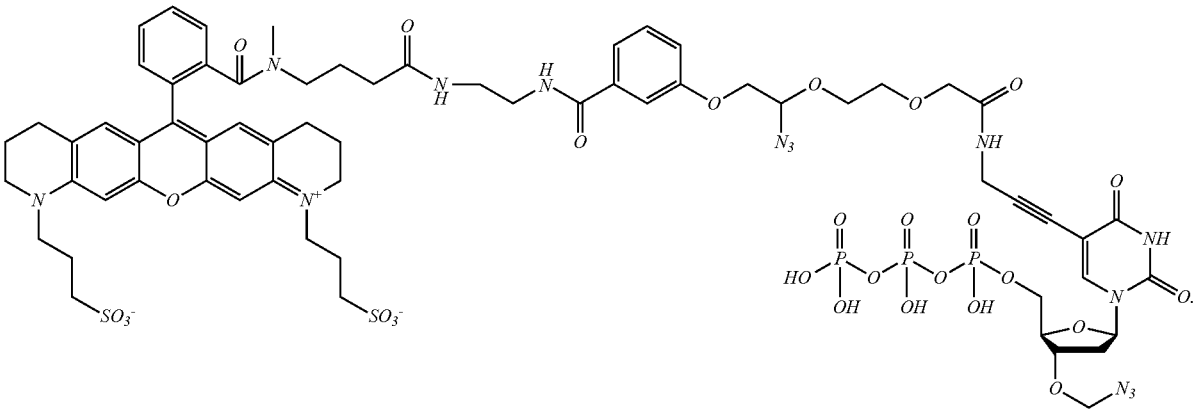

38. The nucleotide or oligonucleotide according to claim 25, wherein the nucleotide or oligonucleotide is an oligonucleotide hybridized to a template polynucleotide.

39. The oligonucleotide of claim 38, wherein the template polynucleotide is immobilized on a solid support.

40. The oligonucleotide according to claim 39, wherein the solid support comprises an array of a plurality of immobilized template polynucleotides.

41. The oligonucleotide of claim 38, comprising a label moiety of the following structure:

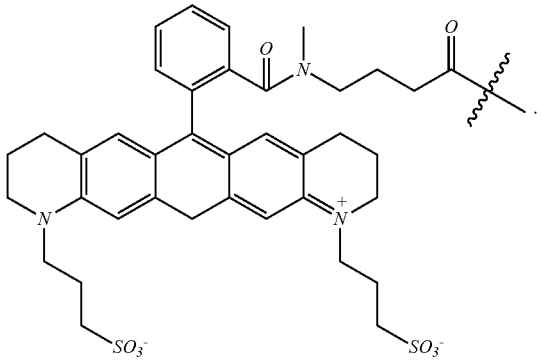

42. The oligonucleotide of claim 41, wherein the label moiety is attached to a nucleobase in the oligonucleotide through a cleavable linker moiety.

43. The oligonucleotide of claim 42, wherein the cleavable linker moiety has the structure:

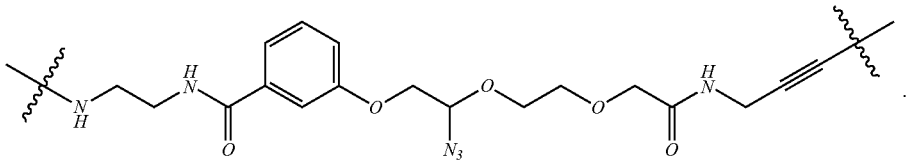

44. The kit according to claim 10, wherein the labelled nucleotide is a nucleotide labelled with a compound of the Formula (I):

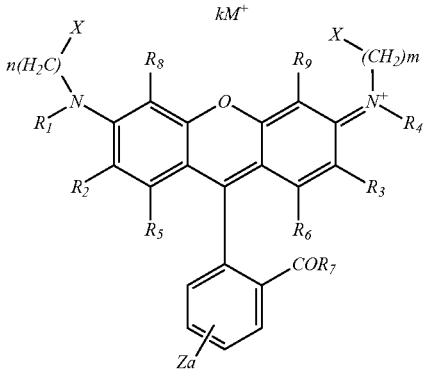

wherein

X is $SO_3H$ or $SO_3^-$, $M^+$ is a common counter ion, k, n, m are independently integers from 1 to 6, $R_1$ is linked to $R_2$ via a chain of $CH_2$ groups to form a ring, $R_4$ is linked to $R_3$ via a chain of $CH_2$ groups to form a ring, $R_5$ and $R_6$ are independently H, alkyl or substituted alkyl group, halogen, hydroxy- or alkoxy group, $R_8$ is H, halogen, hydroxy- or alkoxy group, alkyl or substituted alkyl group or together with $R_1$ is a carbon or heterosubstituted carbon chain forming a ring, $R_9$ is H, halogen, hydroxy- or alkoxy group, alkyl or substituted alkyl group or together with $R_4$ is a carbon or heterosubstituted carbon chain forming a ring, $R_7$ is $NR_{11}R_{12}$ where $R_{11}$ is H, alkyl or a substituted alkyl, and $R_{12}$ is a substituted alkyl, Z is halogen, amino or substituted amino, hydroxy-, alkoxy-, carboxy-, carboxamido- or a substituted carboxamido group, $SO_3H$ or $SO_3^-$, and a is 0 to 4.

45. The kit according to claim 44, wherein the labelled nucleotide comprises a label moiety of the following structure:

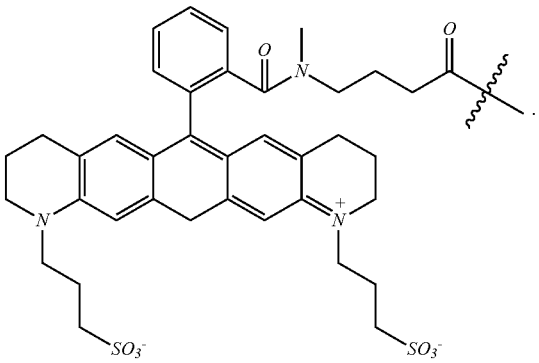

46. The kit according to claim 45, wherein the labelled nucleotide has the structure of:

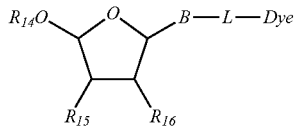

*wherein*

*B is a nucleobase;*

*L is:*

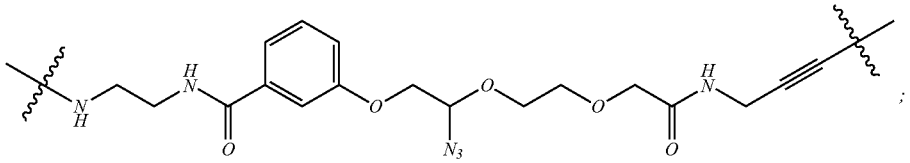

*Dye is the label moiety;*

*$R_{14}$ is triphosphate;*

*$R_{15}$ is a 3' OH blocking group of the structure*

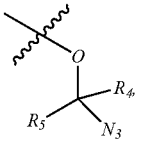

*wherein $R_4$ and $R_5$ in the 3' OH blocking group are H; and*

*$R_{16}$ is H.*

*47. The kit according to claim 45, wherein*

*a first of the nucleotides is the labelled nucleotide, and*

*a second of the nucleotides is labelled with a different compound, wherein the label moiety and the different compound have a difference in absorbance maximum of at least 10 nm.*

*48. The kit according to claim 47, wherein the label moiety and one of the different compounds have a difference in absorbance maximum of between 20 nm and 50 nm.*

*49. The kit according to claim 47, wherein the different compound excites at 532 nm.*

*50. The kit according to claim 49, wherein the different compound is*

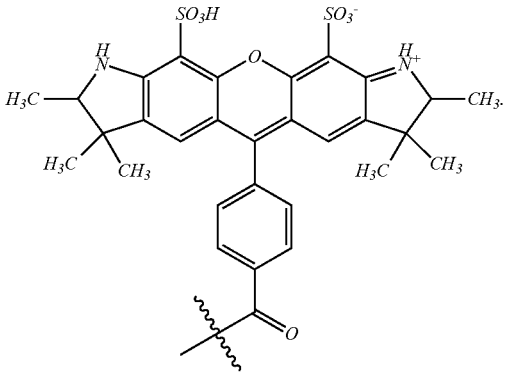

*51. The kit according to claim 49, wherein the second nucleotide has the structure of:*

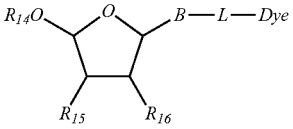

*wherein:*

*B is selected from adenine, guanine, cytosine, and thymine;*

*L is a linker moiety;*

*Dye is*

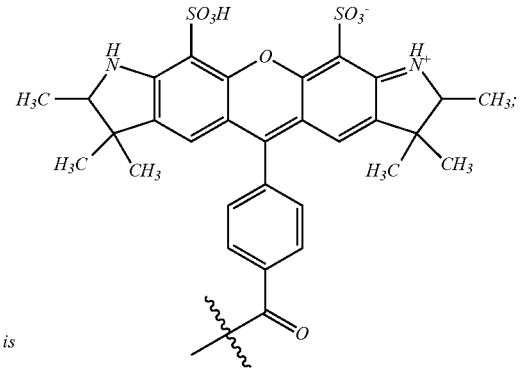

*$R_{14}$ is triphosphate;*

*$R_{15}$ is a cleavable 3' OH blocking group; and*

*$R_{16}$ is H.*

*52. The kit according to claim 47, wherein the different compound is a dicarbocyanine dye.*

*53. The kit according to claim 47, wherein the second nucleotide has the structure of:*

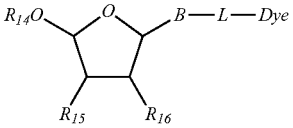

*wherein:*

*B is selected from adenine, guanine, cytosine, and thymine;*

*L is a linker moiety;*

*Dye is a dicarbocyanine dye;*

*$R_{14}$ is triphosphate;*

*$R_{15}$ is a cleavable 3' OH blocking group; and*

*$R_{16}$ is H.*

54. The kit according to claim 53, comprising a third nucleotide having the structure of:

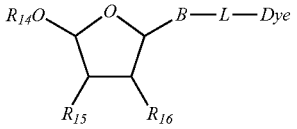

wherein:

B in the third nucleotide is selected from adenine, guanine, cytosine, and thymine;

L in the third nucleotide is a linker moiety;

Dye in the third nucleotide is

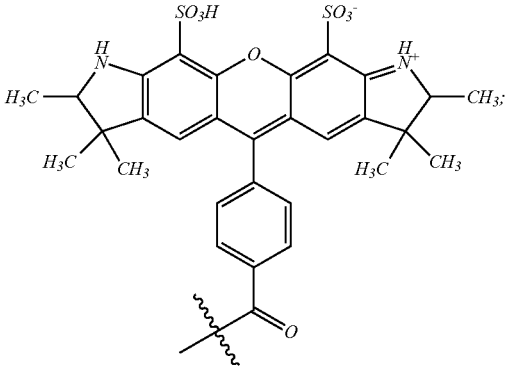

$R_{14}$ in the third nucleotide is triphosphate;

$R_{15}$ in the third nucleotide is a cleavable 3' OH blocking group; and $R_{16}$ in the third nucleotide is H.

55. The kit according to claim 47, comprising a third and fourth nucleotide labeled with a different compound, wherein the label moiety and each different compound has a different absorbance maximum and the label moiety and each of the different compounds are distinguishable from each other, wherein the third and fourth labelled nucleotides have distinct absorbance maximums above 600 nm.

56. The kit according to claim 55, wherein the third and fourth labelled nucleotides have distinct absorbance maximums above 640 nm.

57. The kit according to claim 45, further comprising a mutant DNA polymerase and one or more buffer compositions.

58. The kit according to claim 57, wherein the mutant DNA polymerase is mutant 9° N polymerase.

59. The kit according to claim 45, further comprising sodium ascorbate.

60. The kit according to claim 46, wherein a first of the nucleotides is the labelled nucleotide, and a second of the nucleotides is labelled with a different compound, wherein the label moiety and the different compound have a difference in absorbance maximum of at least 10 nm.

61. The kit according to claim 60, wherein the label moiety and one of the different compounds have a difference in absorbance maximum of between 20 nm and 50 nm.

62. The kit according to claim 60, wherein the different compound excites at 532 nm.

63. The kit according to claim 62, wherein the different compound is

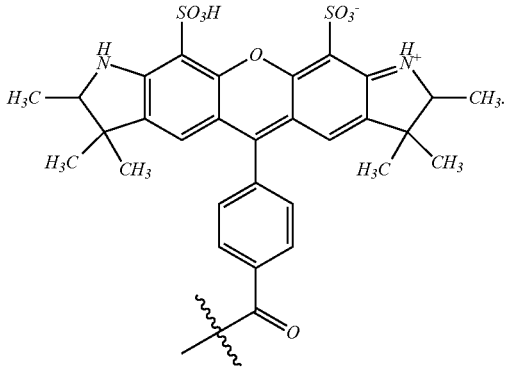

64. The kit according to claim 62, wherein the second nucleotide has the structure of:

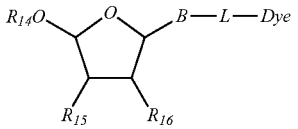

wherein:

B in the second nucleotide is selected from adenine, guanine, cytosine, and thymine;

L in the second nucleotide is a linker moiety;

Dye in the second nucleotide is

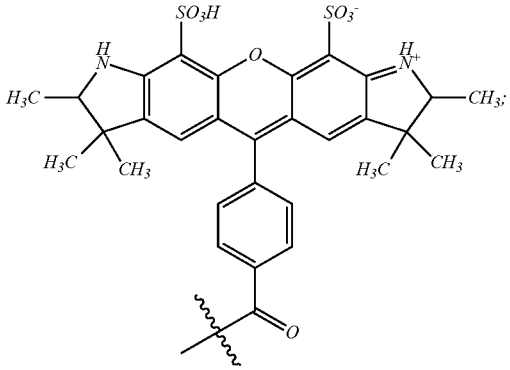

$R_{14}$ in the second nucleotide is triphosphate;

$R_{15}$ in the second nucleotide is a cleavable 3' OH blocking group; and $R_{16}$ in the second nucleotide is H.

65. The kit according to claim 60, wherein the different compound is a dicarbocyanine dye.

66. The kit according to claim 60, wherein the second nucleotide has the structure of:

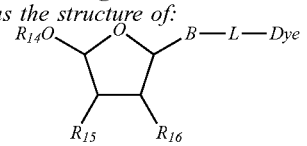

wherein:

B in the second nucleotide is selected from adenine, guanine, cytosine, and thymine;

L in the second nucleotide is a linker moiety;

Dye in the second nucleotide is a dicarbocyanine dye;

$R_{14}$ in the second nucleotide is triphosphate;

$R_{15}$ in the second nucleotide is a cleavable 3' OH blocking group; and $R_{16}$ in the second nucleotide is H.

67. The kit according to claim 66, comprising a third nucleotide having the structure of:

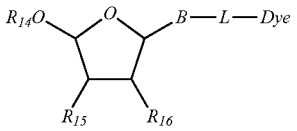

*wherein:*

*B in the third nucleotide is selected from adenine, guanine, cytosine, and thymine;*

*L in the third nucleotide is a linker moiety;*

*Dye in the third nucleotide is*

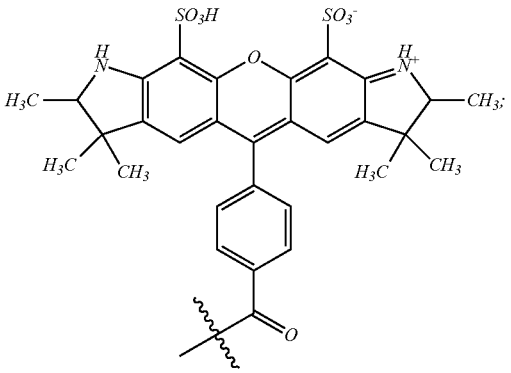

*$R_{14}$ in the third nucleotide is triphosphate;*

*$R_{15}$ in the third nucleotide is a cleavable 3' OH blocking group; and*

*$R_{16}$ in the third nucleotide is H.*

*68. The kit according to claim 60, comprising a third and fourth nucleotide labeled with a different compound, wherein the label moiety and each different compound has a distinct absorbance maximum and the label moiety and each of the different compounds are distinguishable from each other, wherein the second and third labelled nucleotides have a distinct absorbance maximum above 600 nm.*

*69. The kit according to claim 68, wherein the second and third labelled nucleotides have distinct absorbance maximums above 640 nm.*

*70. The kit according to claim 60, further comprising a DNA polymerase and one or more buffer compositions.*

*71. The kit according to claim 70, wherein the DNA polymerase is a mutant DNA polymerase.*

*72. The kit according to claim 71, wherein the mutant DNA polymerase is mutant 9° N polymerase.*

*73. The kit according to claim 70, comprising sodium ascorbate.*

* * * * *